US011293003B2

(12) United States Patent
Jones et al.

(10) Patent No.: US 11,293,003 B2
(45) Date of Patent: Apr. 5, 2022

(54) CONFIGURABLE FLUID MIXING SYSTEM HOUSING AND SUPPORT HARDWARE

(71) Applicant: LIFE TECHNOLOGIES CORPORATION, Carlsbad, CA (US)

(72) Inventors: Nephi Jones, Newton, UT (US); Steven Kjar, Logan, UT (US); Daniel Price, Logan, UT (US); Mark Smith, Nibley, UT (US); Paul Thacker, Lewiston, UT (US); Tony Hsiao, Providence, UT (US)

(73) Assignee: Life Technologies Corporation, Carlsbad, CA (US)

(*) Notice: Subject to any disclaimer, the term of this patent is extended or adjusted under 35 U.S.C. 154(b) by 156 days.

(21) Appl. No.: 16/238,656

(22) Filed: Jan. 3, 2019

(65) Prior Publication Data
US 2019/0218494 A1   Jul. 18, 2019

Related U.S. Application Data

(60) Provisional application No. 62/712,343, filed on Jul. 31, 2018, provisional application No. 62/670,934, (Continued)

(51) Int. Cl.
C12M 1/00 (2006.01)
C12M 1/36 (2006.01)
(Continued)

(52) U.S. Cl.
CPC .......... C12M 35/04 (2013.01); B01F 3/04531 (2013.01); B01F 7/0005 (2013.01);
(Continued)

(58) Field of Classification Search
CPC .......... B01F 15/00538; B01F 15/00707; B01F 15/00772; B01F 15/0085;
(Continued)

(56) References Cited

U.S. PATENT DOCUMENTS 659,345 A    10/1900 Ivins
1,711,114 A   4/1929 Hunt
(Continued)

FOREIGN PATENT DOCUMENTS

CN    101163538 A    4/2008
CN    202606066 U    12/2012
(Continued)

OTHER PUBLICATIONS

ATMI Life Sciences, Integrity PadReadtor, A New Culture in Cell Growth, published as early as 2010, 4 pages.
(Continued)

Primary Examiner — Gautam Prakash
Assistant Examiner — Lydia Edwards
(74) Attorney, Agent, or Firm — Workman Nydegger

(57) ABSTRACT

The present set of embodiments relate a system, method, and various devices for installation of a bioproduction system. The bioproduction system includes a rigid housing having a moveable platform to assist in the installation of a bioprocessing container within. The system also includes mounting systems for a variety of peripherals originating from the flexible container while safeguarding operators. More specifically, the system includes systems and methods for mounting bearings, organizing tube sets, and placement of the flexible container in its proper orientation.

18 Claims, 64 Drawing Sheets

Related U.S. Application Data filed on May 14, 2018, provisional application No. 62/618,215, filed on Jan. 17, 2018.

(51) Int. Cl.

| | | |
|---|---|---|
| *C12M 1/02* | (2006.01) | |
| *B01F 15/00* | (2006.01) | |
| *C12M 1/42* | (2006.01) | |
| *C12N 5/071* | (2010.01) | |
| *C12M 1/06* | (2006.01) | |
| *B01F 3/04* | (2006.01) | |
| *B01F 7/00* | (2006.01) | |
| *B01F 7/24* | (2006.01) | |
| *B01F 7/18* | (2006.01) | |

(52) U.S. Cl.
CPC ...... *B01F 7/00391* (2013.01); *B01F 7/00725* (2013.01); *B01F 7/24* (2013.01); *B01F 15/0085* (2013.01); *B01F 15/00538* (2013.01); *B01F 15/00707* (2013.01); *B01F 15/00772* (2013.01); *C12M 23/50* (2013.01); *C12M 23/58* (2013.01); *C12M 27/02* (2013.01); *C12M 27/06* (2013.01); *C12M 41/48* (2013.01); *C12N 5/0602* (2013.01); *B01F 7/18* (2013.01); *B01F 2003/04673* (2013.01); *B01F 2015/0011* (2013.01); *B01F 2015/00603* (2013.01); *B01F 2215/0073* (2013.01); *C12N 2527/00* (2013.01)

(58) Field of Classification Search
CPC .... B01F 2003/04673; B01F 2015/0011; B01F 2015/00603; B01F 2215/0073; B01F 3/04531; B01F 7/0005; B01F 7/00391; B01F 7/00725; B01F 7/18; B01F 7/24; C12M 23/50; C12M 23/58; C12M 27/02; C12M 27/06; C12M 35/04; C12M 41/48; C12N 2527/00; C12N 5/0602
See application file for complete search history.

(56) References Cited

U.S. PATENT DOCUMENTS

| | | | |
|---|---|---|---|
| 1,752,833 | A | 4/1930 | Brumder |
| 1,778,188 | A | 10/1930 | De Motte |
| 1,898,724 | A | 2/1933 | Gifford |
| 1,954,093 | A | 4/1934 | Nelson |
| 2,552,057 | A | 5/1951 | Paik |
| 2,896,926 | A | 7/1959 | Chapman |
| 3,281,124 | A | 10/1966 | Juri et al. |
| 3,322,401 | A | 5/1967 | Mersch |
| 3,559,962 | A | 2/1971 | Enssle et al. |
| 3,692,427 | A | 9/1972 | Risse |
| 4,083,653 | A | 4/1978 | Stiffler |
| 4,355,906 | A | 10/1982 | Ono |
| D273,709 | S | 5/1984 | Schneider |
| 4,712,922 | A | 12/1987 | Peterl |
| 4,722,608 | A | 2/1988 | Salzman et al. |
| D336,034 | S | 6/1993 | Rebilas |
| 5,411,331 | A | 5/1995 | Griffin |
| 5,454,797 | A | 10/1995 | Haswell |
| 5,885,001 | A | 3/1999 | Thomas |
| 5,896,989 | A | 4/1999 | Ropiak |
| 5,941,636 | A | 8/1999 | Lu |
| 6,083,587 | A | 7/2000 | Smith et al. |
| D439,328 | S | 3/2001 | Nielsen |
| 6,670,171 | B2 | 12/2003 | Carll |
| 6,844,186 | B2 | 1/2005 | Carll |
| 7,229,206 | B2 | 6/2007 | Whitney |
| 7,384,783 | B2 | 6/2008 | Kunas et al. |
| 7,441,940 | B2 | 10/2008 | Vanek |
| 7,487,688 | B2 | 2/2009 | Goodwin |
| 7,682,067 | B2 | 3/2010 | West et al. |
| 7,878,099 | B2 | 2/2011 | Loibl |
| 7,879,599 | B2 | 2/2011 | Goodwin et al. |
| D662,212 | S | 6/2012 | Quisenberry |
| 8,272,410 | B2 | 9/2012 | Elgan et al. |
| 8,342,737 | B2 | 1/2013 | Greller et al. |
| D679,023 | S | 3/2013 | Quisenberry |
| 8,455,242 | B2 | 6/2013 | Staheli et al. |
| 8,506,198 | B2 | 8/2013 | West et al. |
| 8,603,805 | B2 | 12/2013 | Goodwin et al. |
| 8,641,314 | B2 | 2/2014 | Thacker et al. |
| 9,005,971 | B2 | 4/2015 | Jones et al. |
| 9,643,133 | B2 | 5/2017 | Goodwin et al. |
| 9,839,886 | B2 | 12/2017 | Staheli et al. |
| 9,932,553 | B2 | 4/2018 | Jones et al. |
| D824,042 | S | 7/2018 | Scott |
| D830,544 | S | 10/2018 | Kisner |
| D857,188 | S | 8/2019 | Moran |
| D870,315 | S | 12/2019 | Wahlqvist |
| D870,989 | S | 12/2019 | Penland |
| 2002/0105856 | A1 | 8/2002 | Terentiev |
| 2002/0131654 | A1 | 9/2002 | Smith et al. |
| 2003/0077466 | A1 | 4/2003 | Smith et al. |
| 2006/0240546 | A1 | 10/2006 | Goodwin et al. |
| 2006/0270036 | A1 | 11/2006 | Goodwin et al. |
| 2007/0014187 | A1 | 1/2007 | Kaas |
| 2010/0165785 | A1 | 7/2010 | Kaas |
| 2010/0260010 | A1 | 10/2010 | Jornitz |
| 2011/0013473 | A1 | 1/2011 | Ludwig et al. |
| 2011/0013474 | A1 | 1/2011 | Ludwig et al. |
| 2011/0026360 | A1 | 2/2011 | Greller et al. |
| 2011/0058447 | A1 | 3/2011 | Reif et al. |
| 2011/0058448 | A1 | 3/2011 | Reif et al. |
| 2011/0188928 | A1 | 8/2011 | West et al. |
| 2011/0229963 | A1 | 9/2011 | Fatherazi et al. |
| 2011/0310696 | A1 | 12/2011 | Goodwin et al. |
| 2013/0101982 | A1 | 4/2013 | Goodwin et al. |
| 2013/0279289 | A1 | 10/2013 | Eggler et al. |
| 2014/0106453 | A1 | 4/2014 | Kunas |
| 2015/0117142 | A1 | 4/2015 | Staheli et al. |
| 2017/0011714 | A1 | 1/2017 | Eim et al. |
| 2017/0183617 | A1 | 6/2017 | Jones et al. |

FOREIGN PATENT DOCUMENTS

| | | |
|---|---|---|
| DE | 202009005407 U1 | 9/2009 |
| DE | 102008058338 A1 | 5/2010 |
| EP | 1776998 A1 | 4/2007 |
| EP | 2 123 745 A2 | 11/2009 |
| FR | 0782935 A | 7/1935 |
| JP | 06-285353 A | 10/1994 |
| JP | 2004-532719 A | 10/2004 |
| JP | 2013-544186 A | 12/2013 |
| WO | 2010/089151 A1 | 8/2010 |
| WO | 2011/139209 A1 | 11/2011 |
| WO | 2012/097079 A2 | 7/2012 |
| WO | 2013/151733 A1 | 10/2013 |
| WO | 2015/039034 A1 | 3/2015 |
| WO | 2017/023638 A1 | 2/2017 |
| WO | 2017/064058 A1 | 4/2017 |

OTHER PUBLICATIONS

ATMI Life Sciences, Integrity PadReadtor, All Applications, High-End Controls and Abilities, published as early as 2010, 4 pages.
International Search Report and Written Opinion dated Apr. 20, 2017, issued in PCT Application No. PCT/US2016/068064, filed Dec. 21, 2016.

CONFIGURABLE FLUID MIXING SYSTEM HOUSING AND SUPPORT HARDWARE

CROSS-REFERENCE TO RELATED APPLICATIONS

This application claims priority to U.S. Provisional Application No. 62/712,343, filed Jul. 31, 2018, U.S. Provisional Application No. 62/670,934, filed May 14, 2018, and U.S. Provisional Application No. 62/618,215, filed on Jan. 17, 2018, which are both incorporated herein by specific reference.

BACKGROUND

The biopharmaceutical industry uses a broad range of mixing systems for a variety of processes such as in the preparation of media and buffers and in the growing, mixing and suspension of cells and microorganisms. Some conventional mixing systems, including bioreactors and fermentors, comprise large stainless steel chambers similar to those seen in breweries. Such systems necessitate large inputs of labor due to the cleanup required at the end of a run and still often suffer from contamination issues.

To reduce labor and increase sterility for sensitive operations, the industry has been moving toward single use systems which comprise a rigid housing supporting a flexible container often made from multi-layered polymers. The advantage is that instead of a using labor to sterilize the system at the end of a run the single use flexible container is simply thrown away and another put in its place. The use of single use systems has solved many historical issues and allowed for cheaper production of biologics and cell therapy drugs, however, additional issues were introduced.

Issues that have arose in the field of single use often involve installation of very large flexible containers along with connecting various peripheral attachments (e.g. tubes, sensors, and other equipment) as well as mounting a drive unit to a sterile bearing housing to drive impellers within the sterile flexible container.

Over the years, hoist systems have been produced to assist operators, but still require multiple operators to safely install a flexible container within the housing. For example, some systems require operators to affix the flexible containers to a hoist and raise them above the rigid housing so that the bag can then be lowered into the rigid housing. This effort often involves operators at the floor level to attach the hoist to the hoist and operators on a cat walk or platform at or above the top of the rigid housing to guide the installation process.

Additional issues arise in attaching peripherals. In many cases, operators have to first lower the flexible container into the rigid housing and then begin the process of attaching the various tubes and drive system while the flexible container which can involve operators having to reach into the rigid container and manipulate tubes, sensor assemblies, and drive components. Such work can be dangerous for the operator, require a substantial amount of time, and ultimately can lead to failures in the process being performed due to incomplete or faulty installations.

What is needed in the field of single use bioproduction is an installation system that provides safeguards to prevent operator injury as well as ensure successful installation with regard to flexible container alignment, peripheral attachment, and drive connection. Additionally, reducing the number of operators required to just one instead of many would result in a major cost savings. The method and system disclosed herein addresses all of these issues.

Another unaddressed issue in the field of single use bioproduction is the ability to modify systems to accommodate larger or smaller batch sizes. For example, the bioproduction field would see a cost savings if there was a system that started out at a given volume and once there was a need for additional capacity there was an option to increase a vessel volume with relative ease. The method and system disclosed herein addresses this issue.

Another unaddressed issue in the field of single use bioproduction is the ease with which connections from drive shafts to motors are made. Historically, a universal coupling or a flexible shaft coupler have been used. These couplings rely on a set screw or an index feature to retain the connection and do not readily support a tensile load. Face to face connections that are bolted together can support tensile loads, but suffer from their own drawbacks. What is needed is an easy to use coupling system that can support a tensile load. The method and system disclosed herein addresses this issue.

An issue referenced above is tube management. Mixers, bioreactors, and fermentors often require use of complex tube sets. Traditionally, operators have been left to determine where and how tubes are managed which creates inefficiencies in use of labor and the systems of methods for the processes involved. Some works arounds have been created in the field for tube management, but what is needed is a centralized and easily modifiable way to manage tube sets before the uses even opens the shipping package. The method and systems disclosed herein addresses this issue.

An issue referenced above is the difficulty in manipulating the flexible container into its proper orientation within the rigid housing structure. Historically, a spider lift mechanisms held the flexible container to the top of the housing while pegs at the bottom of the housing provided a place for the flexible container be secured. In all cases, operators were required for the attachment process which often involves having to reach into the back of the housing or stand on a ladder, cat walk, or other platform at the top of the rigid housing. What is needed is a system that can be managed by one person and doesn't require the user to stand over the rigid housing or have to reach into the back corners of the flexible housing. The method and system disclosed herein addresses this issue.

Another unaddressed issue relates to installation of a condenser. Condensers are commonly used in bioreactors because fluid evaporates and eventually condenses and needs to be recycled back into the system. Historically, condensers were situated at floor level and required tubes to be run from the top of the bioreactor or similar device and back down to the condense. Large diameter tube is required for these legacy systems and can increase costs substantially. What is needed is an easy way to install a condenser near the top of the rigid housing where the actual condensing is required. The method and system disclosed herein addresses this issue.

BRIEF SUMMARY

In one aspect, bioprocessing container installation system is disclosed. The system may include a rigid housing having an interior compartment and including a lift system, wherein the lift system includes cables secured to a framework, a flexible container disposed within the interior compartment, the flexible container including a plurality of connectors, and a moveable platform positioned over the flexible container and within the interior compartment and including a plurality of cable attachment devices and a plurality of securing devices, wherein the cables are operably connected to the cable attachment devices to suspend the moveable platform and the securing devices are operably connected to the connectors. In some embodiments, the flexible container may comprise a first surface having at least two adjoining connectors, a second surface having at least two adjoining connectors, and a sidewall joining the first and second surfaces, wherein a first bearing housing is mounted to the first surface and a second bearing housing is mounted to the second surface. In some embodiments, the rigid housing may further comprise at least two retractable cable assemblies mounted adjacent to a floor of the rigid housing, wherein the retractable cable assemblies include hooks for attaching to the at least two adjoining connectors of the second surface. In some embodiments, the flexible container may further include a plurality of ports joined to the second surface of the flexible container. In some embodiments, the bioprocessing installation system may further include a tube management plate having a plurality of openings to receive a plurality of tubes extending from the ports and a bearing receiver configured to receive and restrict movement of the second bearing housing relative to the tube management plate. In some embodiments, a floor of the rigid housing may include an opening bounded by a groove for receiving a perimeter edge of the tube management plate. In some embodiments, the moveable platform may further comprise a drive assembly mounted thereto, the drive assembly including a motor having a first bearing mount configured to receive the first bearing housing of the flexible container. In some embodiments, the bioprocessing container installation may further comprise a motive force device mounted to the exterior of the rigid housing, and a plurality of routing pulleys and suspension pulleys mounted to the framework, wherein the routing pulleys configured to direct the cables from the motive force device to the suspension pulleys and the suspension pulleys direct the cable to the cable attachment devices on the moveable platform. In some embodiments, the motive force device may include a pneumatic cylinder. In some embodiments, the moveable platform may further comprise a slack sensor assembly mounted thereto, comprising a spring loaded rod having a first end and a second end, wherein the spring loaded rod is configured to actuate from a first position to a second position when a force on the spring changes, a cable attachment affixed to the first end of the rod, wherein the cable attachment is configured to receive the cable, a bolt affixed to the second end of the rod, and a slack sensor configured to detect the position of the bolt. In some embodiments, the positional change of the bolt causes the slack sensor to send a signal to a controller to deactivate the motive force device. In some embodiments, the framework may further comprise a moveable platform securing assembly, comprising a protrusion receiver having a plurality of protrusion openings and configured to actuate between a first position and a second position, and an actuator mounted to both the moveable platform securing assembly and the protrusion receiver, the actuator configured to drive the protrusion receiver between the first and second positions. In some embodiments, a plurality of protrusions are mounted to the moveable platform, wherein the plurality of protrusions are configured to extend into the plurality of protrusion opens while the protrusion receiver is in the first position and become locked in place when the protrusion receiver actuates to the second position.

In one aspect, a bioprocessing container installation system is disclosed. In some embodiments, the bioprocessing container installation system may comprise a rigid housing having an interior compartment and including a lift system, a flexible container disposed within the interior compartment and including a connector, and a moveable platform positioned within the interior compartment and including an attachment device and a securing device, wherein the lift system is operably connected to the attachment device to position the moveable platform over the flexible container and the securing device is operably connected to the connector to suspend the flexible container from the moveable platform.

In one aspect, a method for installing a bioprocessing container within a bioproduction mixing system is disclosed. In some embodiments, the method for installing a bioprocessing container within a bioproduction mixing system may comprise providing a flexible container having a first surface, a second surface, and a sidewall joining the first and second surfaces, wherein a first bearing housing is mounted to the first surface and a second bearing housing and a plurality of tubes are mounted to the second surface, securing the second surface of the flexible container to a floor of a rigid housing, securing the first surface of the flexible container to a moveable platform within the rigid housing, and repositioning the moveable platform within the rigid housing. In some embodiments the method may further comprise the step of securing the second bearing housing to a bearing receiver on a tube management plate and securing the tubes to a plurality of openings on the tube management plate. In some embodiments the method may further comprise the step of positioning the tube management plate into an opening on the floor of the rigid housing. In some embodiments the method may further comprise the step of securing a perimeter edge of the tube management plate to a groove bounding the opening of the floor of the rigid housing. In some embodiments, the method further comprises the step of mounting the first bearing housing to a motor, wherein the motor is mounted to the moveable platform. In some embodiments, the method further comprises the step of repositioning the platform includes activating a motive force device, wherein the motive force device is operably connected to the moveable platform. In some embodiments, the method may include the step of securing the moveable platform to the rigid housing after the repositioning step. In some embodiments, the step of securing the moveable platform may further include activating a moveable platform securing assembly to restrict movement of a protrusion, wherein the moveable platform securing assembly is mounted to the rigid housing and the protrusion is mounted to the moveable platform.

In one aspect, a method for installing a bioprocessing container within a bioproduction mixing system is disclosed. In some embodiments, the method for installing a bioprocessing container within a bioproduction mixing system may include providing a flexible container having a first surface, a second surface, and a sidewall joining the first and second surfaces, securing the first surface of the flexible container to a moveable platform within a rigid housing, securing the second surface of the flexible container to a surface of the rigid housing, and repositioning the moveable platform within the rigid housing.

In one aspect, a bioprocessing container installation failsafe mechanism is disclosed. In some embodiments, the bioprocessing container installation failsafe mechanism may include a rigid housing including a door, wherein the door has an open configuration and a closed configuration, a catch assembly mounted to the rigid housing and configured to actuate between an open position and a closed position, wherein the door is physically inhibited from entering the closed configuration when the catch assembly is in the open position, and a flexible container having a surface adjoined to a sidewall and a bearing housing adjoined to and protruding from the surface, wherein the catch assembly enters the closed position through interaction with the bearing housing. In some embodiments, the catch assembly may comprises a catch plate having a protruding cam, and a cam plate having a cam guide that engages the protruding cam, wherein the cam plate moves between a first and a second position on a first axis and the catch plate moves between a first and second position and a second axis and the first positions of the plates correspond to the open position of the catch assembly and the second positions of the plates correspond to the closed position of the catch assembly. In some embodiments, the catch assembly may further comprise a spring loaded inhibitor plate, comprising a projection, a spring configured to extend the projection into an opening in the catch assembly, and a groove having an elongated region and a slot, wherein a dowel protruding from the cam plate engages the groove, wherein when the opening is unoccupied the dowel is restricted to the slot and the catch assembly stays in a closed position and when the opening is occupied by the bearing housing the inhibitor plate retracts and the dowel can enter the elongated region to close the catch assembly. In some embodiments, an arm may extend from the cam plate toward the door and when the cam is in the first position the arm physically inhibits the door from closing. In some embodiments, the arm may comprises a first end joined to the cam plate, a second end joined to a handle, a first recess that interacts with an arm guide when the catch assembly is open, and a second recess that interacts with an arm guide when the catch assembly is closed, wherein the arm guide includes a taper that restricts movement of the arm. In some embodiments, the rigid housing may include a floor having an opening bounded by a groove. In some embodiments, the container installation failsafe mechanism may further include a tube management plate having a perimeter edge and a bearing housing receiver configured to receive the bearing housing, wherein the perimeter edge abuts the groove.

In one aspect, a container installation failsafe method may comprising providing a flexible container having a surface, wherein a bearing housing is mounted to the surface, providing a rigid housing including a door and a surface having a catch assembly mounted thereto, wherein the catch assembly obstructs the door from closing, placing the bearing housing into the catch assembly and enabling removal of the obstruction, and removing an obstruction preventing the door from closing. In some embodiments, the catch assembly may comprises a catch plate having a protruding cam, and a cam plate having a cam guide that engages the protruding cam. In some embodiments, the method may further comprise the steps of moving the cam plate from a first position to a second position on a first axis, moving the catch plate from a first position to a second position on a second axis, and locking the bearing housing into an opening on the catch plate. In some embodiments, the obstruction is attached to the cam plate and the step of moving cam plate removes the obstruction from the door. In some embodiments, the obstruction is an arm extending away from the cam plate. In some embodiments, the method may further include the step of displacing an inhibitor plate through physical interaction with the bearing housing. In some embodiments, the inhibitor plate may comprise a projection, a spring configured to extend the projection into the opening, and a groove having an elongated region and a slot, wherein a dowel protruding from the cam plate engages the groove, wherein when the opening is unoccupied the dowel is restricted to the slot and the catch assembly remains in a closed position and when the opening is occupied by the bearing housing the inhibitor plate retracts and the dowel can enter the elongated region to close the catch assembly.

In one aspect, a peripherals management system for a single use bioproduction system is disclosed. The management system may comprise a rigid housing having a compartment bounded by a surface adjoined to a sidewall, wherein the surface includes a concave opening bounded by a groove, a flexible container disposed within the compartment and having a surface adjoined to a sidewall forming an interior, wherein a bearing housing protrudes from an exterior of the flexible container, a management plate including convex perimeter edge and a bearing receiver, the bearing receiver in physical communication with the bearing housing and the perimeter edge abutting and restrained by the groove. In some embodiments, the management plate may further include a plurality of openings and a plurality of tubes extend from the surface of the flexible container, wherein the tubes pass through and are restrained by the plurality of openings. In some embodiments, the management plate may further include a first plane and a second plane joined by a joining surface. In some embodiments, the management plate may further include a tab having an opening. In some embodiments, the management plate may further include a plurality of structural supports configured to withstand downward pressure from the flexible container.

In one aspect, a peripherals management system for a single use bioproduction system is disclosed. In some embodiments, the peripherals management system comprises a rigid housing having a compartment bounded by a surface adjoined to a sidewall, wherein the surface includes an opening bounded by a groove, a flexible container disposed within the compartment and having a surface adjoined to a sidewall forming an interior, wherein a tube extends from an exterior of the flexible container, a tube management plate including perimeter edge and an opening, the opening in physical communication with the tube and the perimeter edge abutting and restrained by the groove. In some embodiments, the tube management plate may further include a bearing receiver in physical communication with a bearing housing, the bearing housing protruding from the exterior of the flexible container. In some embodiments, the tube management plate may further include a first plane and a second plane joined by a sloped surface, wherein the bearing housing receiver is positioned on the second plane, a plurality of structure supports joined to a surface of the tube management plate for structural support, and a tab including an opening in physical communication with the first plane.

In one aspect, a method of managing peripherals extending from a bioprocessing container is disclosed. In some embodiments, the peripherals management method comprises providing a flexible container having a surface and an adjoining sidewall, wherein a plurality of tubes extend from the surface, inserting the tubes into openings on a tube management plate, and securing the tube management plate to the rigid housing. In some embodiments, the flexible container may include a bearing housing adjoined to the surface and the tube management plate includes a bearing receiver. In some embodiments, the method may further include the step of inserting the bearing housing into the bearing receiver. In some embodiments, the tube management plate may include a perimeter edge and the rigid housing includes a surface having an opening bounded by a groove. In some embodiments, the method may further include the step of inserting the perimeter edge of the tube management plate into the groove of the opening to secure the tube management plate to the rigid housing.

In one aspect, a bearing mount system for bioproduction is disclosed. In some embodiments, the bearing mount system may comprise a drive assembly including a drive unit and a bearing retention system mounted to the drive unit, a flexible container having a surface adjoined to a sidewall forming an interior, wherein a bearing housing protrudes from the surface of the flexible container and a drive shaft extends from the bearing housing, wherein the drive shaft removeably engages the drive unit and is positioned by the bearing retention system. In some embodiments, the bearing retention system may further comprise a retention plate having a first end, a second end, and an opening for receiving the bearing housing, and a swing arm having a first end and a second end, the first end pivotally attached to the first end of the retention plate and the swing arm configured to move between an open configuration and a closed configuration. In some embodiments, the swing arm may further include an opening and a spring loaded pin, the spring loaded pin is configured to engage a pin notch on the retention plate while in the closed configuration and restrict movement of the bearing housing. In some embodiments, the bearing retention system may further comprise a bearing clamp assembly including a handle pivotally mounted to the bearing retention system, a pivot portion having a first end and a second end, the first end pivotally attached to the handle and the second end pivotally attached to the retention plate, wherein the pivot portion moves from a first position to a second position to lift the drive shaft into a locking sleeve extending from the drive unit. In some embodiments, the bearing retention system may further comprise a locking sleeve for receiving and restricting movement of the drive shaft. In some embodiments, the locking sleeve may further comprise a receiver and a moveable collar positioned onto the receiver and configured to move between an open and a closed configuration, wherein the drive shaft is received in the open configuration and physically restrained in the closed configuration. In some embodiments, the receiver may further include a collar stop at a first end and a spring stop at a second end, wherein the moveable collar includes a first end and a second end, the first end abuts the collar stop in the closed configuration and the second end abuts a spring stop in the open configuration. In some embodiments, the locking sleeve may further include a spring secured within a recess on the moveable collar between a notch on the moveable collar and the spring stop on the receiver. In some embodiments, the system may further comprise a plurality of locking balls secured within a plurality of tapered openings on the receiver by the collar, wherein a depression on the collar allows movement of the locking balls within the tapered opening while in the open configuration, and wherein a sidewall on the collar restricts movement of the locking balls within the tapered opening while in the closed configuration and restricts movement of the drive shaft by engaging a recesses on the drive shaft.

In one aspect, a method for mounting a bearing assembly and drive shaft of a bioprocessing container to a drive unit is disclosed. In some embodiments, the method for mounting a bearing assembly and drive shaft may include providing a flexible container having a surface and an adjoining sidewall, wherein a bearing housing is mounted to the surface and a drive shaft extends from the bearing housing, positioning the bearing housing and drive shaft into a retention assembly, and securing the bearing housing and drive shaft to the retention assembly. In some embodiments, the retention assembly may include a retention plate having a first end, a second end, and an opening for receiving the bearing housing, and a swing arm having a first end and a second end, the first end pivotally attached to the first end of the retention plate and the swing arm configured to move between an open configuration and a closed configuration. In some embodiments, the method may further comprise the steps of positioning the bearing housing into the opening of the retention plate, closing the swing arm to restrict movement of the bearing housing, and securing the swing arm to the retention plate. In some embodiments, the retention assembly may include a clamp assembly comprising a handle pivotally mounted to the retention system, and a pivot portion having a first end and a second end, the first end pivotally attached to the handle and the second end pivotally attached to the retention plate. In some embodiments, the method may further include the steps of actuating the handle and locking the drive shaft into a locking sleeve, wherein the locking sleeve is secured to the motor. In some embodiments, the locking sleeve may include a receiver and a moveable collar positioned onto the receiver. In some embodiments, the method may further comprise the steps of moving the collar to an open position to receive the drive shaft and Moving the collar to a closed position to physically restrain the drive shaft.

In one aspect, a cable slack line detection system is disclosed. In some embodiments, a cable slack line detection system may comprise a sensor mounted to a bracket, a spring loaded rod mounted between the bracket and a plate, wherein the rod has a first end and a second end, a bolt affixed to the first end of the rod, and an attachment affixed to the second end of the rod, wherein when a force is applied to the attachment, the bolt moves from a first position to a second position and the sensor detects the position of the bolt. In some embodiments, the attachment includes a cable opening for receiving a cable, wherein the cable is secured to the cable opening by a pin. In some embodiments, the bracket is secured to a moveable platform and the moveable platform is suspended by the cable. In some embodiments, the moveable platform is prevented from moving when the force is decreased due to a slack in the cable and a positional change is detected in the bolt.

In one aspect, a cable slack line detection system is disclosed. In some embodiments, the cable slack line detection system may include an attachment for interacting with a cable and a sensor positioned to detect a locational change in the attachment, wherein when a tension on the cable changes the attachment changes locations.

In one aspect, a method of detecting slack in a bioproduction hoist assembly is disclosed. In some embodiments the method comprises suspending a platform within an interior of a rigid housing using a cable secured to the platform and a lift system, detecting slack in the cable using a detection system, and preventing movement of the platform. In some embodiments, the detection system may include a sensor mounted to a bracket, a spring loaded rod mounted between the bracket and a plate, wherein the rod has a first end and a second end, a bolt affixed to the first end of the rod, and an attachment affixed to the second end of the rod, wherein when a force is applied to the attachment, the bolt moves from a first position to a second position and the sensor detects the position of the bolt. In some embodiments, the method may further comprise the step of deactivating the lift system.

In one aspect, a bioproduction mixing system is disclosed. In some embodiments, the bioproduction mixing system may include an expander having a sidewall surrounding an interior and a first edge and a second edge, a lift support mounted to the first edge of the expander, and a base having a sidewall and a floor forming part of the interior, an edge of the sidewall of the base mounted to the second edge of the expander. In some embodiments, the lift support may further include a framework with legs having a first end and second end, the second end is in physical communication with the first edge of the expander and a beam mounted to the first end. In some embodiments, a pulley system is affixed to the beam, the pulley system includes pulleys and cables and suspends a moveable platform within the interior. In some embodiments, a flexible container is supported by the moveable platform within the interior. In some embodiments, the combined expander, lift support, and base form a rigid housing, the rigid housing may comprise a motor is affixed to an exterior of the rigid housing, wherein a first end of the cable is secured to the motor and the pulley system directs a second end of the cable to an attachment point on the moveable platform. In some embodiments, a control system is in electronic communication with the motor.

In one aspect, a method for expanding the volume of a single use bioproduction mixing system is disclosed. In some embodiments, the method may include the steps of providing a base having a sidewall and a floor forming part of and interior, mounting a lift support to the sidewall of the base, dismounting the lift support from the sidewall of the base, mounting an edge of a sidewall of an expander unit to the base, and mounting a lift support to an opposing edge of the expander.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Embodiments of systems, methods, and apparatuses for cell culture are described in the accompanying description and figures. In the figures, numerous specific details are set forth to provide a thorough understanding of certain embodiments. A skilled artisan will be able to appreciate that the fluid or cell culture media mixing system described herein may be used for a variety of applications including, but not limited to, buffer creation, media rehydration, cell culture, viral inactivation, and fermentation. Additionally, the skilled artisan will appreciate that certain embodiments may be practiced without these specific details. Furthermore, one skilled in the art will readily appreciate that the specific sequences in which methods are presented and performed are illustrative and it is contemplated that the sequences may be varied and still remain within the spirit and scope of certain embodiments.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Furthermore, in described various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequence may be varied and still remain within the spirit and scope of the various embodiments.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Figure 1:
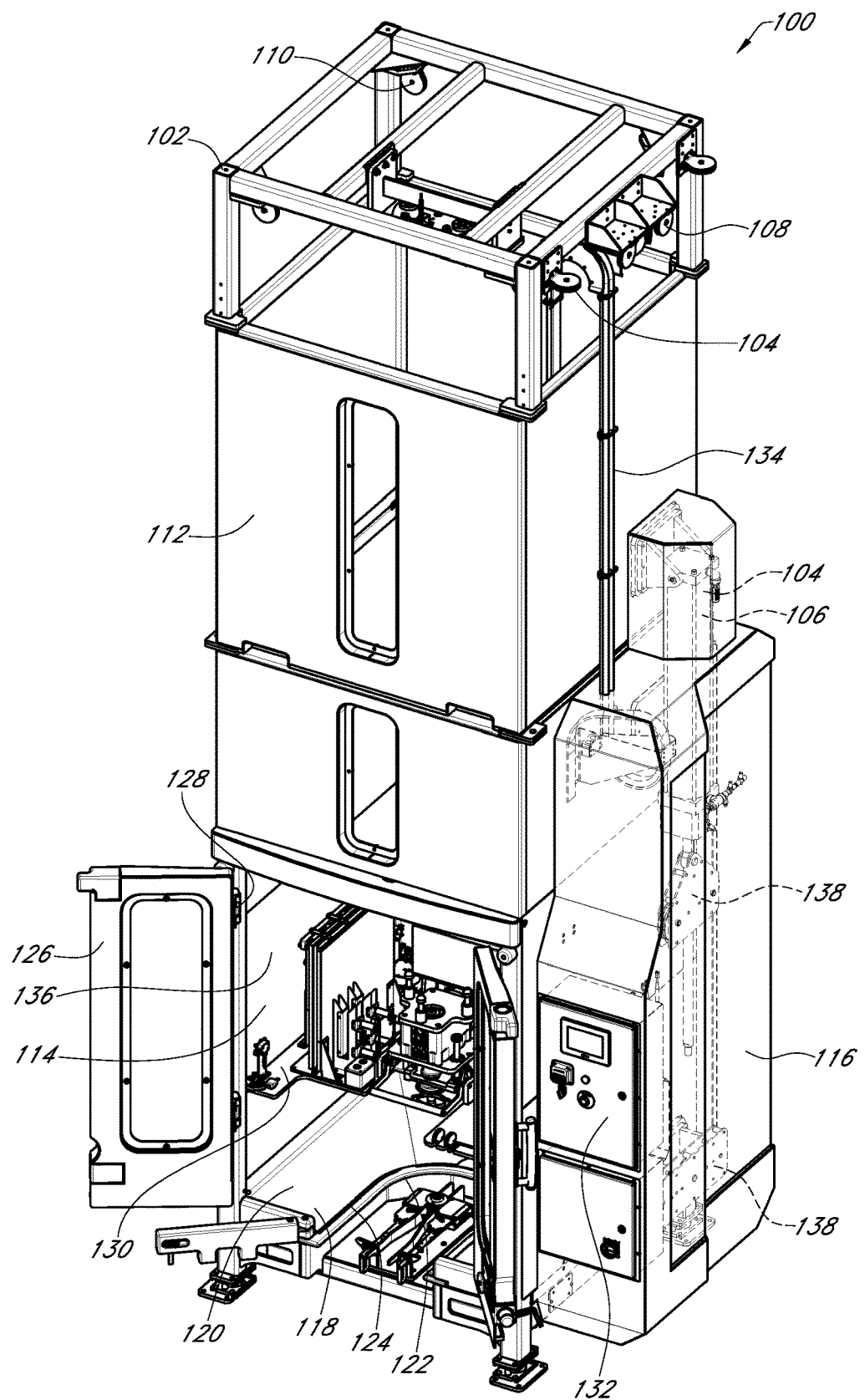
FIG. 1 illustrates a rigid housing 100 in accordance with one embodiment.
Figure 2:
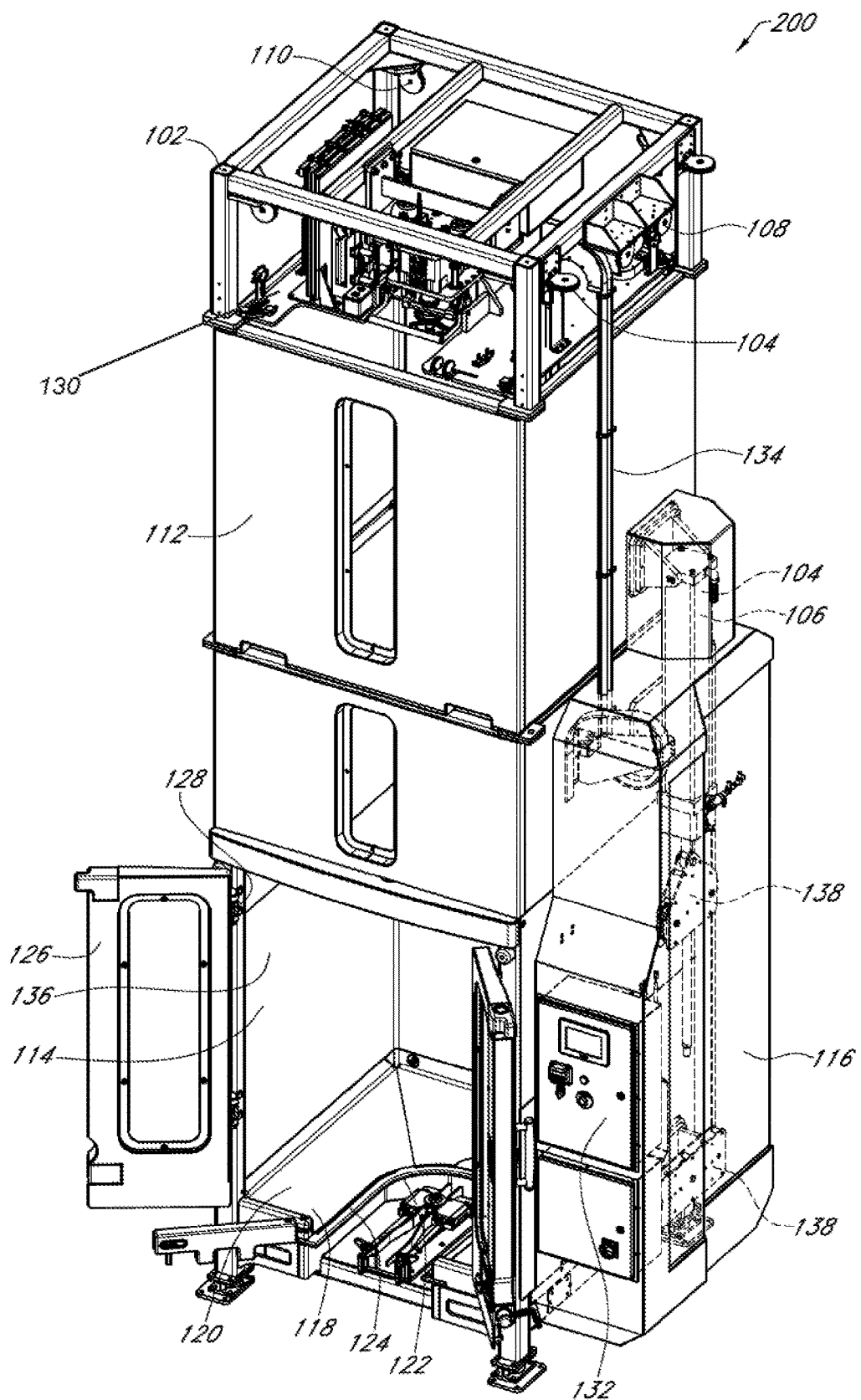
FIG. 2 illustrates a rigid housing 200 in accordance with one embodiment.

FIGS. 1 and 2 illustrate an embodiment of a rigid housing 100 comprising a framework 102, expander 112, and base 116 adhered to one another through bolts, welds, or any method of attachment known in the art. In some embodiments, the rigid housing 100 may act to provide support for a flexible container (see FIG. 6). In such embodiments, a pre-sterilized flexible container may be installed within the rigid housing 100 for use in a bioproduction process such as cell culture. Once the process is complete the flexible container may be removed and replaced. In various embodiments, the rigid housing 100 is reuseable.

In various embodiments the framework 102 of the rigid housing 100 may provide a structure to which a lift system 104 may be mounted in whole or in part. The lift system 104 may include a motive force device 106 operably connected to a pulley system. Cables may run from the motive force device 106 to a set of routing pulleys 108 which may then be directed to suspension pulleys 110. The suspension pulleys 110 may then direct the cables (see FIG. 16) to the moveable platform 130 where they may attach. The embodiment disclosed above may allow for movement of the moveable platform 130 within the rigid housing 100 and, thereby, allow for installation of a flexible container. FIG. 1 illustrates the moveable platform 130 positioned near the floor 118 and FIG. 2 illustrates the moveable platform 130 positioned in close proximity to the framework 102 at the top of the rigid housing 100. In FIG. 1 an operator may attach a flexible container to the moveable platform 130 and to a position near or on the surface 120 of the floor 118 of the rigid housing 100. The operator may then interact with an HMI 132 to raise the moveable platform 130 to a position as seen in FIG. 2. In some embodiments, the moveable platform 130 location depicted in FIG. 2 is situated in an installed configuration (flexible container not shown in FIG. 1 or 2).

In various embodiments, an expander 112 is positioned between the framework 102 and the base 116 portions of the rigid housing 100. The expander 112 may vary in height and be attached or detached from the rigid housing 100 depending on the volume desired for a given process. Various components may be mounted to the expander 112 such as a power cable 134 for powering various components on the moveable platform 130 or elsewhere in the system. In some embodiments, the motive force device 106 may optionally be affixed to the expander 112 portion as well. In some embodiments, the power cable 134 may be affixed or positioned anywhere on the rigid housing 100 through an adhesion method known in the art.

In various embodiments, the base 116 unit may be mounted to the expander 112 or the framework 102 depending on the desired system volume. In some embodiments, the base 116 may include a floor 118 having a surface 120 and a concave opening 122 that may be bounded by a groove 124. In some embodiments, the surface 120 of the floor 118 may be affixed to a sidewall 114 through a variety of attachment means including, but no limited to, bolting or welding. In various embodiments, the base 116 may include a door 126 having a set of hinges 128 allowing insertion of a flexible container within the rigid housing 100. In various embodiments, the rigid housing 100 may include an interior compartment 136 that may extend into the expander 112 and may further extend into the framework 102.

In various embodiments, a computer or HMI 132 can be mounted to the rigid housing 100 and may control various operations of the bioproduction process, including, installation of the flexible compartment through control of the motive force device 106. The HMI 132 may further control various aspects of the bioprocess through electronic communication to the various components on the moveable platform 130 that are in direct contact (electronically, fluidically, or otherwise) with the environment of the flexible compartment.

In various embodiments, the lift system 104 may be any system that enables movement of the moveable platform 130. In some embodiments, the moveable platform 130 may include a motor having teeth that interact with a track mounted to the interior of the rigid housing 100. In other embodiments, the moveable platform 130 may rely on magnetic a motive force device 106 positioned either external or internal to the rigid housing 100.

Figure 3:
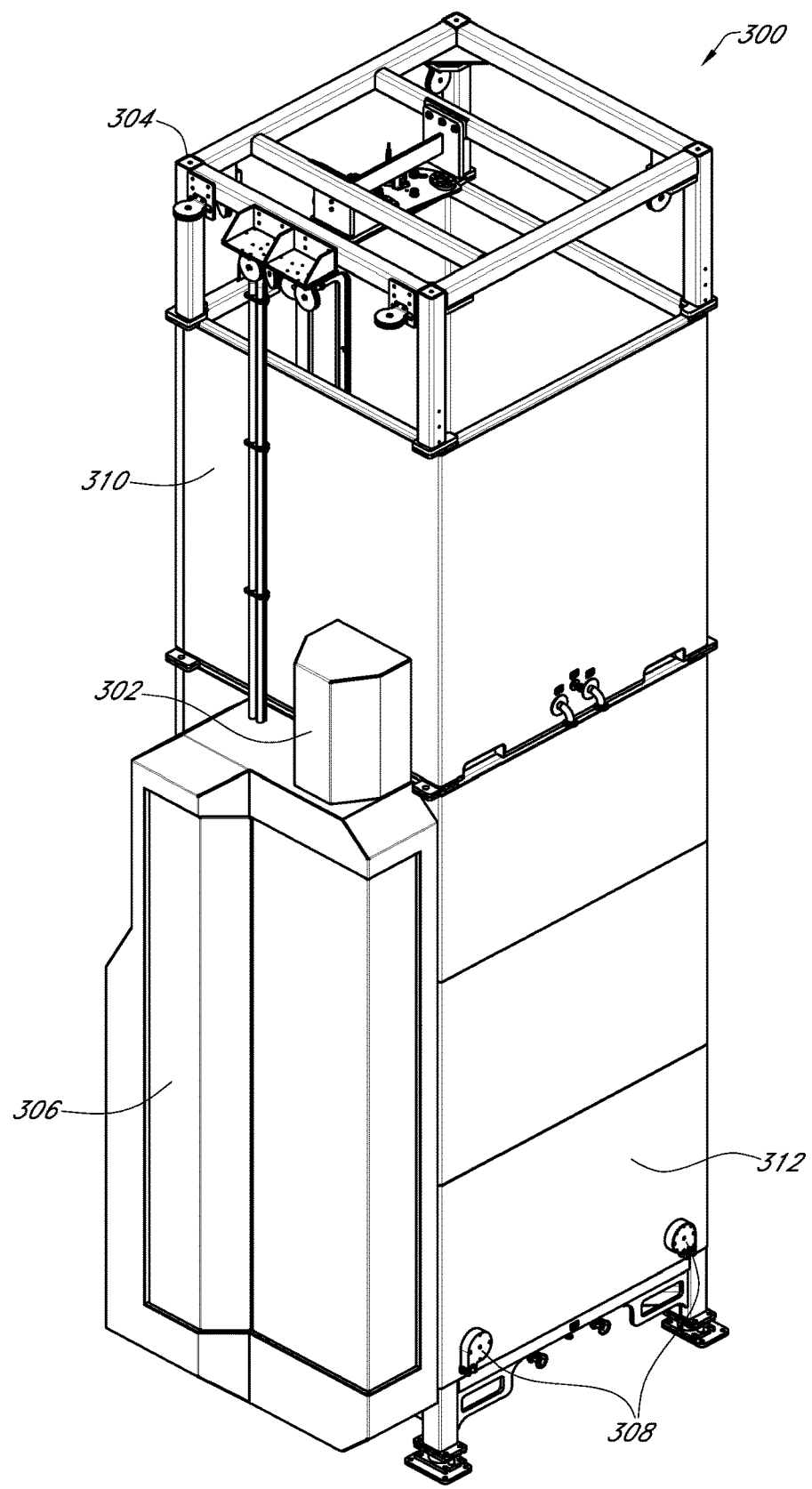
FIG. 3 illustrates a rigid housing 300 in accordance with one embodiment.

FIG. 3 illustrates an embodiment of a rigid housing 300 from a rear perspective view comprising a framework 304, expander 310, and base 312. In various embodiments, a motive force device housing 302 may be mounted to the rigid housing 300 for housing the motive force device 106. In various embodiments a component housing 306 may house the HMI 132 as well as components of the lift system 104. In various embodiments, retractable cable assemblies 308 may be mounted to the rigid housing 300. In some embodiments, the retractable cable assemblies 308 may be mounted on the rear of the base 312 and may interact with a flexible container within the interior compartment 136 through openings in the rigid housing 300. In other embodiments, the retractable cable assemblies 308 may be mounted in the interior compartment 136 of the rigid housing 300 or anywhere else that allows for operably attachment to a flexible container within the rigid housing 300.

Figure 4:
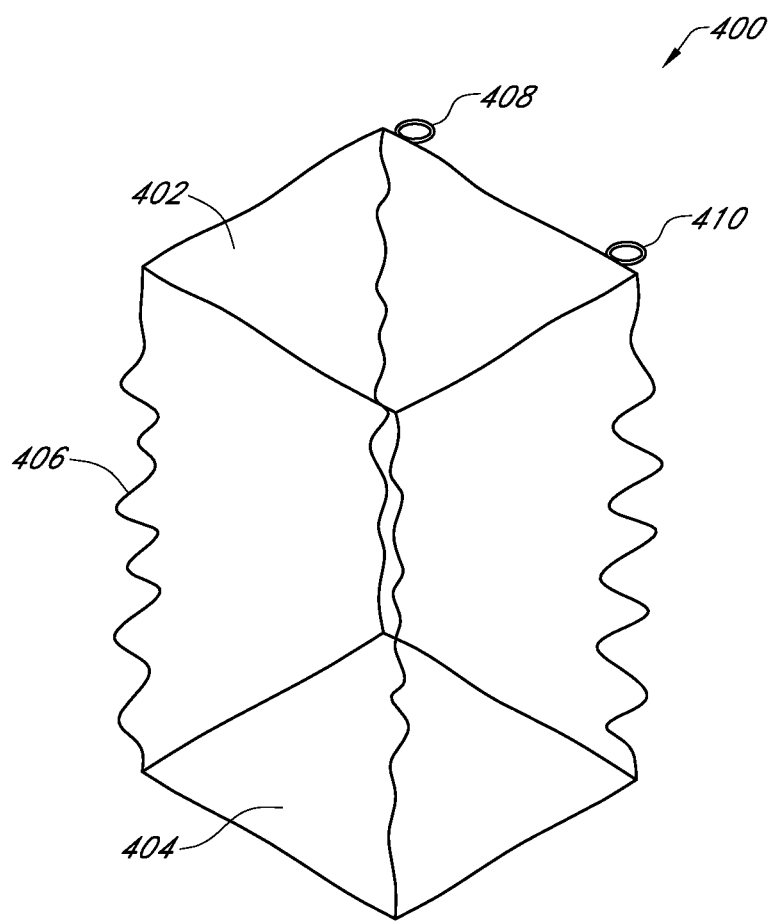
FIG. 4 illustrates a flexible container 400 in accordance with one embodiment.
Figure 6:
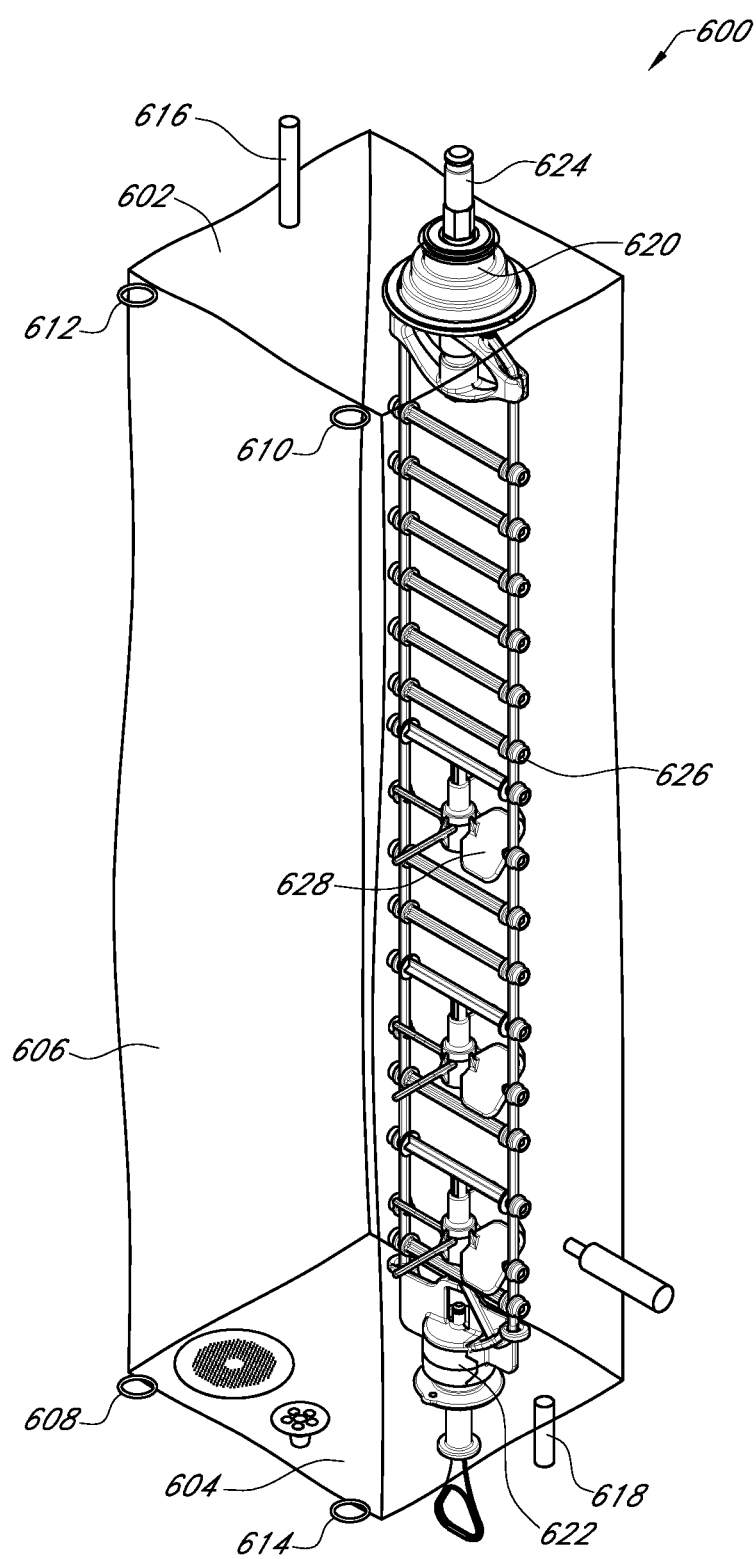
FIG. 6 illustrates a flexible container 600 in accordance with one embodiment.

FIG. 4 illustrates an embodiment of a flexible container 400 in a collapsed or packaged configuration comprising a first surface 402 and a second surface 404 joined a sidewall 406. Affixed near or adjacent to one or both of the surfaces are connectors 408, 410. Joined to the first surface 402 is a first bearing housing 620 (Fig. 6) and joined to the second surface 404 is a second bearing housing 622(Fig. 6). The bearing housings 620, 622 support a helical drive assembly 626 (Fig. 6) mounted between them.

An advantage to single use bioprocessing systems is the ability to package single use containers (flexible container 400) into small packages and later install and inflate them once placed inside a rigid housing 100, 200, 300. In various embodiments, the flexible container 400 may be placed into a rigid housing 100, 200, 300 while the doors of the rigid housing 100, 200, 300 are in an open configuration. The first bearing housing 620 may be operably connected to the moveable platform 130 and the second bearing housing 622 may be positioned at or near the floor 118 of the rigid housing 100, 200, 300. In some embodiments, the retractable cable assemblies 308 may be connected to connector 408, 410 at or near the second surface 404 of the flexible container 400. In some embodiments, the moveable platform 130 may then be repositioned closer to the framework 102 as seen in FIG. 2 which situates the flexible container 400 into a ready to use position. In some embodiments, a final installation step may be to inflate the flexible container 400 once properly positioned.

In various embodiments, the connectors 408, 410 can be loops or hooks welded, adhered, or clipped to the flexible container 400 and designed to interact in some way with the rigid housing 100, 200, 300 to position the flexible container 400 within the interior compartment 136 of the rigid housing 100, 200, 300. In some embodiments, the retractable cable assemblies 308 may be placed or attached anywhere on or within the rigid housing 100, 200, 300 and may comprise hooks attached to a spring loaded cable, string, or other elongated securing element. In some embodiments, the retractable cable assemblies 308 may be simple hooks.

In various embodiments, the bear housings 620, 622 may be any device that is affixed or adhered to the flexible container 400 that allows transfer of rotational force from the exterior of the flexible container 400 to the helical drive assembly 416 within the flexible container 400. In some embodiments, the helical drive assembly 626 may extend from the first surface 402 to the second surface 404 of the flexible container 400. In some embodiments, the helical drive assembly 626 may include one, two, three, or more drive lines running in parallel and configured to attach to impellers and stabilizing units. In some embodiments, the helical drive assembly 626 may be a simple drive shaft connected to one or both surfaces through one or both bearing housings 620, 622.

Figure 5:
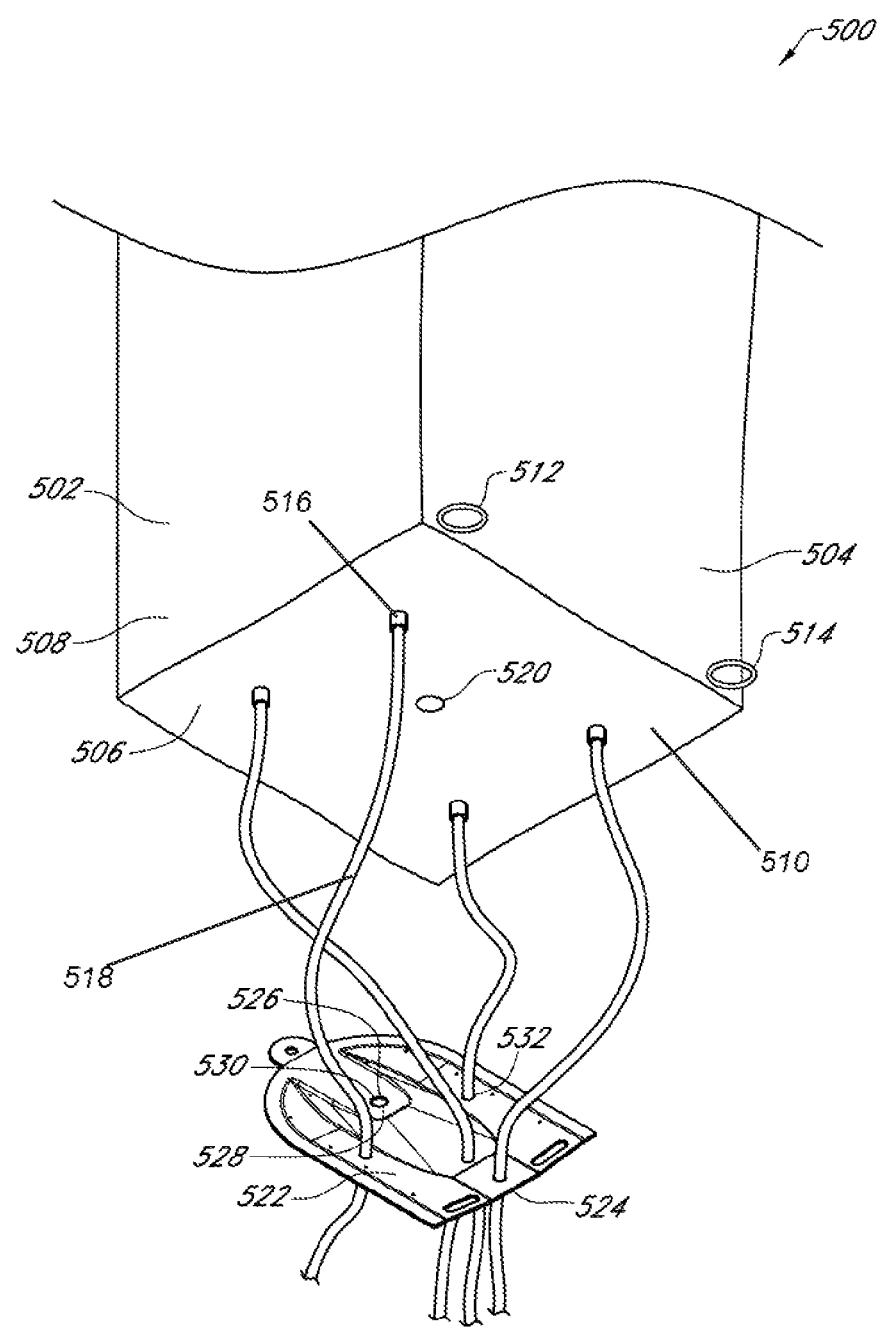
FIG. 5 illustrates a peripheral management assembly 500 in accordance with one embodiment.

FIG. 5 illustrates an embodiment of a peripheral management assembly 500 comprising a flexible container 502 and a tube management plate 522.

In various embodiments, the flexible container 502 may include a sidewall 504 joined to a second surface 506 forming an interior 508. In some embodiments, the second surface 506 may include an exterior 510 to which a plurality of ports 516 may extend. In some embodiments, the port 516 structures may be welded, adhered, or attached in any way known or use in the art to the second surface 506 or anywhere else on the flexible container 502. In some embodiments, a bearing housing 520 may also extend from the second surface 506 of the flexible container 502 for providing rotational movement to a helical drive assembly 626. In some embodiments, tubes 518, sensor probes (not shown), or any other peripheral device may in optical, electrical, fluidic, or any other kind of communication with the interior 508 of the flexible container 502 through the plurality of ports 516. In some embodiments, tubes 518 will extend away from the ports 516.

In various embodiments a tube management plate 522 may include a plurality of openings 532 and a bearing receiver 526 that are bounded by a perimeter edge 524 of the tube management plate 522.

In various embodiments, the plurality of openings 532 are configured to accept the plurality of ports 516 or tubes 518 and physically restrain them within the openings 532. In some embodiments, restraint occurs through friction or use of a clip (not shown) and in other embodiments the tubes 518 may float freely along their elongated axis within the openings 532.

In various embodiments, the bearing receiver 526 may be a simple opening for receiving the bearing housing 520 projecting from the second surface 506 of the flexible container 502. In some embodiments, the bearing receiver 526 may include an opening having a narrow portion 528 and a broad portion 530. In some embodiments, the broad portion 530 may accept the bearing housing 520 and the bearing housing 520 can slide relative to the tube management plate 522 to enter the narrow portion 528 which may then physically restrict movement of the flexible container 502 and tube management plate 522 relative to one another through frictional forces.

In various embodiments, the tube management plate 522 offers a unique and simplified way to organize a complex set of attachments extending from a flexible container 502. Historically, an operator would be required to adjust tube and bearing locations one by one which could be labor intensive and result in a disorganized system. The embodiment illustrated in FIG. 5 allows for simple arrangement of peripherals that can be managed with a small amount of labor. In some embodiments, the tube management plate 522 and flexible container 502 combination can be shipped in a pre-configured manner so that the end user need only slide the entire assembly into a rigid housing 100, 200, 300 for installation. In some embodiments, an end user can order a custom or off the shelf tube set which can then be pre-organized onto a custom or standardized tube management plate 522 and then shipped for use.

FIG. 6 illustrates and embodiment of a flexible container 600 comprising a first surface 602 and a second surface 604 joined by a sidewall 606. In various embodiments, a plurality of connectors 608, 610, 612, 614 may be assembled onto one of the surfaces 602, 604 or onto the sidewall 606 for positioning the flexible container 600 into a rigid housing 100, 200, 300. In some embodiments, the connectors 608, 610, 612, 614 may be hooks, adhesive, magnets, pins, loops or anything else capable of forming an attachment and may be connected to the same or a similar element affixed or adhered to the rigid housing 100, 200, 300. In some embodiments, the flexible container 600 may further include ports 616, 618 welded, adhered, or attached in some other way to any part of the flexible container 600. In some embodiments, a first bearing housing 620 may be welded or adhered to the first surface 602 of the flexible container 600 and a second bearing housing 622 may be welded or adhered to the second surface 604 of the flexible container 600 for supporting rotational movement of a drive assembly 626. In some embodiments a drive shaft 624 extending away from the first second bearing housing 622 may interactor with a motor (see FIG. 26) to provide rotational movement to the drive assembly 626 within the interior portion of the flexible container 600. In some embodiments, the drive assembly 626 may include one or more impellers 628 for mixing a fluid within the flexible container 600.

Figure 7:
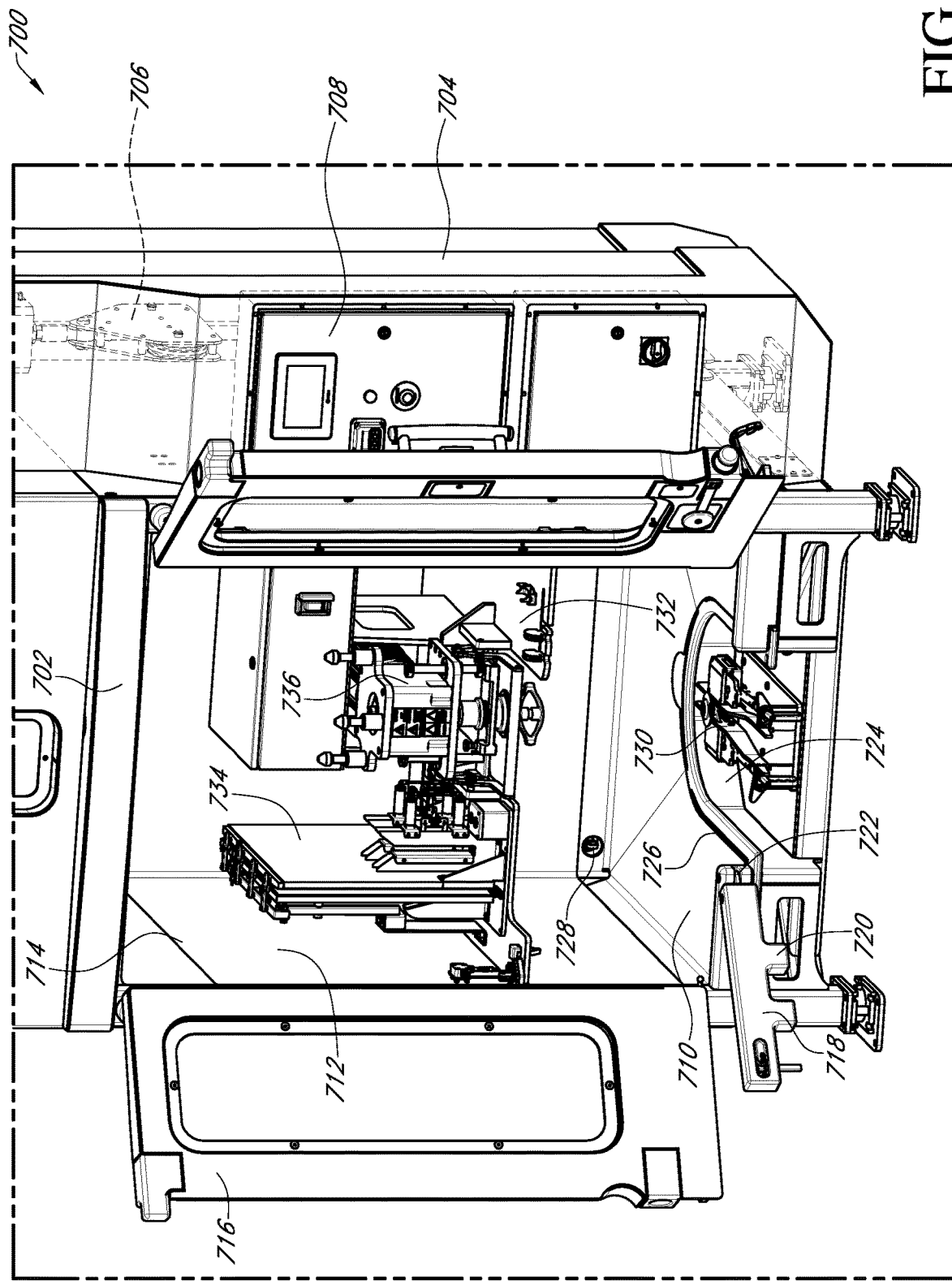
FIG. 7 illustrates a base 700 in accordance with one embodiment.

FIG. 7 illustrates an embodiment of a base 700 unit and an exterior housing 704 forming a portion of a rigid housing 702.

In various embodiments, the exterior housing 704 may separate or part of the rigid housing 702 having its own interior for housing a variety of different components. In some embodiments, those components may include a control system 708 and a portion of a lift system 706 including pulleys cable attachments and other connection and attachment devices designed to move the moveable platform 732 within the interior 714 of the rigid housing 702. In some embodiments, the control system 708 or HMI 132 is in electronic communication with the lift system 104, 706 and may direct movement of the moveable platform 130, 732. In some embodiments, the control system 708 may have a user interface for an operator to direct control over the moveable platform 130, 732 or control may be automated. In some embodiments, the exterior housing 704 may be welded or bolted to the rigid housing 702 in a fixed manner or may be its own separate unit.

In various embodiments, the base 700 of the rigid housing 702 may comprise a sidewall 712 mounted by weld or bolts to a floor 710 to create an interior 714 where a moveable platform 732 may reside. In various embodiments, there may be a cable opening 728 in the floor 710 of the base 700 of the rigid housing 702. A concave opening 724 extends through floor 710 and is bounded by a groove 726. In some embodiments the tube management plate 522 seen in FIG. 5 and throughout the Figures and description is designed to fit into the opening. Specifincally, in some embodiments, the perimeter edge 524 of the tube management plate 522 may include a convex portion that is configured to fit into a concave opening 724 within the groove 726 wherein the movement of the tube management plate 522 is thereby restrict due to frictional forces. In some embodiments additional restriction devices may be used including weld or adhesion or in some cases a swing 718 arm may be moved and locked into a position that prohibits the tube management plate 522 from exiting the opening 724. In such embodiments, the restriction of the tube management plate 522 also restricts the movement of the flexible container 400, 502, 600 due to the tube management plate 522 being mounted to the flexible container 400, 502, 600.

In various embodiments, the base 700 unit includes a door 716 mounted to hinges 722 which may close after the flexible container 400, 502, 600 has been properly installed into the rigid housing 702. In some embodiments, a catch assembly 730 may be mounted to the floor 710 or somewhere within the opening 724 of the rigid housing 702. In some embodiments, the catch assembly 730 may be configured to receive the second bearing housing 520, 622 and restrict its movement once it is located in its proper configuration. In some embodiments, the swing 718 will not close properly unless the second bearing housing 520, 622 is properly oriented within the catch assembly 730. In some embodiments, a blocking portion 720 of the swing 718 or door 716 may interact with the catch assembly 730 to prevent closing of the door 716 or swing 718.

In various embodiments, the sidewall 712 or floor 710 of the rigid housing 702 may include one or more cable openings 728 that allow retractable cable assemblies 308 positioned on the exterior of the rigid housing 702 to interact with the flexible container 400, 502, 600 contained within the interior 714 of the rigid housing 702. In some embodiments, hooks, latches, or connecting devices can engage connectors on the flexible container 600 and then retract in a manner that will prevent them from damaging the flexible container 400, 502, 600 after installation is complete. In some cases, having hooks or protruding objects remaining within the interior 714 of the rigid housing 702 may cause damage to flexible containers through physical interaction.

In various embodiments, a flexible container 400, 502, 600 may be positioned between the floor 710 and the moveable platform 732 within the rigid housing 702 for installation. In some embodiments, the first bearing housing 620 may operably couple to the moveable platform 732 by connecting to the drive assembly 736. In some embodiments, the first port 616 or tubes may interact with a condenser 734 and the condenser 734 may be mounted to the moveable platform 732 or simply rest on the moveable platform 732. In some embodiments, the second bearing housing 622 may insert and attach to the catch assembly 730. Once the connections from the flexible container 400, 502, 600 have been made to the moveable platform 732 and the catch assembly 730 and other portions of the rigid housing 702 the moveable platform 732 may be raised to the position shown in FIG. 2 before beginning a bioproduction process.

Figure 8:
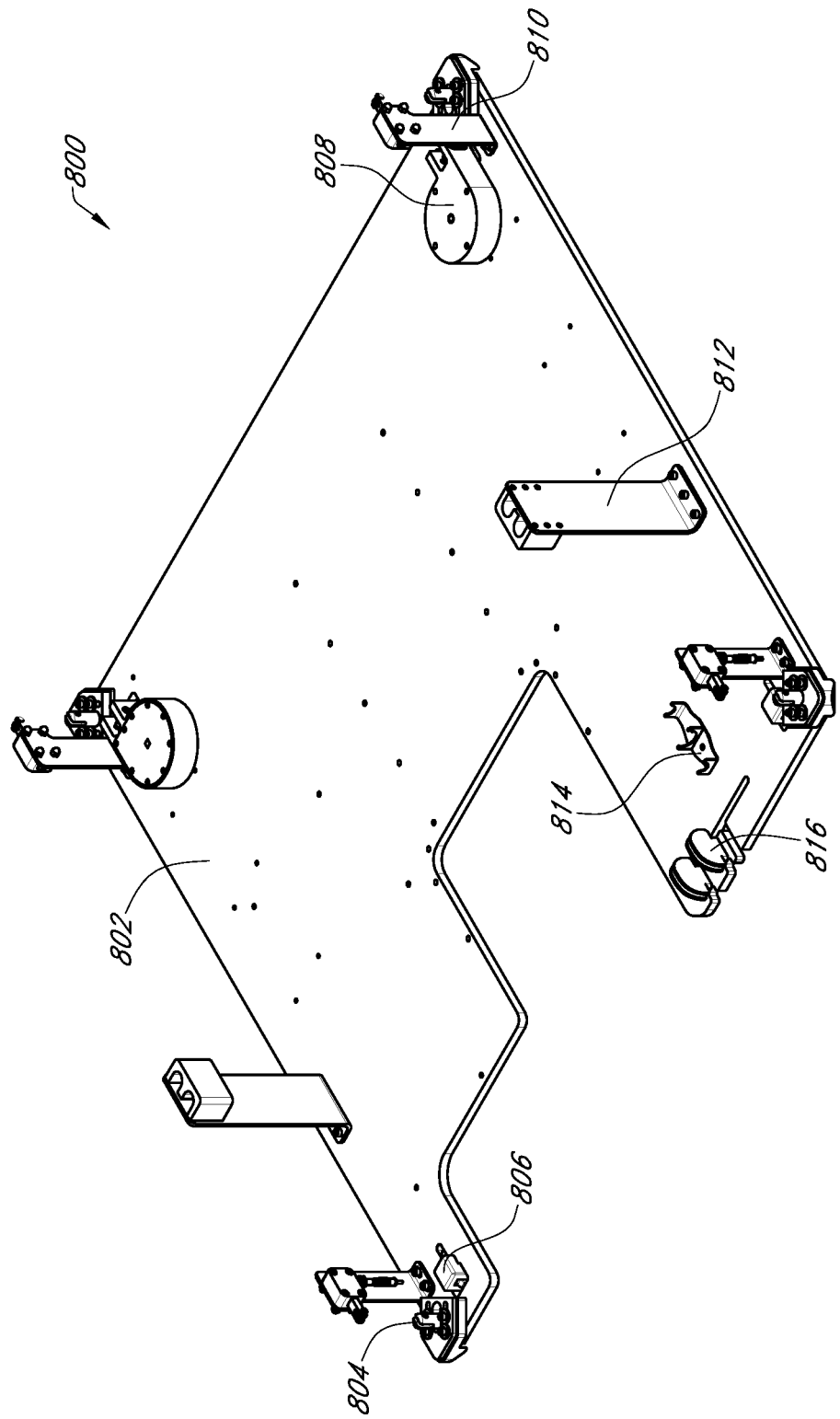
FIG. 8 illustrates a moveable platform 800 in accordance with one embodiment.
Figure 9:
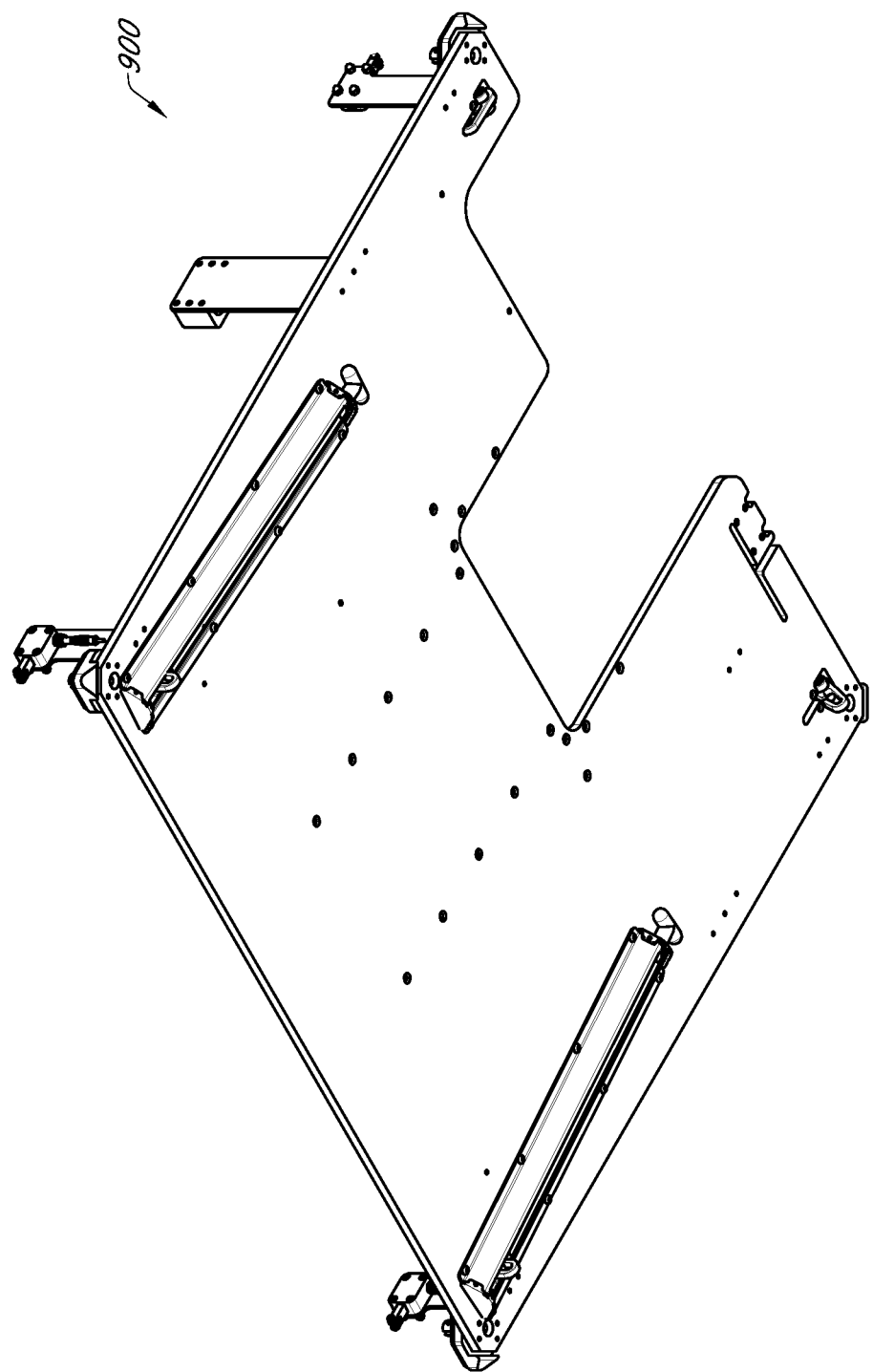
FIG. 9 illustrates a moveable platform 900 in accordance with one embodiment.

FIG. 8 illustrates an embodiment of a moveable platform 800 comprising a top surface 802 including a cable attachment device 804, a securing device 806, a retractable cable assembly 808, a cable slack sensor assembly 810, a cable track clamp 812, a filter bracket 814, and a tube holder 816 attached thereto. In various embodiments, the components residing on the top surface 802 of the moveable platform 800 may be welded, screwed in place, bolted, or attached in any other way that is known or useful in the art. In some embodiments, the moveable platform 800 may include a plurality of openings in which pins or screws can attach. Such a system may allow a variety of components to be configured in any desirable arrangement depending on the application. FIG. 9 illustrates the same embodiment of the moveable platform as illustrated in FIG. 8 from the underside.

Figure 10:
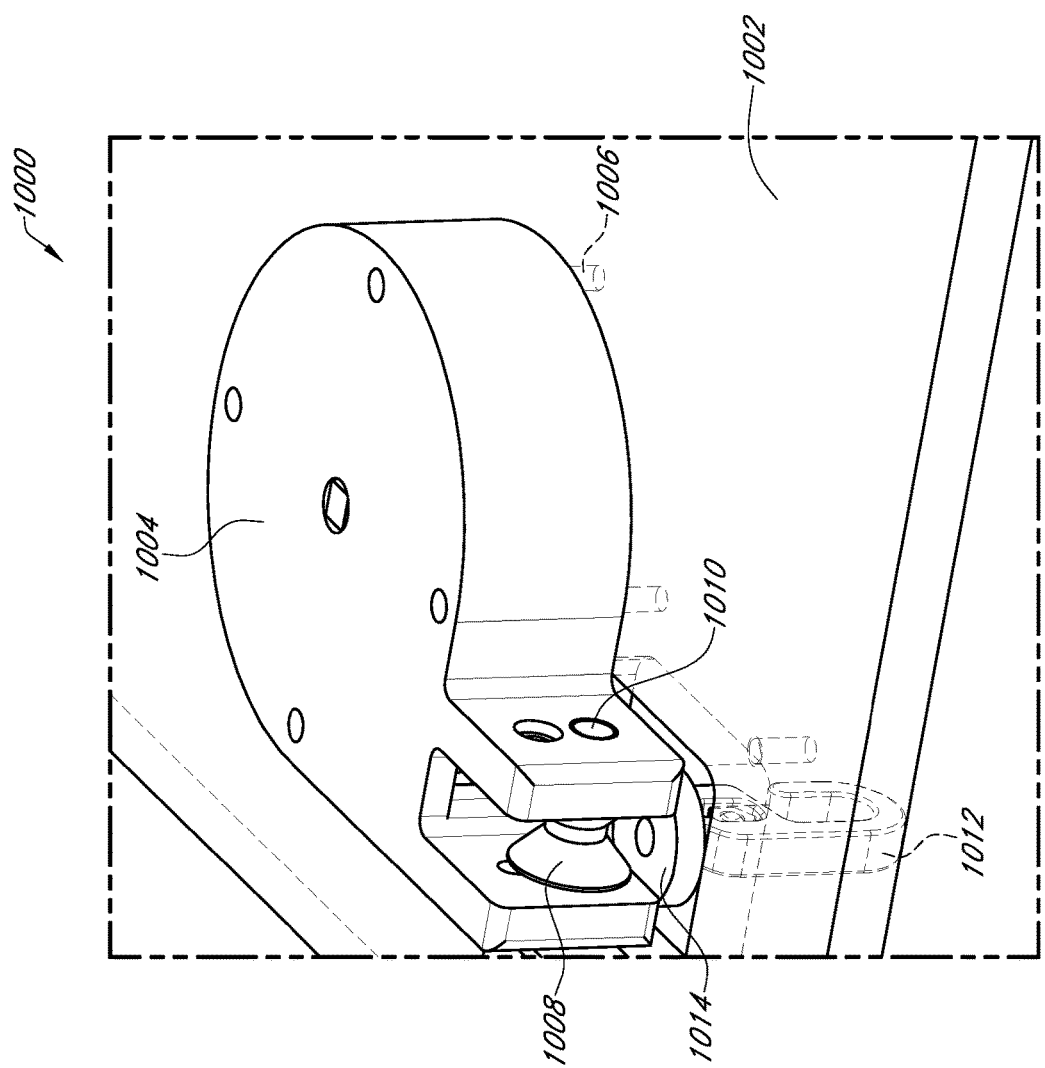
FIG. 10 illustrates a retractable cable assembly 1000 in accordance with one embodiment.
Figure 11:
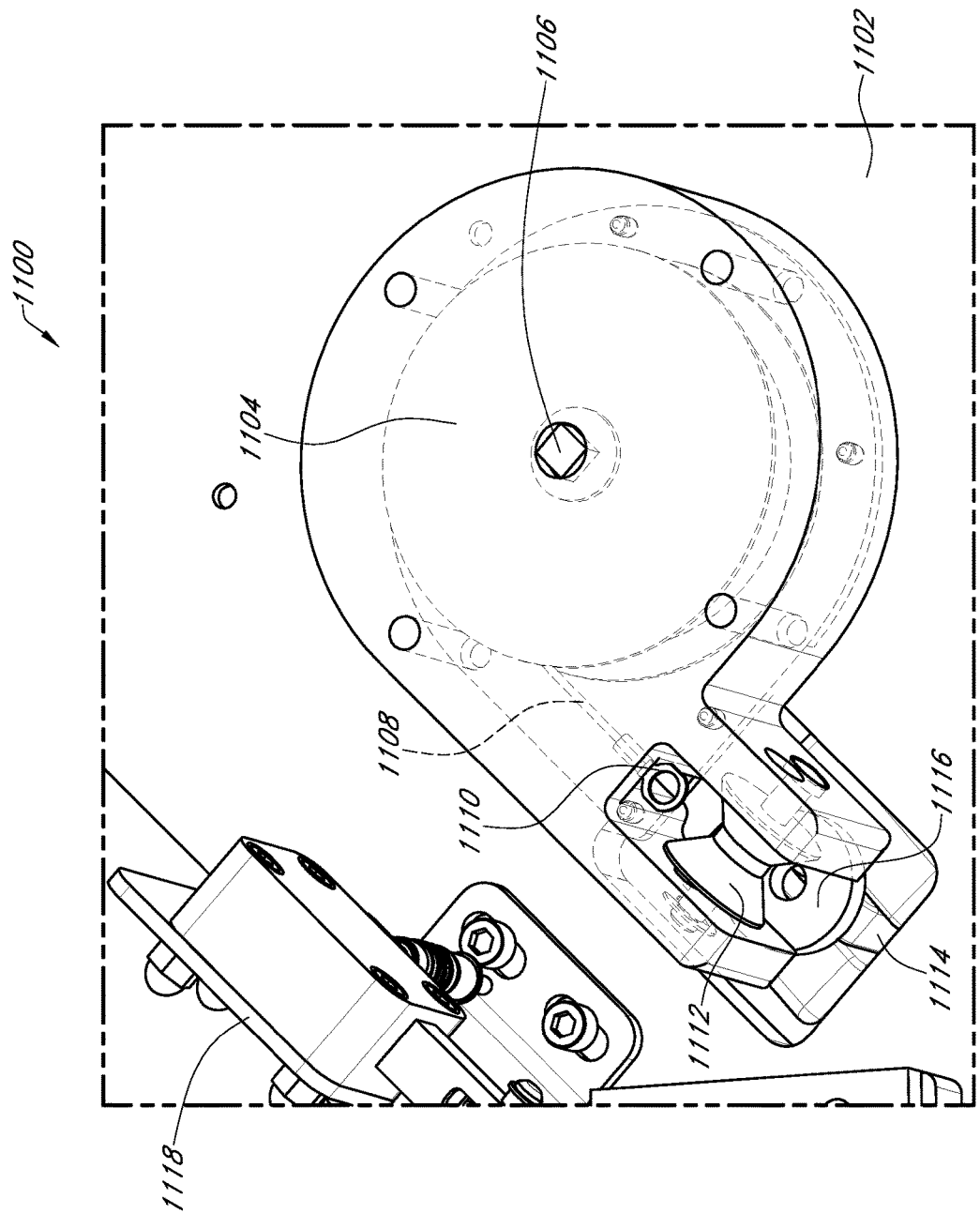
FIG. 11 illustrates a retractable cable assembly 1100 in accordance with one embodiment.

FIGS. 10 and 11 illustrate an embodiment of a retractable cable assembly 1000, 1100 or securing device. General embodiments of a retractable cable assembly 1000, 1100 may be anything that allows a connection to the moveable platform 1002, 1102.

Various embodiments of a retractable cable assembly 1000, 1100 may include a cable housing 1004 for providing a spring loaded compartment for a reel 1104 containing cable 1108 and a bolt 1106 may position the reel within the retractable cable assembly 1000, 1100. In various embodiments, the cable 1108 may be manually pulled out of the assembly and allowed to retract. In some embodiments, a hook 1012, 1114 may abut a hook stop 1014, 1116 and prevent the cable 1108 from completely retracting back into the retractable cable assembly 1000, 1100. In some embodiments, a rotatable glide 1008, 1112 may be used to direct the cable from the reel 1104 and out of the assembly. In various embodiments, the retractable cable assembly 1000, 1100 may be mounted to the moveable platform 1002, 1102 using pins attached to connect openings 1006.

In various embodiments, the retractable cable assembly 1000, 1100 may be positioned near or at the rear portion of the moveable platform 1002, 1102 on the opposite side of the door 126 of the rigid housing 100. Such a configuration may allow a user to attach the hook 1012, 1114 to the flexible container 600 at a connector 608, 610, 612, 614 and automatically retract a portion of the flexible container 600 to the rear portion of the rigid housing. Such an embodiment ensures an operator need not enter the rigid housing to place the flexible container 600 and, thereby, increase user friendliness while increasing safety. In various embodiments, the retractable cable assemblies 308 near the floor 118 of the rigid housing 300 may be used in conjunction with the retractable cable assembly 1000, 1100 positioned on the moveable platform to ensure proper placement of the flexible container 400, 502, 600. In some embodiments, the retractable cable assembly 1000, 1100 may be positioned near the slack sensor assembly 1118 as shown in FIG. 11.

In various embodiments, the use of retractable cable assemblies 308, 1000, 1100 may position the flexible container 400, 502, 600 such that when the moveable platform 1002, 1102 is raised by the lift system 104, 706 separates the first surface 602 and the second surface 604 of the flexible container 600 such that surfaces are pulled out of their collapsed configuration and into an installed configuration, thereby, extending the drive assembly 626 into an operational configuration that can effectively mix the contents of the flexible container 400, 502, 600.

Figure 12:
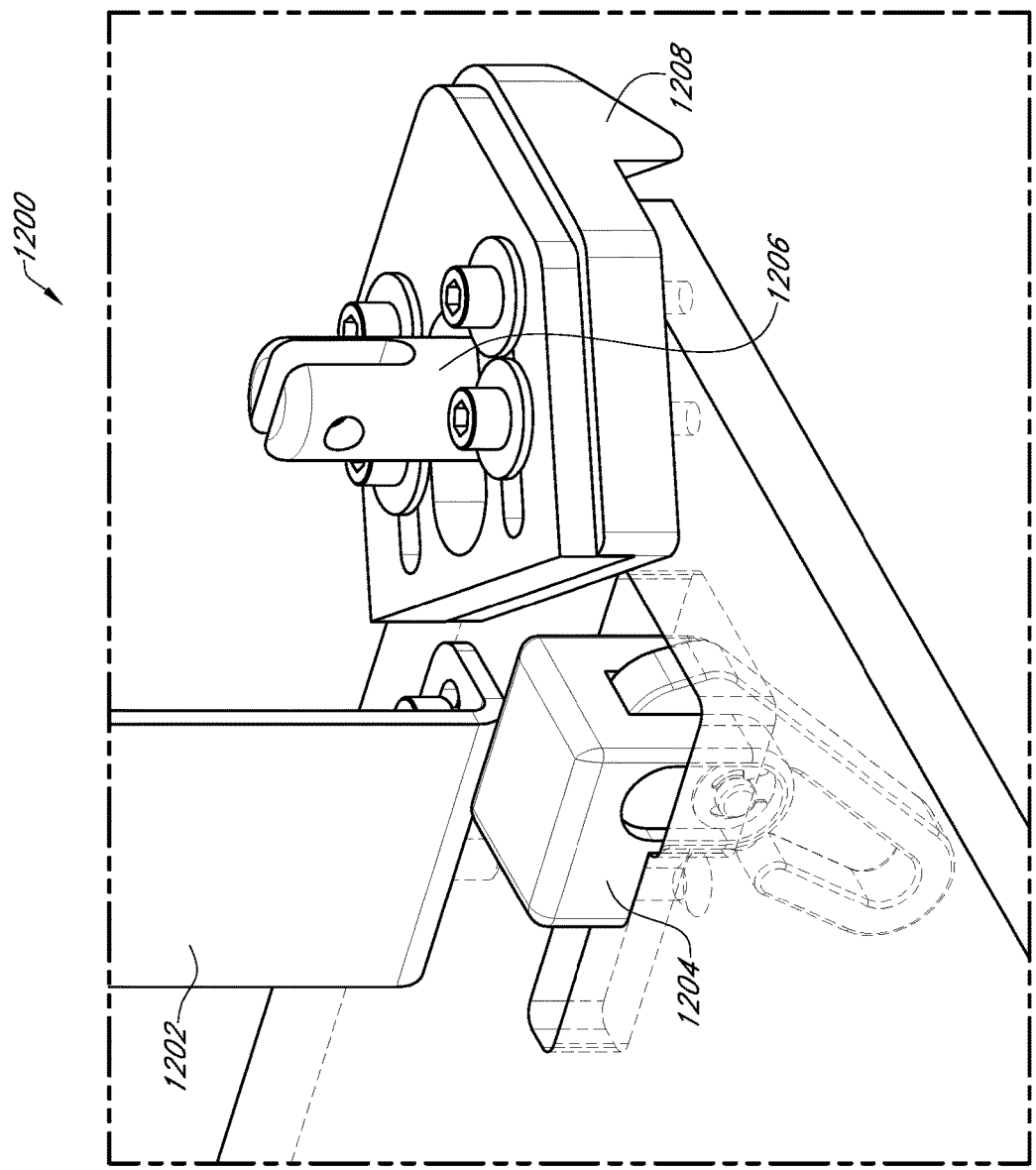
FIG. 12 illustrates a moveable platform 1200 in accordance with one embodiment.

FIG. 12 illustrates an embodiment of a moveable platform 1200 comprising a slack sensor assembly 1202, a securing device 1204, a cable attachment device 1206, and a corner stop 1208. In various embodiments, corner stops 1208 may be placed on four corners of the moveable platform 1200 which can interact with a piece of hardware on the interior 714 rigid housing 100, 200, 300, 702 to prevent movement after installation of the flexible container 400, 502, 600. Such a mechanism is primarily to ensure operator safety and prevent failures during a bioproduction process.

In various embodiments, the cable slack sensor assembly 1202 may be positioned near the cable attachment device 1206 to detect if the moveable platform 1200 is not properly supported by cable 1600 extending from the cable attachment device 1206 and suspending the moveable platform 1200 to the lift system 104, 706. In various embodiments, the slack sensor assembly 1202 interacts directly with the cable 1600 to detect slack in the cable 1600. In some embodiments, slack in the cable 1600 is an indication that the moveable platform 1200 is not properly supported within the rigid housing 100, 200, 300, 702.

In various embodiments, the securing device 1204 may be mounted to the top surface of the moveable platform 1200 and interact with a flexible container 400, 502, 600 suspended below. In some embodiments, the securing device 1204 may be anything capable of interacting with both the moveable platform 1200 and the flexible container 400, 502, 600 to ensure proper installation and positioning of the flexible container 400, 502, 600 for use in a bioreaction or mixing.

Figure 13:
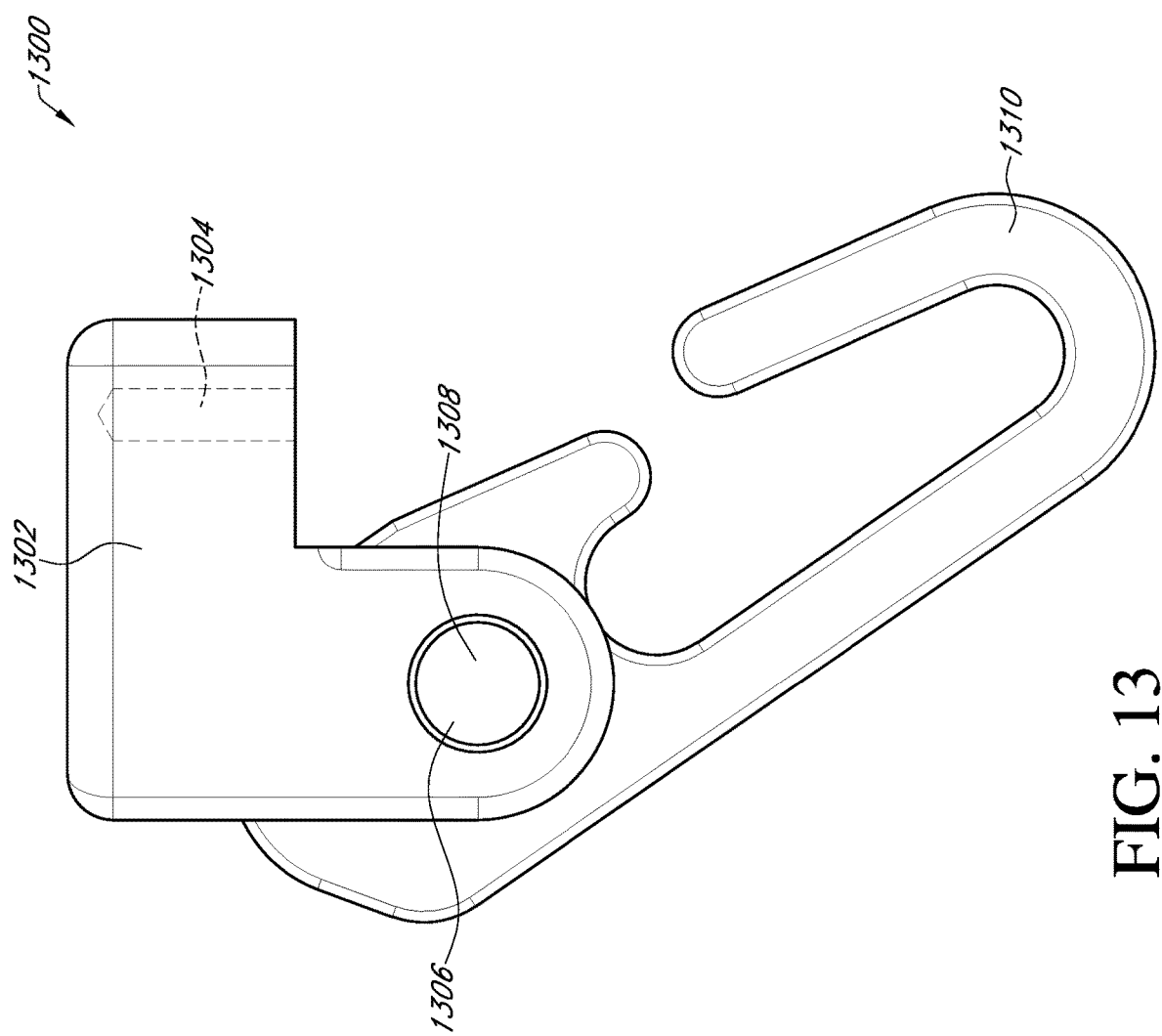
FIG. 13 illustrates a securing device 1300 in accordance with one embodiment.
Figure 14:
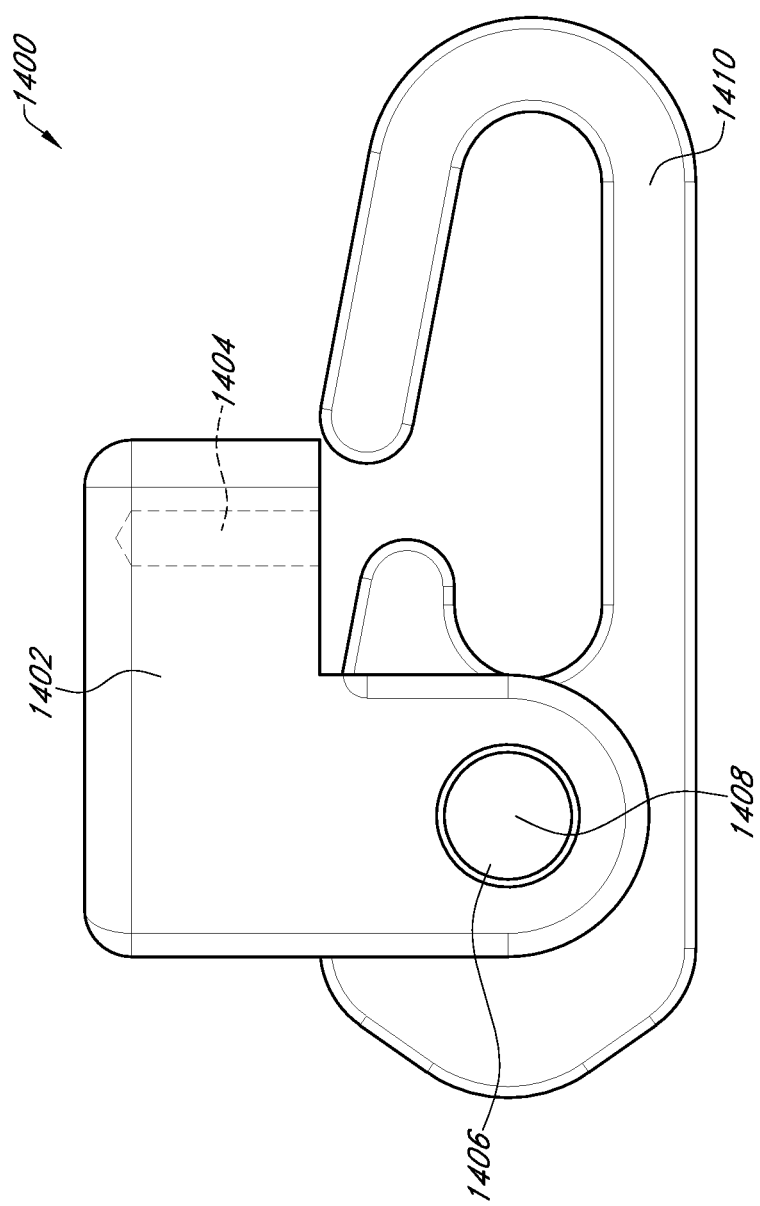
FIG. 14 illustrates a securing device 1400 in accordance with one embodiment.

FIGS. 13 and 14 illustrate embodiments of a securing device 1300, 1400 in an open and a closed configuration respectively. In various embodiments a securing device 1300, 1400 may comprise a mount 1302, 1402 having a mount opening 1306, 1406 for connecting to a hook 1310, 1410 using a pin 1308, 1408 and a connection 1304, 1404 for connecting with the moveable platform 1200.

In various embodiments, the connection 1304, 1404 may be an opening, adhesive, pin, weld or anything that enables a connection to the moveable platform 1200. In some embodiments, the connection 1304, 1404 may interact with a protrusion, weld, adhesive, screw, pin, or anything else useful on the moveable platform 1200 to secure the securing device 1300, 1400.

In various embodiments, the hook 1310, 1410 may be pivotally attached to the mount through a mount opening 1306, 1406 using a pin or other elongated member (not shown). In some embodiments, the open configuration allows the hook to drop below the top surface of the moveable platform 1200 allowing an easy connection to the connectors on the flexible container 400, 502, 600. Once the connection has been made, in some embodiments, the hook 1310, 1410 may swing back into a recess or opening on the moveable platform 1200. Such an embodiment is ideal for preventing failures of the flexible container 400, 502, 600 through physical abrasion with the hooks 1310, 1410.

Figure 15:
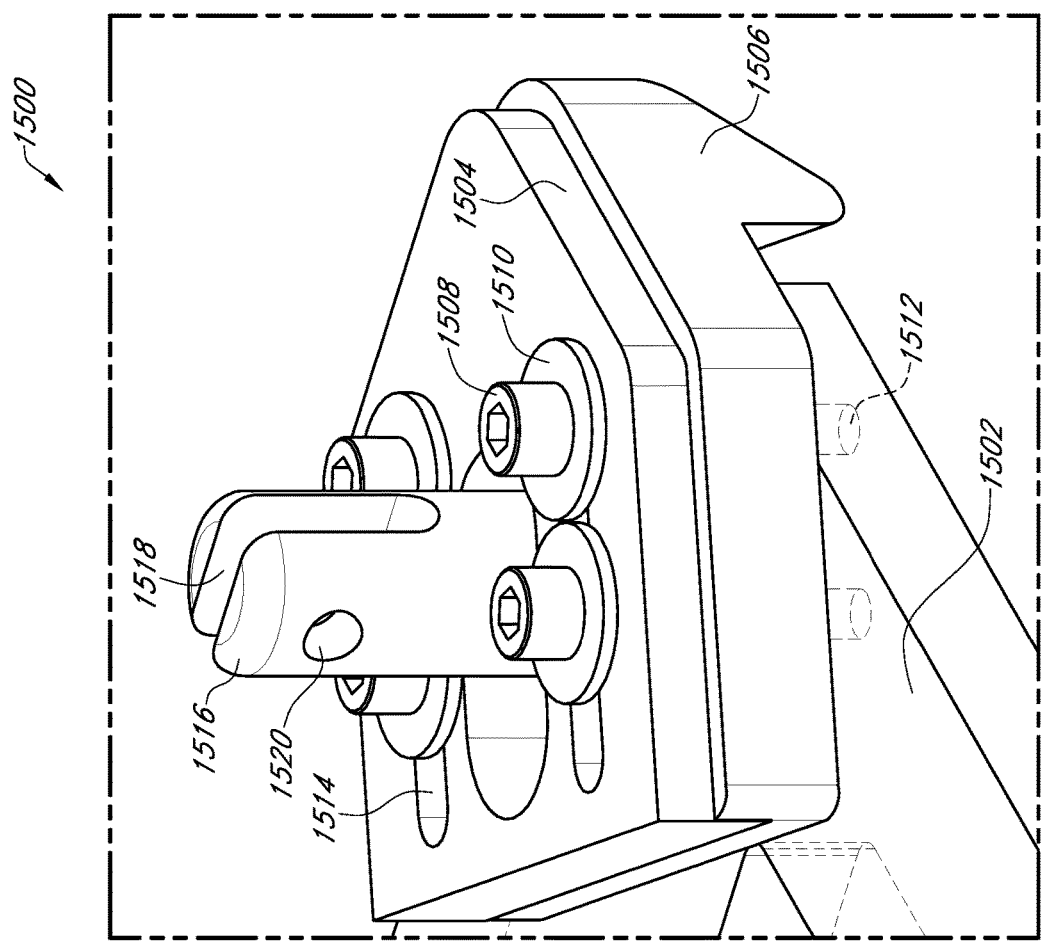
FIG. 15 illustrates a cable attachment device 1500 in accordance with one embodiment.

FIG. 15 illustrates an embodiment of a cable attachment device 1500 mounted to a moveable platform 1502 and comprising a plate 1504, a corner stop 1506, a screw 1508, a washer 1510, a screw receiver 1512, an openings 1514, a cable receiver 1516, a receiver opening 1518, and a pin opening 1520.

In various embodiments, a cable corner stop 1506 may include a hook like element for latching onto something within the interior 714 of the rigid housing 100, 200, 300. In some embodiments, the corner stop 1506 may be mounted to the moveable platform 1502 using a screw 1508 passing through a washer 1510 and being retained by a screw receiver 1512, however, anything that allows a firm connection with the moveable platform 1502 can be used. Such embodiments may include welds, adhesive, bolts, or anything else known or useful.

In various embodiments, the cable attachment device 1500 may include an additional plate 1504 having elongated openings 1514 for adjusting the position of the cable attachment device 1500. In various embodiments, the corner stop 1506 may need to be adjusted to better interact with hardware on the rigid housing 100, 200, 300, 702. In some embodiments, the screw 1508 position may be adjusted within the openings 1514 to enable repositioning of the cable attachment device 1500.

In various embodiments, a cable receiver 1516 may extend away from the plate 1504 or corner stop 1506 and include a cable receiver 1516 for receiving a cable 1600. In some embodiments, the cable 1600 may be secured to the cable receiver 1516 using a pin opening 1520 and pin attachment. However, other embodiments may include connecting the cable 1600 to the cable receiver 1516 using a weld, adhesive, screw, or another connection known or useful in the field. In various embodiments, a cable 1600 extends from each corner of the moveable platform 1502 to suspend the platform in a stable manner and enable proper positioning of the flexible container 400, 502, 600 within the rigid housing 100, 200, 300, 702. In some embodiments, the cable 1600 needs to have enough tensile strength to support the moveable platform 1502, flexible container 400, 502, 600 and the various components resting on top of the moveable platform 1502, including, but not limited to a motor assembly, condenser 734, and other hardware and tubing required by the bioproduction process.

Figure 16:
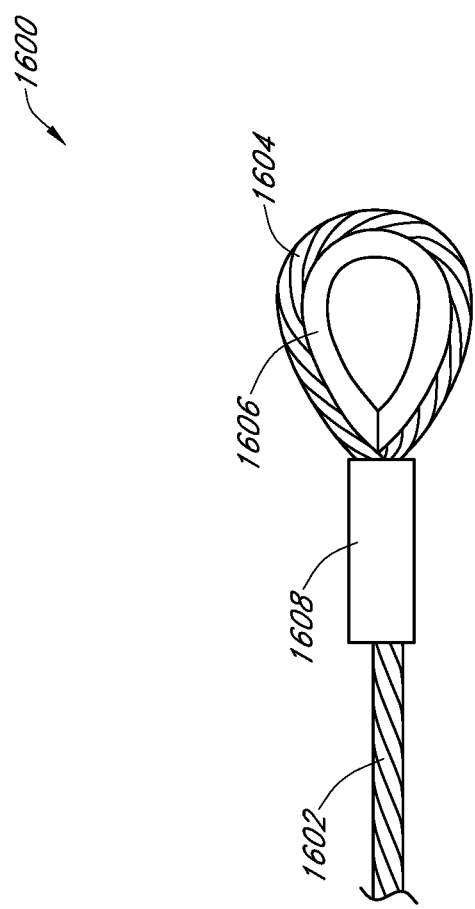
FIG. 16 illustrates a cable 1600 in accordance with one embodiment.

FIG. 16 illustrates an embodiment of a cable 1600 comprises an elongated portion 1602, a loop 1604, a polymer 1606, and a collar 1608. In various embodiments, cable 1600 is used throughout the configurable mixing system. In various embodiments, the lift system 104, 706 may include cable 1600. In various embodiments, cable 1600 may be used in the retractable cable assemblies 308, 808, 1000, 1100. In various embodiments, any system disclosed herein using pulleys, connectors, attachments, suspension devices, and anywhere found to be useful cables 1600 may be used although not always depicted for clarity purposes. In various embodiments, the cable may be a belt, string, chain, rope, cord, or any elongated device capable of attached to a variety of different connector or attachment elements.

In various embodiments, the cable 1600 may include a loop 1604 having a polymer 1606 affixed to prevent damage to the various components the cable 1600 may interact with or suspend. In various embodiments, a collar 1608 may secure the cable 1600 to itself to create the loop 1604.

In the various embodiments disclosed herein that require suspending, movement, or transfer of power cables 1600 may be used to facilitate such actions. Cables 1600 are not shown in all of the figures for simplicity, but it will be appreciated that they interact with various elements disclosed herein.

Figure 17:
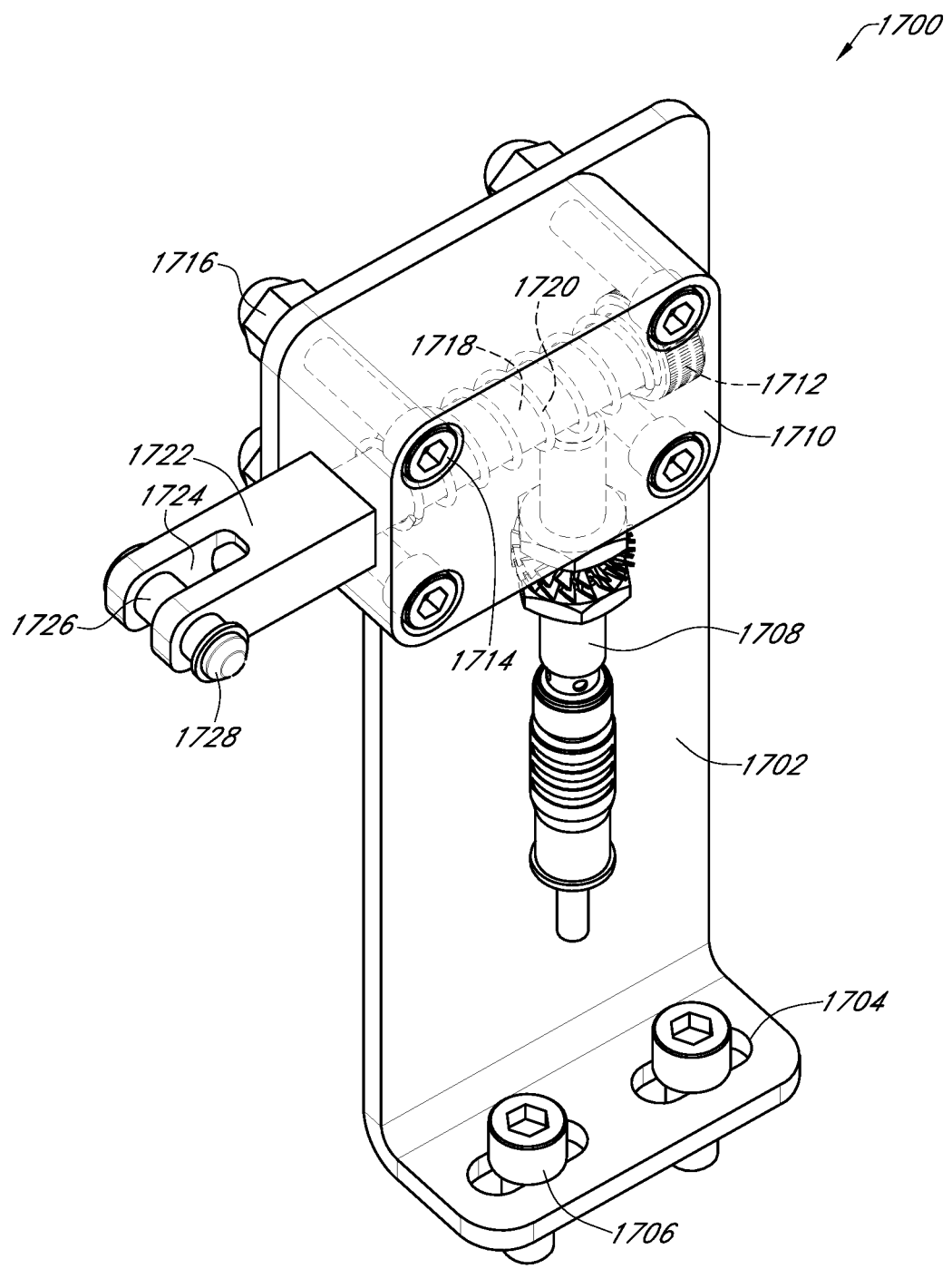
FIG. 17 illustrates a cable slack sensor assembly 1700 in accordance with one embodiment.
Figure 18:
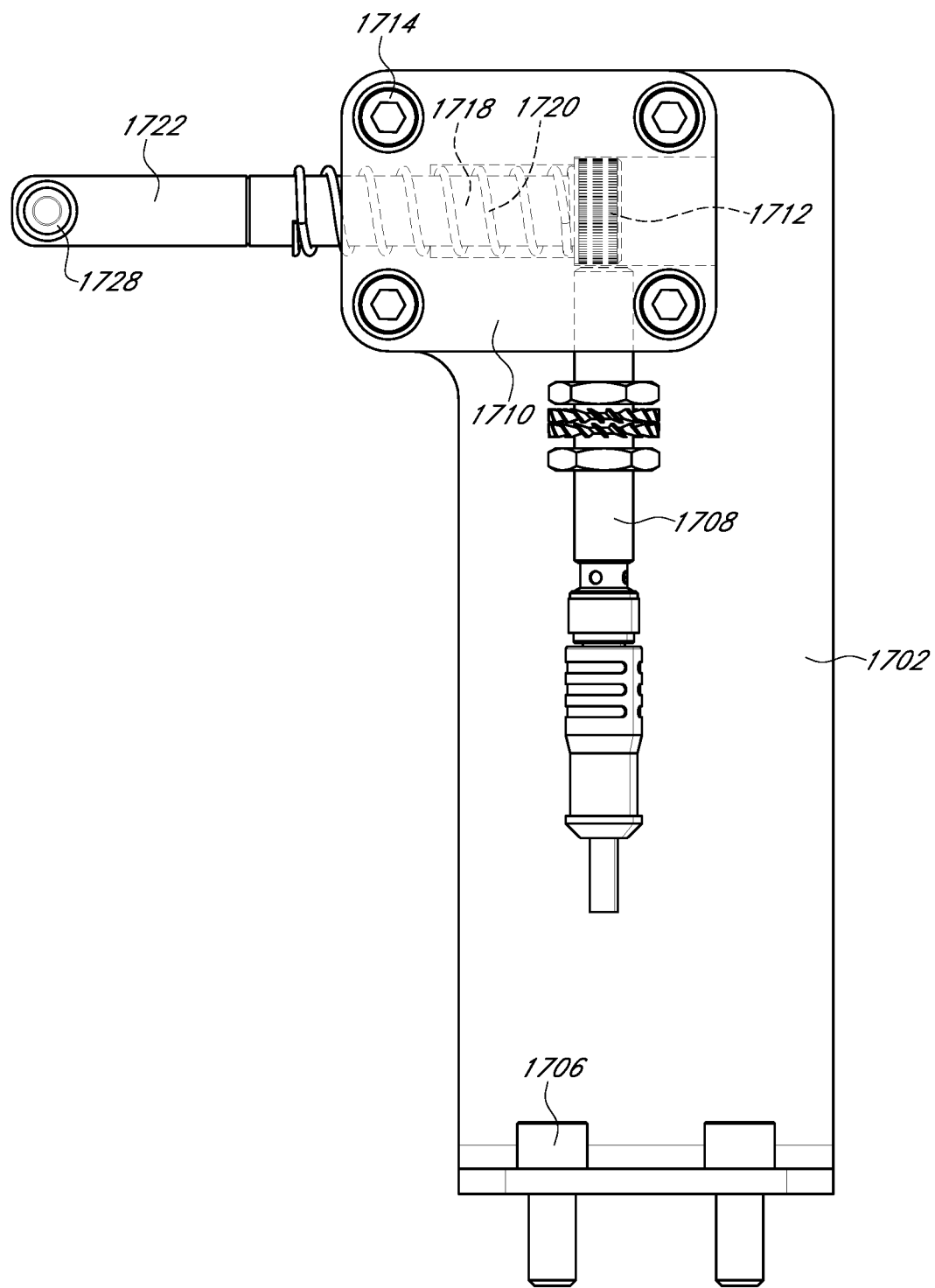
FIG. 18 illustrates a cable slack sensor assembly 1800 in accordance with one embodiment.
Figure 19:
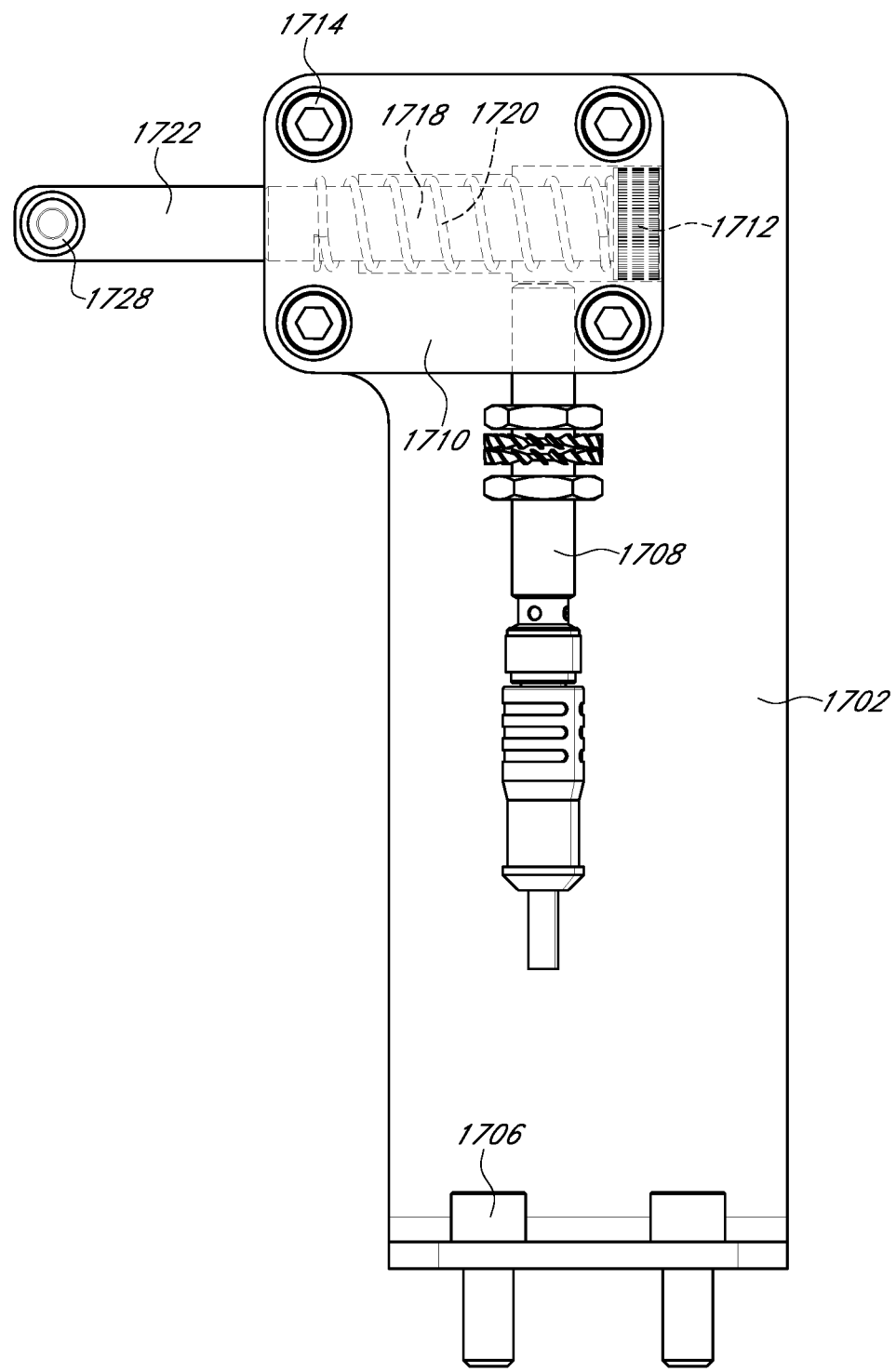
FIG. 19 illustrates a cable slack sensor assembly 1900 in accordance with one embodiment.

FIGS. 17, 18, and 19 illustrate an embodiment of a cable slack sensor assembly 1700 comprising a bracket 1702 have a sensor 1708 and a readable object 1712 mounted thereto.

In various embodiments, the bracket 1702 may be mounted to the moveable platform 1200 near or adjacent to the cable attachment device 1206 as seen in FIG. 12. In some embodiments, the bracket 1702 may be mounted to the moveable platform 1200 with screws 1714 projecting through an opening 1704 in the bracket 1702 and affixing to the surface of the moveable platform 1200. In other embodiments, the bracket 1702 may be welded, adhered, or secured to the moveable platform 1200 in any way that is known or useful.

In various embodiments, a sensor 1708 may be mounted to the bracket 1702 and a readable object 1712 may be positioned such that its movement may be detected by the sensor. A skilled artisan will appreciate that there are many ways to position a sensor 1708 and readable object 1712 relative to one another where in one position the readable object 1712 provides a signal to the sensor 1708 and in another position the readable object 1712 does not provide a signal to the sensor 1708. In some embodiments, the sensor 1708 may detect an optical change, a magnetic change, an electrical change, or any other kind of change a sensor 1708 can detect that is known or useful.

In various embodiments, the readable object 1712 may be secured to a first end of a rod 1718 and a cable attachment 1722 may be secured to a second end of the rod 1718. In some embodiments, the rod 1718, readable object 1712, cable attachment 1722 assembly may be secured onto the bracket 1702 with a positioning plate 1710. In some embodiments, the positioning plate 1710 may be held in place by a screw 1714 passing through the plate and into an opening on the bracket 1702 and a nut 1716 can secure the screw 1706 to the opposing side of the bracket 1702. In some embodiments, the positioning plate 1710 can be secured to the bracket 1702 using adhesive, welds, or any other method known or useful in the art. In various embodiments, the rod 1718, readable object 1712, cable attachment 1722 assembly may be secured to the bracket 1702 through another other method known or useful.

In various embodiments, the cable attachment 1722 may include a cable opening 1724 for receiving a cable 1600. In some embodiments, the cable 1600 may be secured within the cable opening 1724 using a pin 1726 passing through an opening on the cable attachment 1722 and affixed with an affixment 1728. A skilled artisan will appreciate that there are countless other methods of securing a cable 1600 to the cable attachment 1722 region.

In various embodiments, the spring 1720 is positioned between the readable object 1712 and the cable attachment 1722 on the rod 1718 and within the confines of the positioning plate 1710. In various embodiments, the resting position of the readable object 1712 is shown in FIGS. 17 and 19. In various embodiments a load on the cable attachment 1722 may cause the readable object 1712 to move over the sensor 1708 as seen in FIG. 18.

In various embodiments, a cable 1108 may be affixed to the moveable platform 1200 and run through the cable attachment 1722 perpendicular to the rod 1718. In such embodiments, the cable attachment device 1206 may be positioned such that the cable 1600 applies a load to the cable attachment 1722 and moves the readable object 1712 over the sensor 1708. In some embodiments, when a load is applied the cable 1600 is taut because the moveable platform 1200 is positioned appropriately. In various embodiments, a cable 1600 is affixed to each corner of the moveable platform 1200 and each cable 1600 runs through a cable slack sensor assembly 1700. If there is a malfunction in the moveable platform 1200 and one of the corners lifts relative to the others a slack in the cable 1600 is created and the spring snaps the readable object 1712 into the configuration shown in FIGS. 17 and 19. In various embodiments, the cable slack sensor assembly 1700 may then send a signal to the control system 708 or HMI 132 to deactivate the motive force device 106 and suspend operation of the moveable platform 1200.

In various embodiments, the sensor 1708 may be positioned to read the readable object 1712 in its resting position instead of in its taut position. A skilled artisan will appreciate that any sensor system that can detect slack in a cable 1600 may be useful for various moveable platform 1200 embodiments disclosed herein.

In various embodiments, the readable object is a bolt or other metal object. In some embodiments, the readable object may include a magnet or a color that is detectable by a sensor.

In various embodiments, a sensor system may be used to detect whether the moveable platform 1200 is level. Such a system would work with a variety of lift systems that do not include cables, but belts, gear drives integrated with teeth or tracks or any other system. In various embodiments, such a system may incorporate an air bubble and colored dye or water where an optical sensor may detect a change in absorption if the air bubble moves to an undesirable position.

Figure 20:
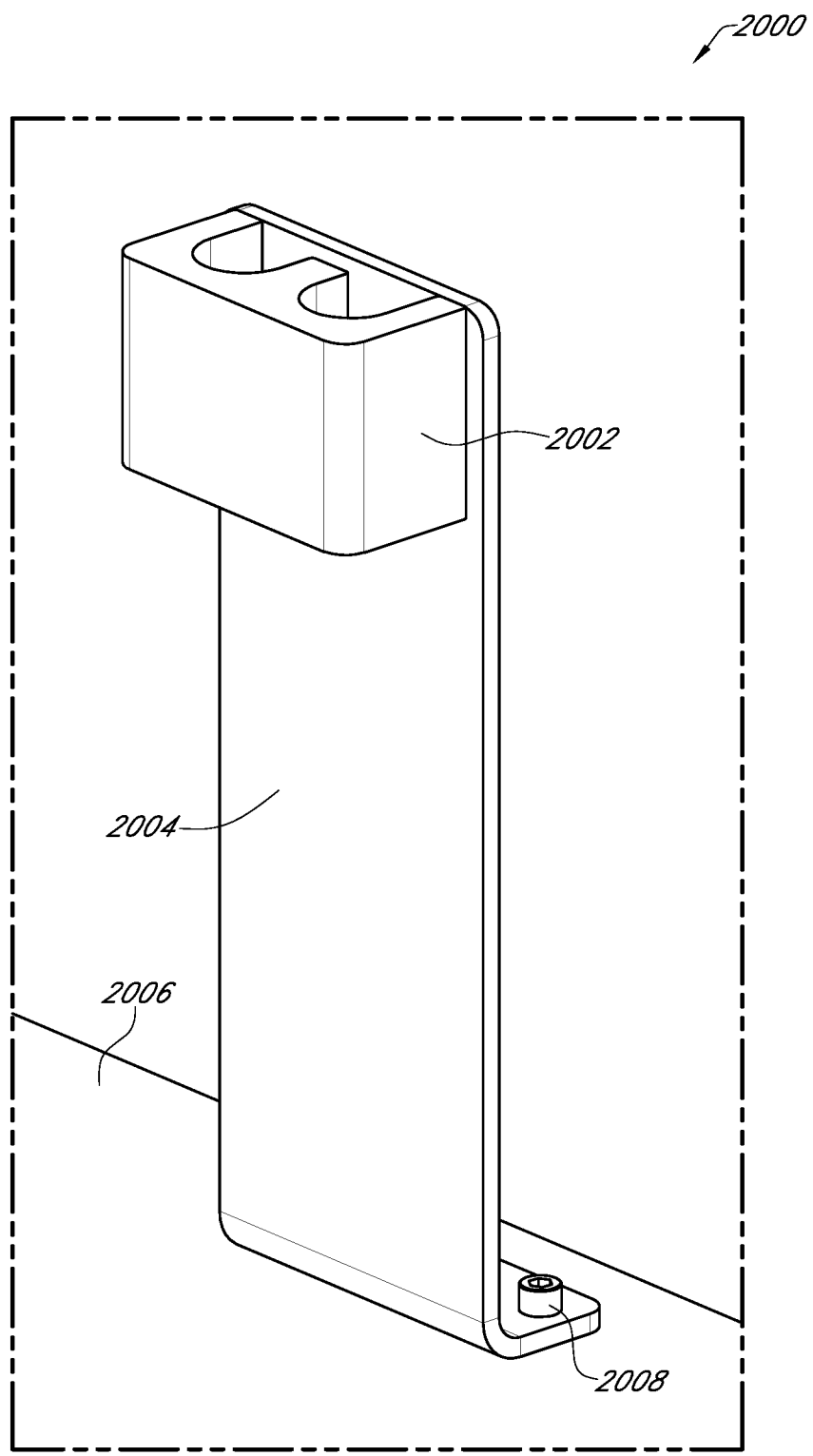
FIG. 20 illustrates a power cable clamp assembly 2000 in accordance with one embodiment.

FIG. 20 illustrates an embodiment of a power cable clamp assembly 2000 comprising a cable clamp 2002, a bracket 2004, a moveable platform 2006, and a screw 2008.

In various embodiments, a variety of components on the moveable platform 130, 732, 800, 1002, 1102, 1200, 1502, 2006 require power such as the motive force device 106, cable slack sensor assembly 1700, and the motive force device 106 (when located on the moveable platform).

In various embodiments, a power cable 134 may be routed from the exterior housing 704 or elsewhere up and into the interior 714 of the rigid housing 100, 200, 300, 702 and may then be routed to the moveable platform 2006 through the power cable clamp assembly 2000. In some embodiments, a bracket 2004 may be secured to the moveable platform 2006 with screws 2008 or by another means and a cable clamp 2002 may secure the power cable 134 to the bracket 2004. In various embodiments, the power cable 134 may then be routed to the various systems on the moveable platform 2006 that require power.

Figure 21:
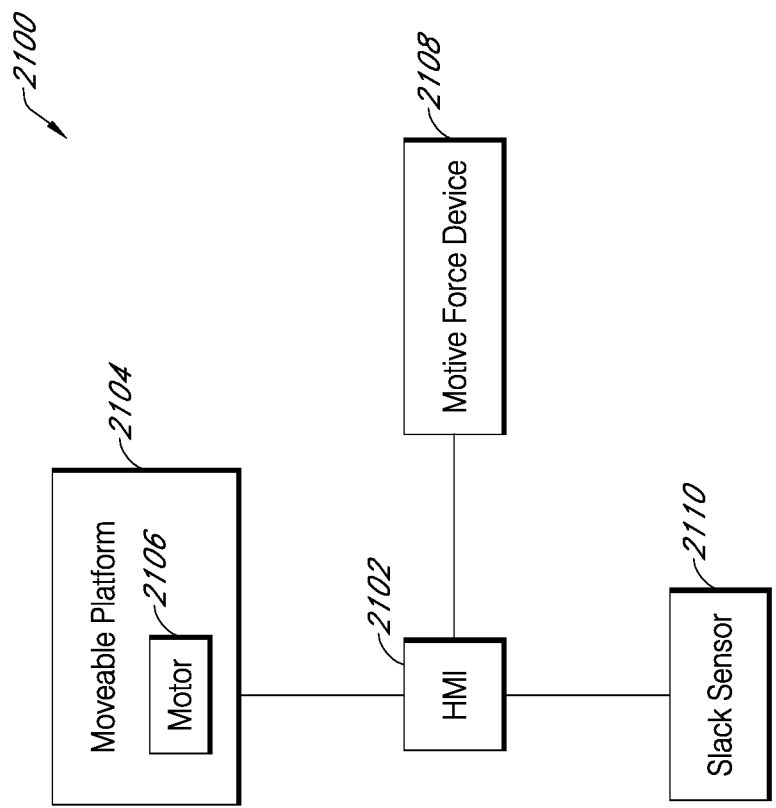
FIG. 21 illustrates a control system 2100 in accordance with one embodiment.

FIG. 21 illustrates an embodiment of a control system 2100 comprising a controller 2102, a moveable platform 2104, a motor 2106, a motive force device 2108, and a slack sensor assembly 2110.

In various embodiments, a controller 2102 directs a motive force device 2108 to activate, deactivate, and operate in forward or reverse, and the speed at which it operates. In some embodiments, an operator determines the settings for the motive force device 2108 through an interface on the controller 2102. In some embodiments, a slack sensor assembly 2110 provides information to the controller 2102 regarding the orientation of the moveable platform 2104. In various embodiments and described above, the slack sensor assembly 2110 may determine whether it is appropriate for the motive force device 2108 to be active or inactive. In some embodiments, a signal may travel to the controller 2102 where the controller 2102 determines a control signal to send to the motive force device 2108.

In various embodiments, the slack sensor assembly 2110 may be located on the moveable platform 2104 and in some embodiments it may be housed separately. In various embodiments, more one or more controllers 2102 may be used to direct various aspects of the lift system 104, 706 or sense and enact changes within the flexible container 400, 5002, 600 as part of a bioproduction process. Later a catch assembly 730 is described as a manual apparatus and it will be appreciated that various aspects may be automated and controlled using the controller 2102 in conjunction with a sensors and actuators.

Figure 22:
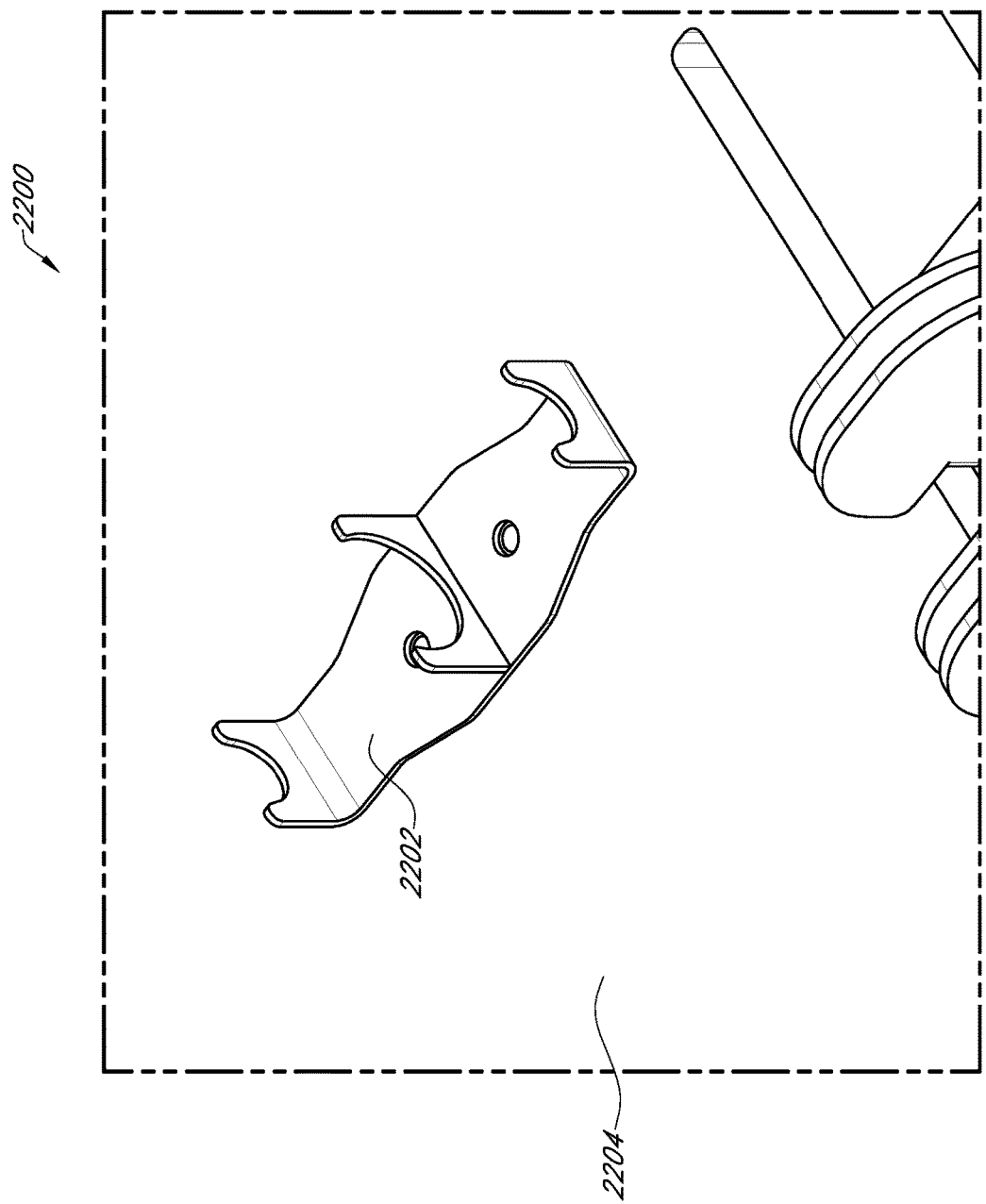
FIG. 22 illustrates a holder 2200 in accordance with one embodiment.

FIG. 22 illustrates an embodiment of a holder 2200 comprising a bracket 2202 mounted to a moveable platform 2104. In various embodiments, a variety of components may need to be held in place on the surface of the moveable platform 2104. In some embodiments, brackets may be mounted to the moveable platform 2104 by soldering, weld, screw, pin, or any other securing device. In some embodiments, the bracket 2202 may be a filter bracket 814 to secure one or more filters to the moveable platform 2104. In some embodiments, tubes may need to be secured to the moveable platform 2104 or any other object known or useful in bioproduction.

Figure 23:
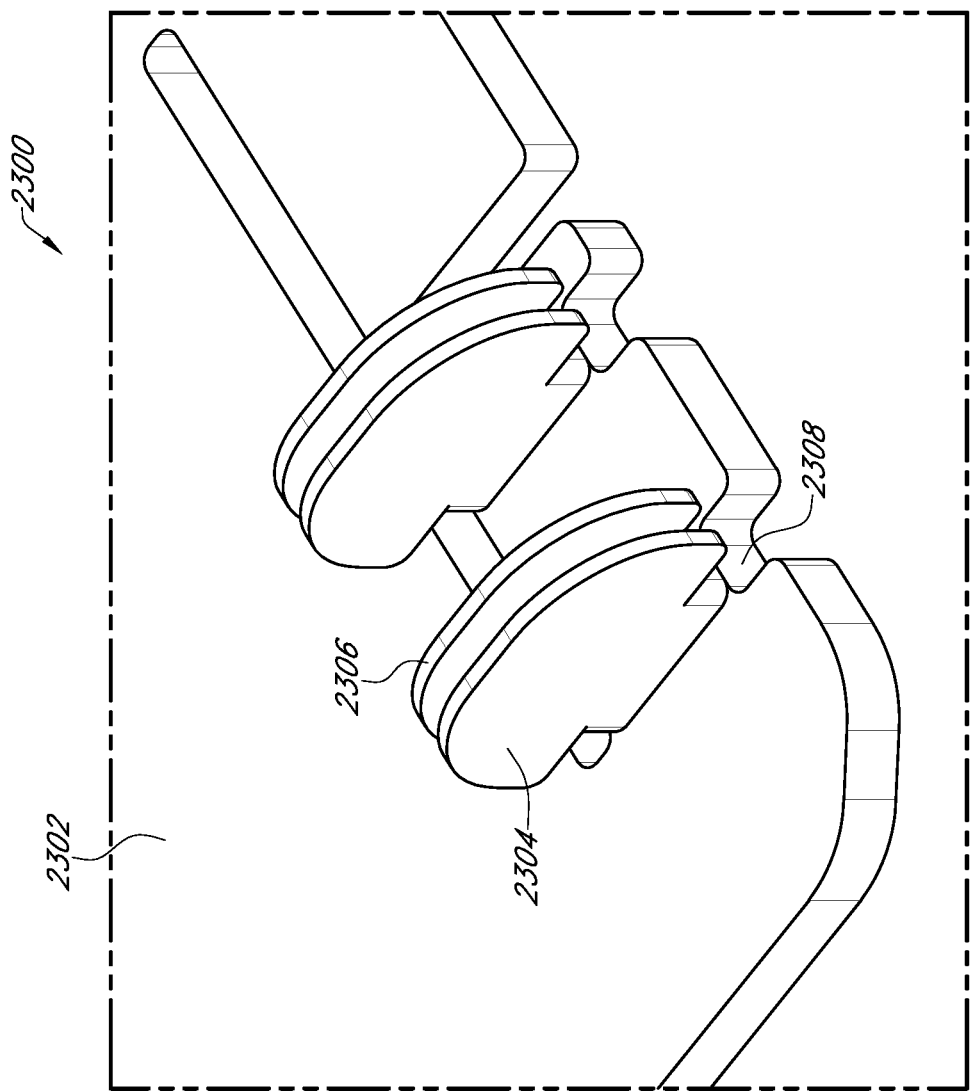
FIG. 23 illustrates a tube holder assembly 2300 in accordance with one embodiment.

FIG. 23 illustrates an embodiment of a tube holder assembly 2300 comprising a moveable platform 2302 and a tube holder 2304 affixed thereto. In various embodiments, the tube holder 2304 may be affixed to the moveable platform 2302 using pins, screws, solder, weld, adhesive, or any other known securing method known or useful.

In various embodiments, a tube 518 may extend from the first surface 602 of a flexible container 600 and further extend through a notch 2308 in a moveable platform 2302. In some embodiments, the tube 518 extending through the notch 2308 may be positioned into the opening 2306 of a tube holder 2304 and be restrained through frictional interaction with the tube holder 2304. In various embodiments, tube 518 may connect to the condenser 734 and return tubes may allowed for reintroduction of fluid or liquid back into the flexible container 600 suspended below the moveable platform 2302.

Figure 24:
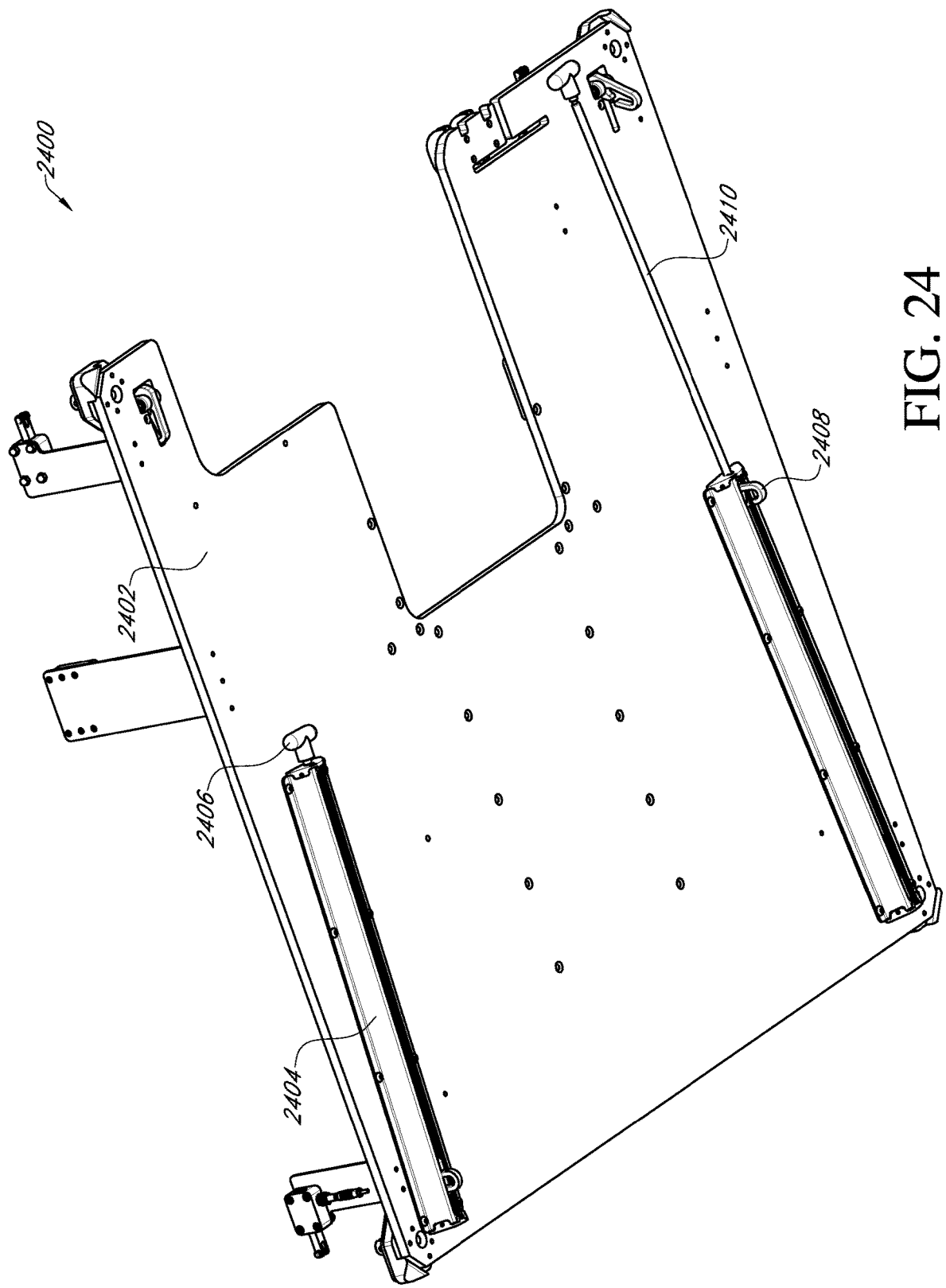
FIG. 24 illustrates a guide hook assembly 2400 in accordance with one embodiment.

FIG. 24 illustrates an embodiment of a guide hook assembly 2400 comprising a moveable platform 2402 and a guide 2404 affixed to the surface of the moveable platform 2402. In various embodiments, a hook 2508 moves into a pocket in the guide 2502 and extends outwardly with a handle 2406 on one end. In various embodiments, a hook 2408 attaches to a portion of the hook 2508 housed within the guide. In various embodiments, an operator may pull a handle 2406 to bring the hook located on the rod from a rear position to a forward position within the guide. Similar to the retractable cable assemblies 308, the guide and hook system allows a user to bring a hook 2408 to a forward position near the door of the rigid housing 100, 200, 300, 702 and attach connectors 608, 610, 612, 614 to the hook 2408. An operator can then push the handle 2406 to move the hook 2408 to a rear position and correctly position the flexible container 400, 502, 600 within the rigid housing 100, 200, 300, 702. In some embodiments the rod 2410 may be spring loaded for ease of actuation between rear and forward positions.

Figure 25:
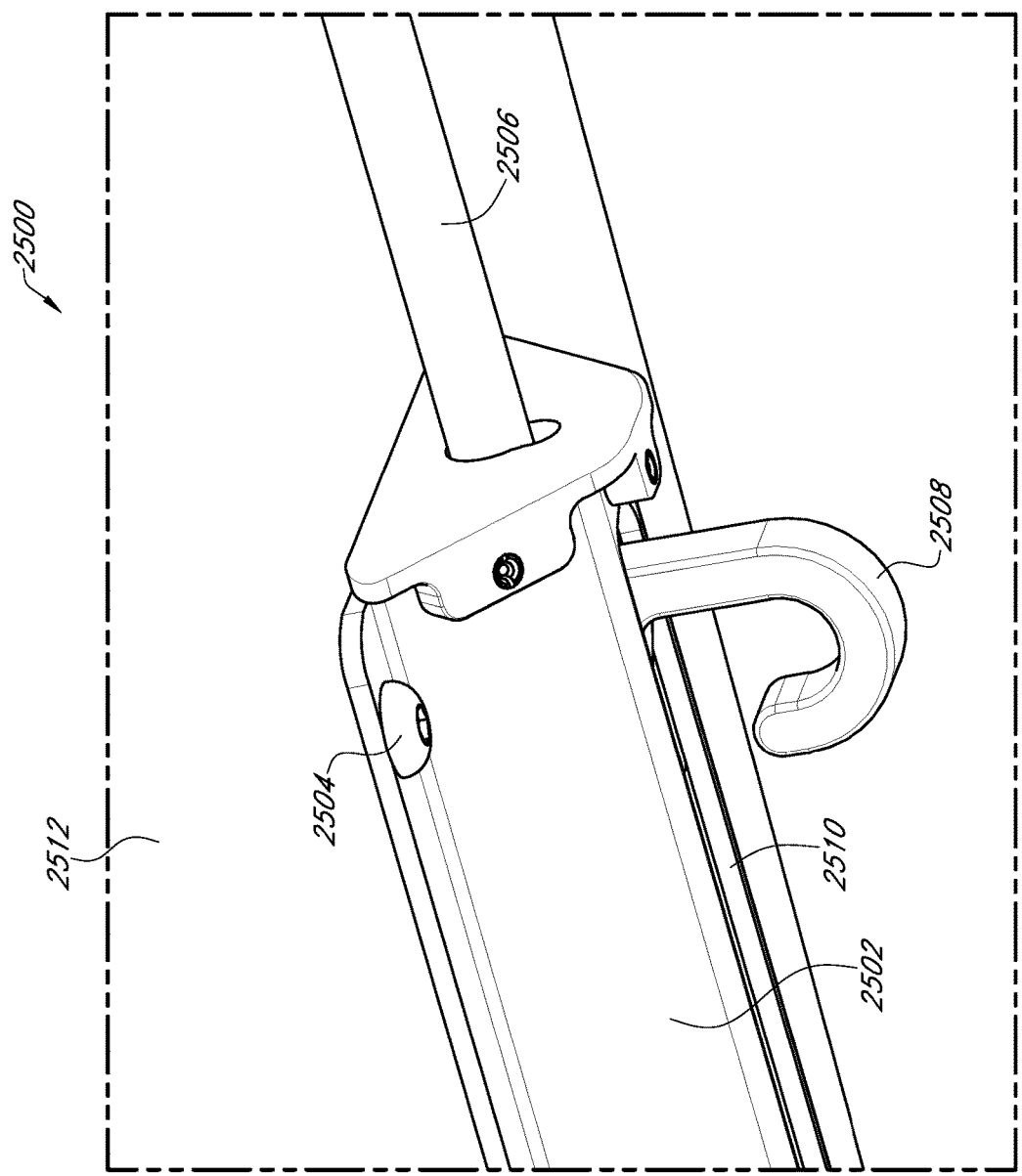
FIG. 25 illustrates a guide hook assembly 2500 in accordance with one embodiment.

FIG. 25 illustrates a close of up of guide hook assembly 2500 comprises a guide 2502, a screw 2504, a rod 2506, and a hook 2508 extending out of a slot 2510 according to various embodiments. In various embodiments, the guide hook assembly 2500 may be soldered, welded, screwed, or adhered to the underside of the moveable platform 2512. In various embodiments, the rod 2506 moves freely within the slot 2510 to forward and rear positions.

Figure 26:
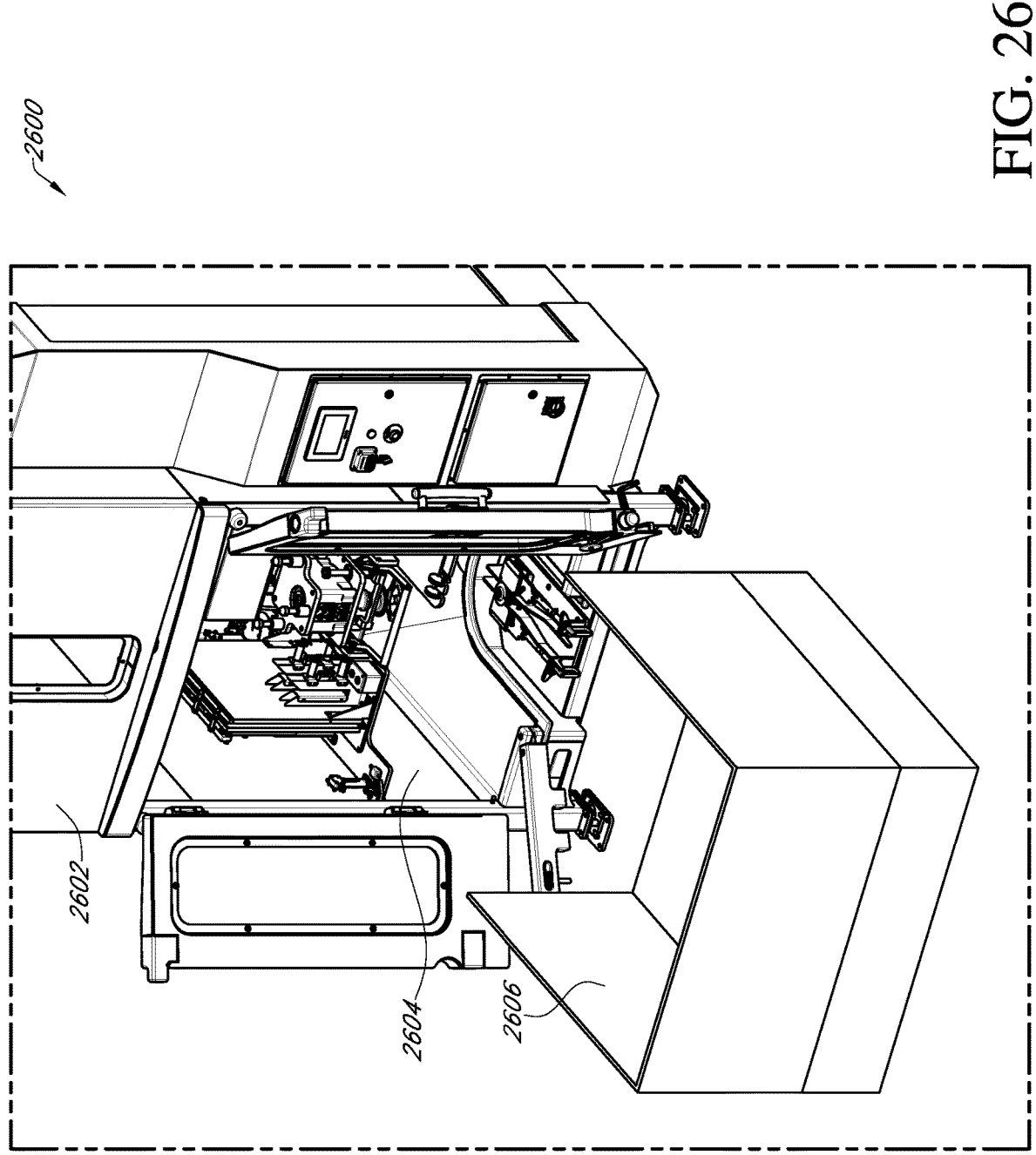
FIG. 26 illustrates a bioproduction system 2600 in accordance with one embodiment.

FIG. 26 illustrates a bioproduction system 2600 comprises a rigid housing 2602 having an interior 2604. In various embodiments, an end user may purchase a rigid housing 2602 and have it assembled within a production facility. On an as needed basis, the end user may purchase the single use portion of the bioproduction system 2600 that may include a flexible container 400, 502, 600 having a tube set mounted to a tube management plate 522. The entire single use portion may ship to the end user in a single package 2606 and an operator may then unpack the consumable portion and insert it into the interior of the rigid housing 2602 for installation.

Figure 27:
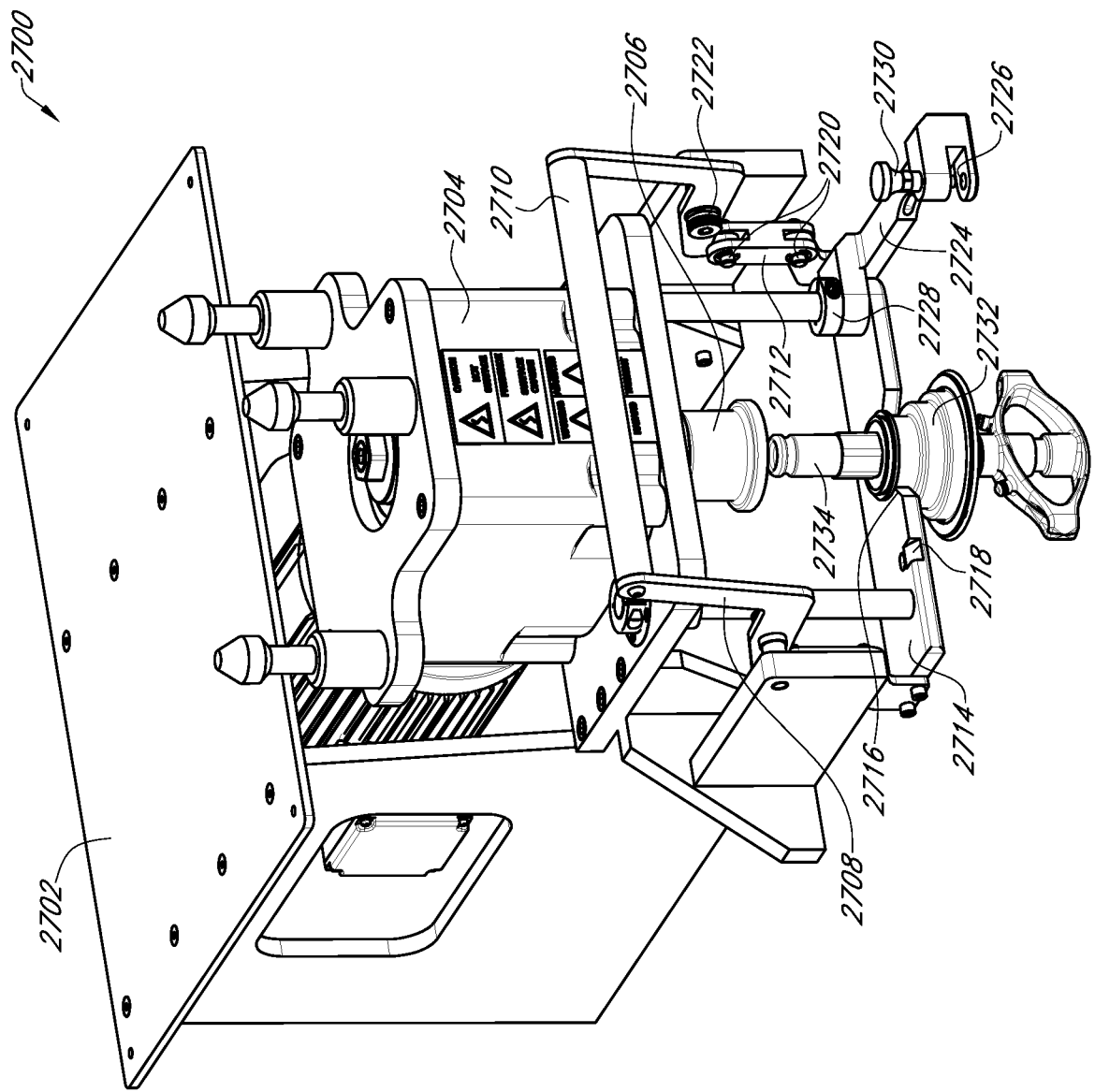
FIG. 27 illustrates a bearing housing retention assembly 2700 in accordance with one embodiment.

FIG. 27 illustrates a bearing housing retention assembly 2700 comprising a motor housing 2702, a motor 2704, a locking sleeve 2706, a clamp assembly 2708, a handle 2710, a pivot portion 2712, a retention plate 2714, a retention plate opening 2716, a notch 2718, an attachment region 2720, a joint 2722, a swing arm 2724, a swing opening 2726, a hinge 2728, a spring loaded pin 2730, a bearing housing 2732, and a drive shaft 2734.

In various embodiments, a motor housing 2702 mounts to a moveable platform (shown in various figures). The motor housing 2702 may secure a motor and the motor 2704 may include a rotatable locking sleeve 2706 affixed thereto.

In various embodiments, a bearing housing retention assembly 2700 may mount to either or both of the motor housing 2702 and motor 2704. In various embodiments, the purpose of the bearing housing retention assembly 2700 is to secure a bearing housing 2732 and drive shaft 2734 extending from a flexible container 400, 502, 600 such that the drive shaft 2734 is locked into rotational alignment with the motor 2704 and the motor may then provide rotational movement to the helical drive assembly 416 within the flexible container 400, 502, 600.

In various embodiments, once the flexible container 400, 502, 600 is positioned within the rigid housing 100, 200, 300, 702, 2602 the bearing housing 2732 may be inserted into a retention plate opening 2716 located on the retention plate 2714. In some embodiments, the bearing housing 2732 may include a recess that engages the retention plate opening 2716. A swing arm 2724 may then pivot about a hinge 2728 to change from an open to a closed configuration in order to secure the bearing housing 2732. In some embodiments, the swing arm 2724 may include a swing opening 2726 that is positioned around a notch 2718 on the retention retention plate opening 2716. A spring loaded pin 2730 may then engage the notch 2718, thereby, locking the swing arm 2724 onto the bearing housing 2732 such that the bearing housing 2732 is restricted to the retention plate opening 2716.

In various embodiments, an operator may pull a handle 2710 to actuate a clamp assembly 2708 to move the drive shaft 2734 up into the locking sleeve 2706 located on the motor 2704. In various embodiments, the handle 2710 may be mounted to the motor housing 2702 at a joint 2722 which allows pivotal movement of the handle 2710. In some embodiments, the handle 2710 may be pivotally attached to the retention plate 2714 through a pivot portion 2712 where the pivot portion 2712 includes attachment regions 2720 connecting the retention plate 2714 to the handle 2710.

Figure 28:
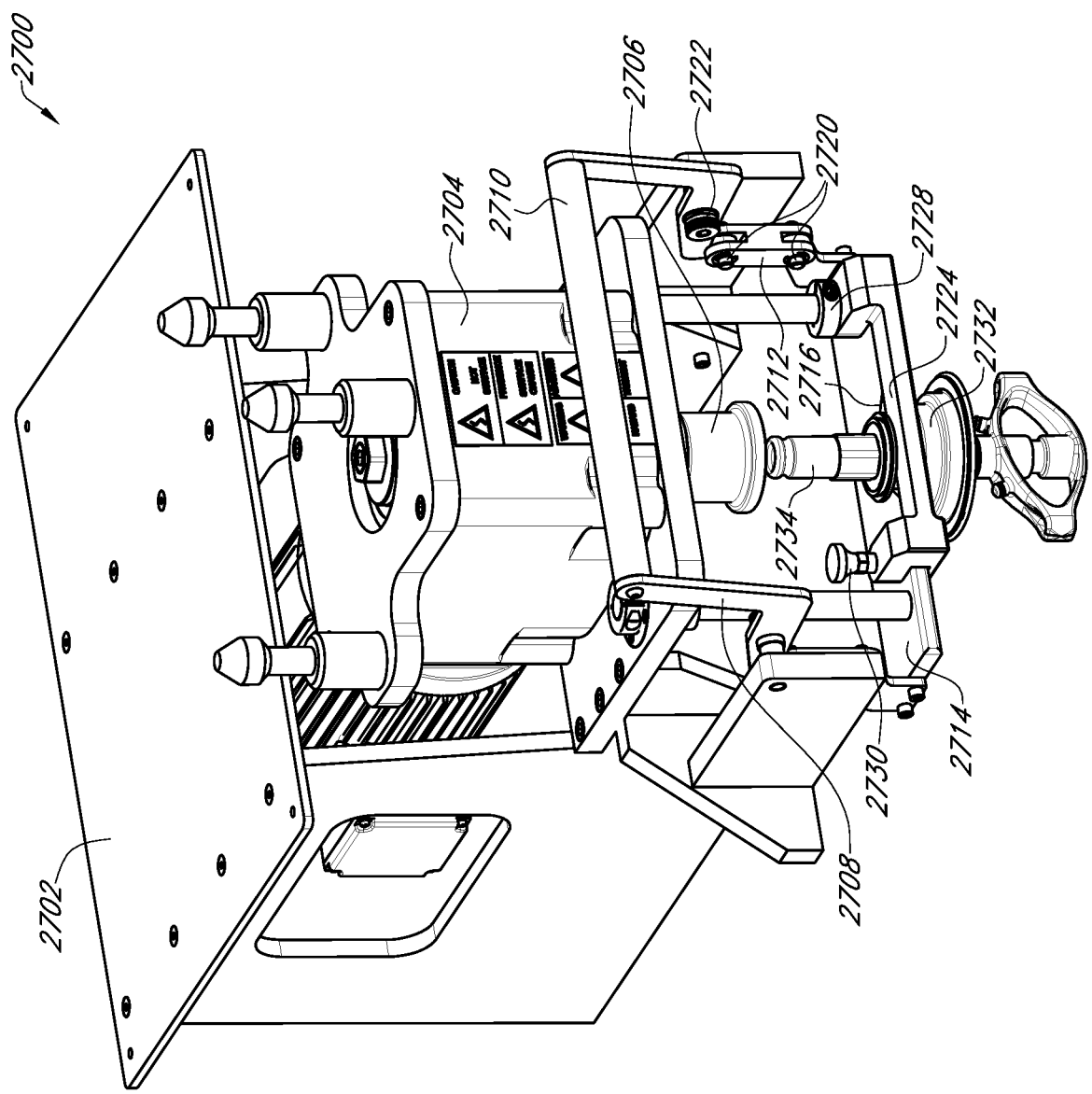
FIG. 28 illustrates a bearing housing retention assembly 2800 in accordance with one embodiment.
Figure 29:
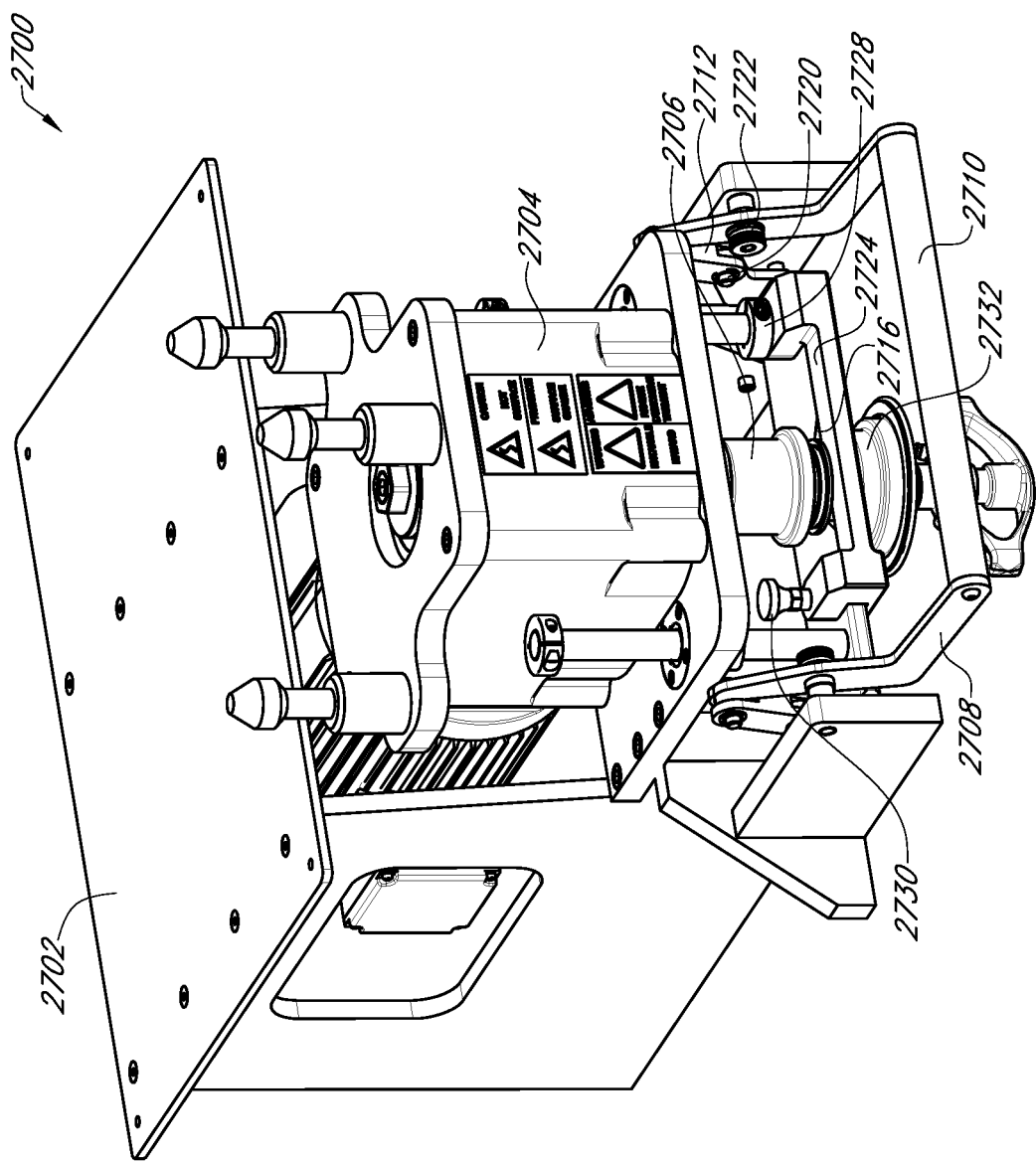
FIG. 29 illustrates a bearing housing retention assembly 2900 in accordance with one embodiment.

FIG. 27 illustrates an embodiment in which both the swing arm 2724 and clamp assembly 2708 are in an open configuration and ready to receive the bear bearing housing 2732. FIG. 28 illustrates an embodiment where the swing arm 2724 is closed and the bearing housing 2732 is locked in place, but the clamp assembly 2708 is still in an open configuration so the drive shaft 2734 from the flexible container 400, 502, 600 has not engaged the motor 2704. FIG. 29 illustrates an embodiment in which both the swing arm 2724 and the clamp assembly 2708 are in closed and locked configuration where the drive shaft 2734 has engaged the locking sleeve 2706 and is in rotational communication with the motor 2704.

Figure 30:
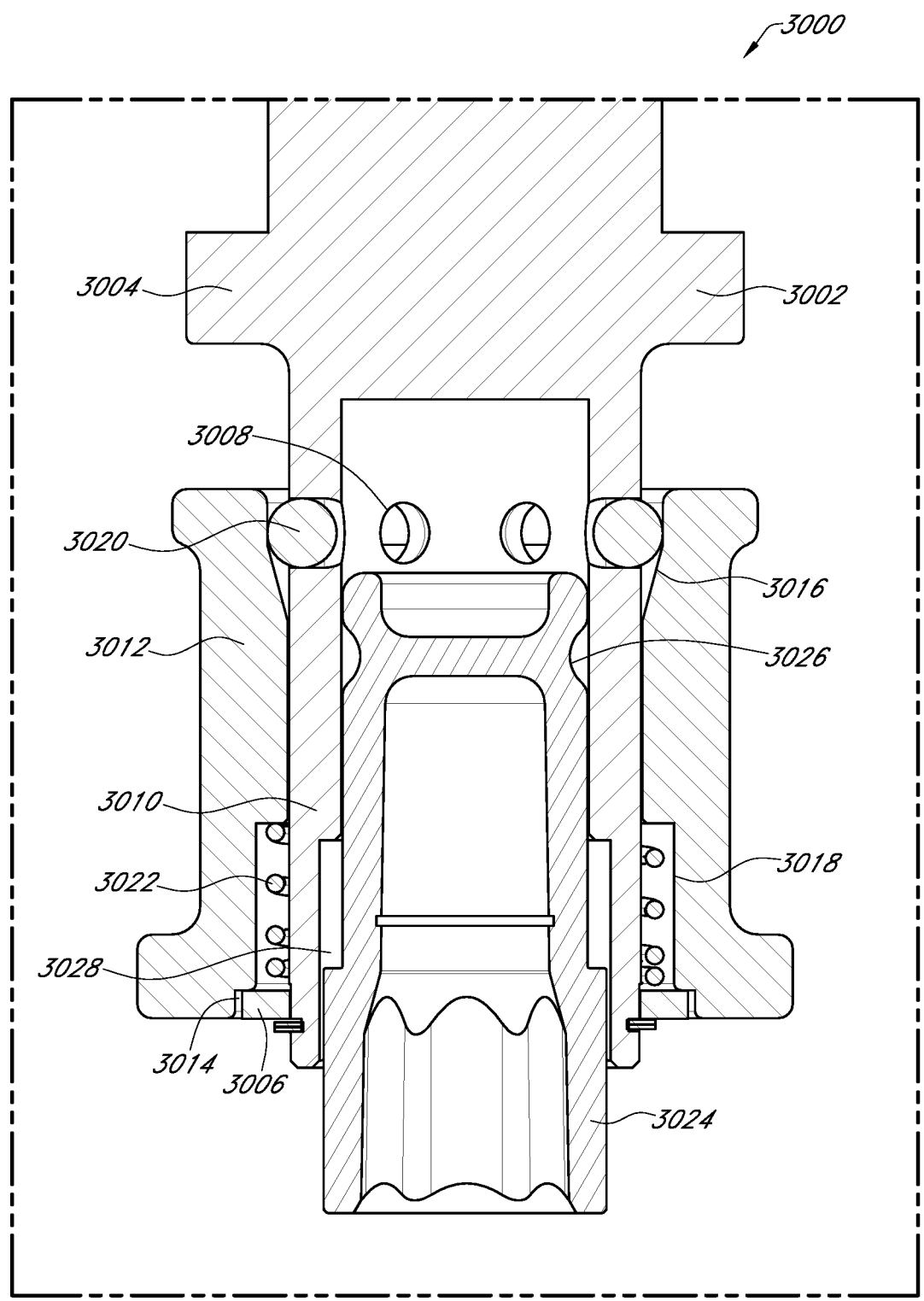
FIG. 30 illustrates a locking sleeve 3000 in accordance with one embodiment.
Figure 31:
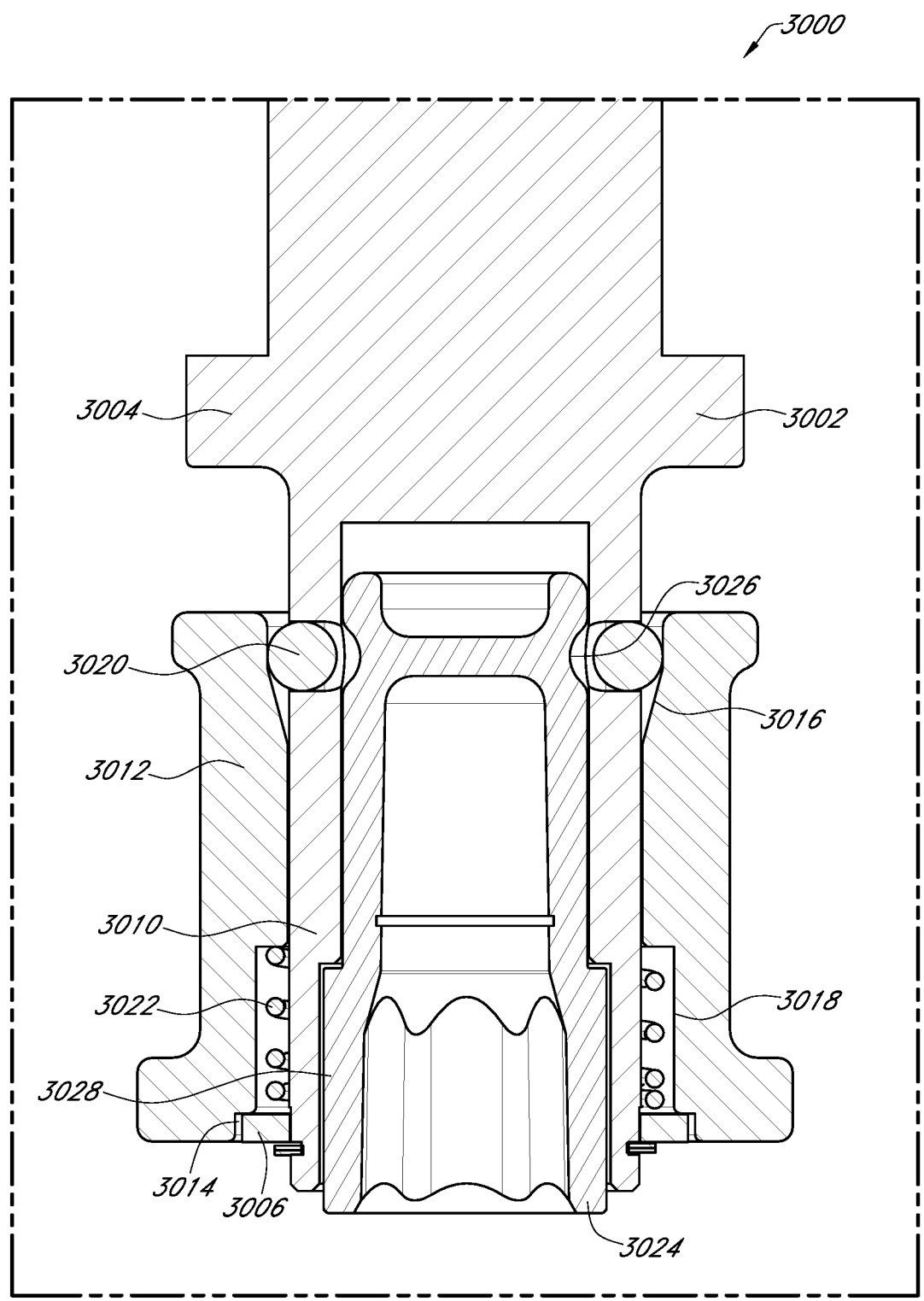
FIG. 31 illustrates a locking sleeve 3100 in accordance with one embodiment.
Figure 32:
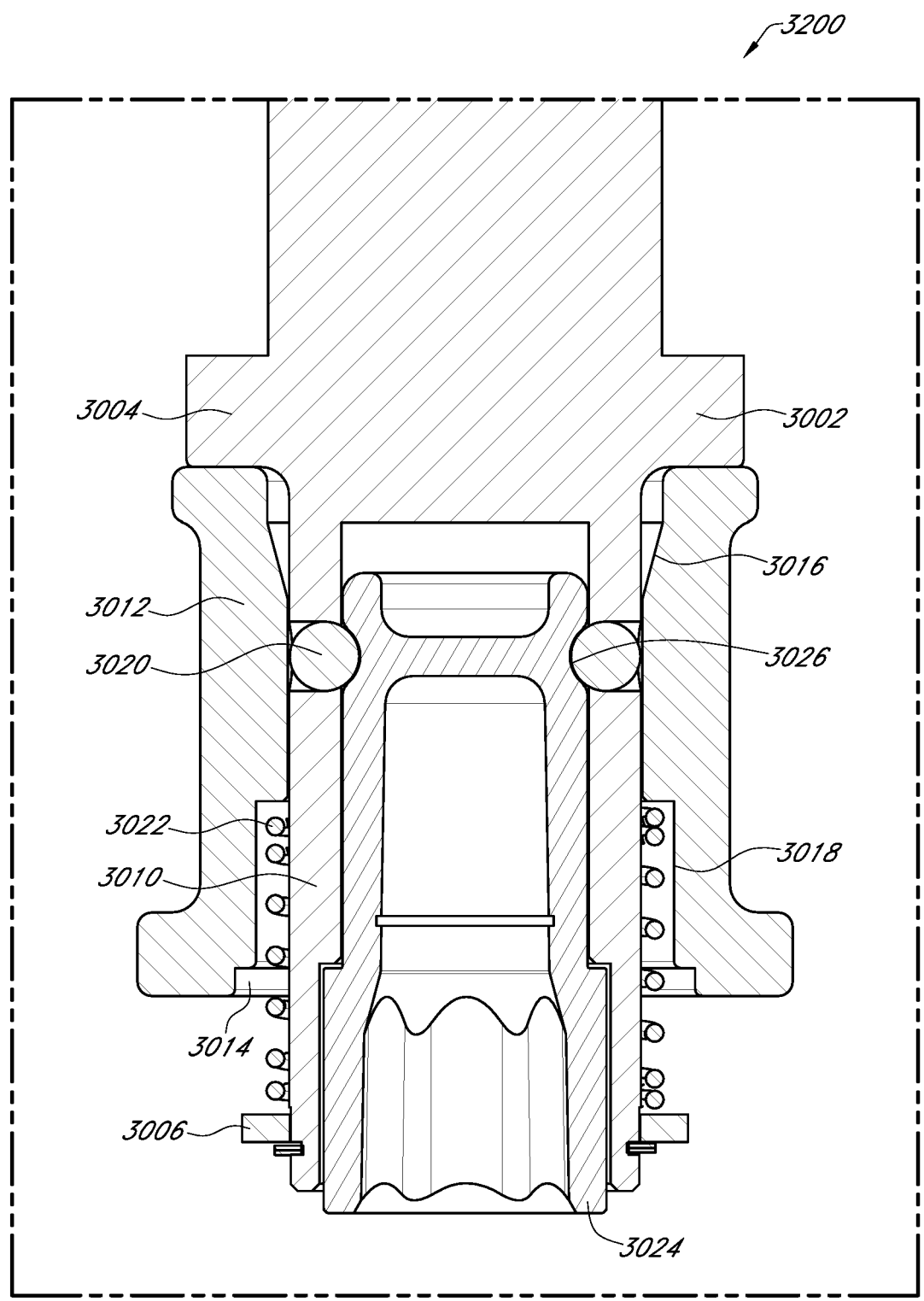
FIG. 32 illustrates a locking sleeve 3200 in accordance with one embodiment.

FIGS. 30, 31, and 32 illustrate a locking sleeve 3000 according to various embodiments. In various embodiments, a collar 3012 fits over a receiver 3002 and moves between a collar 3012 and a spring stop 3006.

FIG. 30 illustrates an embodiment where the collar 3012 has been pulled toward the spring stop 3006 and a notch 3014 on the collar 3012 abuts the spring stop 3006 located on the receiver 3002. In such a position the locking sleeve 3000 is positioned to accept a drive shaft 3024. In various embodiments, the drive shaft 3024 may then be inserted into the receiver 3002 until an edge 3028 abuts a drive shaft stop 3010. In various embodiments, the open configuration allows a set of locking balls 3020 to travel through the tapered opening 3008 toward a depression 3016 in the collar 3012, thereby, allowing entry of the drive shaft 3024 into the receiver 3002. In various embodiments, a user must apply a downward force to the collar 3012 to counteract the force generated by the spring 3022 located in the spring recess 3018. In various embodiments, the spring 3022 exerts a force that positions the collar and receiver relative to one another as shown in FIG. 32.

In various embodiments, once the drive shaft 3024 has been positioned as shown in FIG. 31, the user may release the collar 3012 and the spring 3022 may then push the collar 3012 upward and drive the locking balls 3020 into the shaft recesses 3026, thereby, locking the drive shaft into the locking sleeve 3000 allowing for rotational communication with the motor 2704. In various embodiments, the spring 3022 ensures that the receiver 3002 and collar 3012 stay in their closed and locked position.

A skilled artisan will appreciate that there are many ways to place a drive shaft 3024 in rotational communication with a motor 2704. In some embodiments, the drive shaft 3024 may be bolted to a drive shaft on the motor 2704 or a pin and sleeve mechanism may be used. The system and method disclosed above requires no additional parts or tools by the user however.

Figure 33:
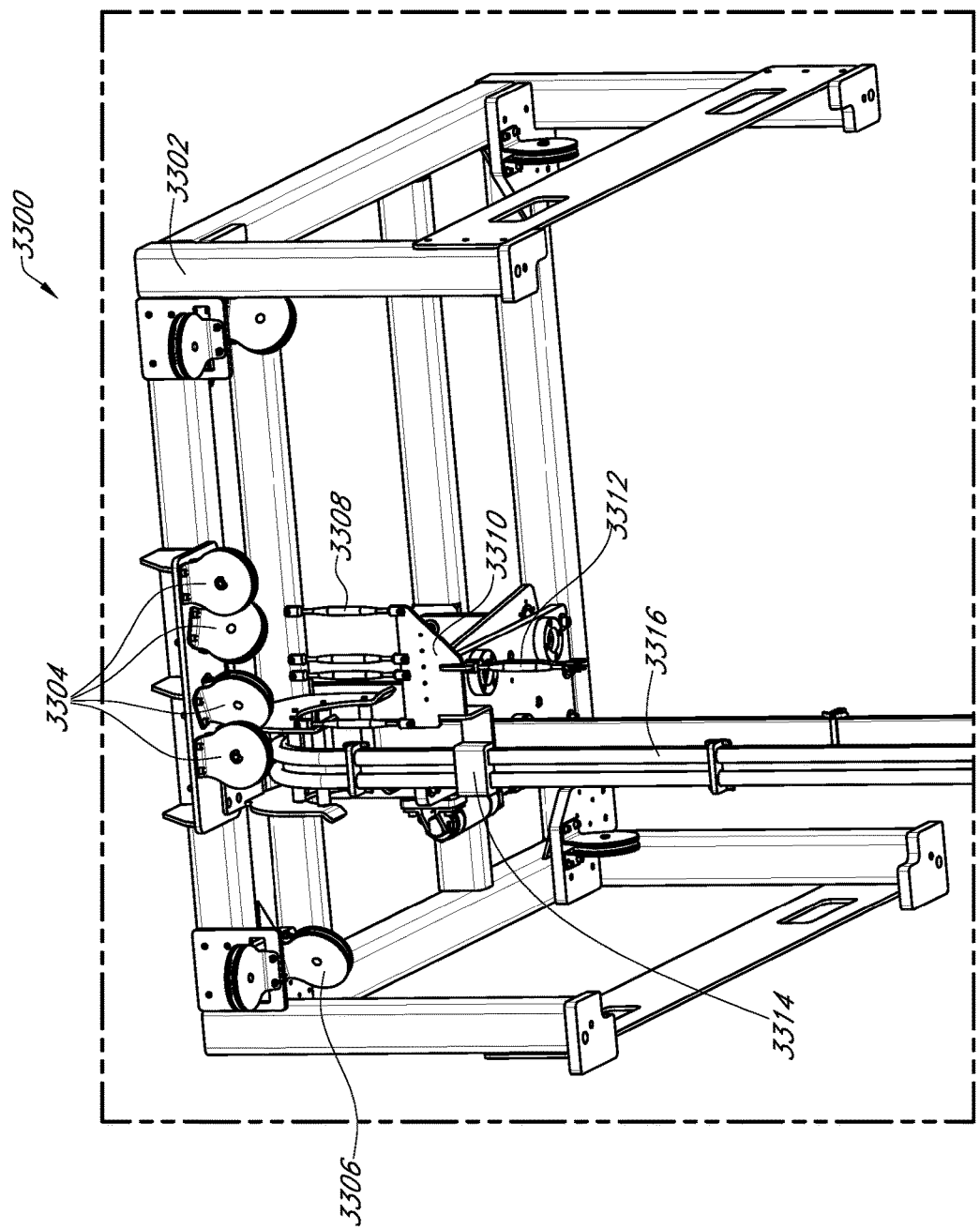
FIG. 33 illustrates a lift system 3300 in accordance with one embodiment.

FIG. 33 illustrates a lift system 3300 comprising a framework 3302, a routing pulleys 3304, a suspension pulley 3306, a turnbuckle 3308, a connection plate 3310, a connection plate buckle 3312, a connection plate bracket 3314, and a power cable 3316.

In various embodiments, cable 1600 is routed from the moveable platform 130 to suspension pulleys 3306 that may then be routed to routing pulleys 3304. In some embodiments, the cable extending from the routing pulleys 3304 may connect to turnbuckles 3308 that are attached to a connection plate designed to integrate the various cables 1600 into a single or parallel cables coming off one or more connection plate buckles 3312 mounted to the connection plate 3310. In various embodiments, the connection plate 3310 may be mounted to the power cable 3316 by a connection plate bracket 3314. In various embodiments, the power cable 3316 and connection plate 3310 move at the same rate while the moveable platform 130 is in motion and being drive by the motive force device 106. In various embodiments, the connection plate turnbuckles 3414 route the cable 1600 from the connection plate 3410 to the motive force device 106.

Figure 34:
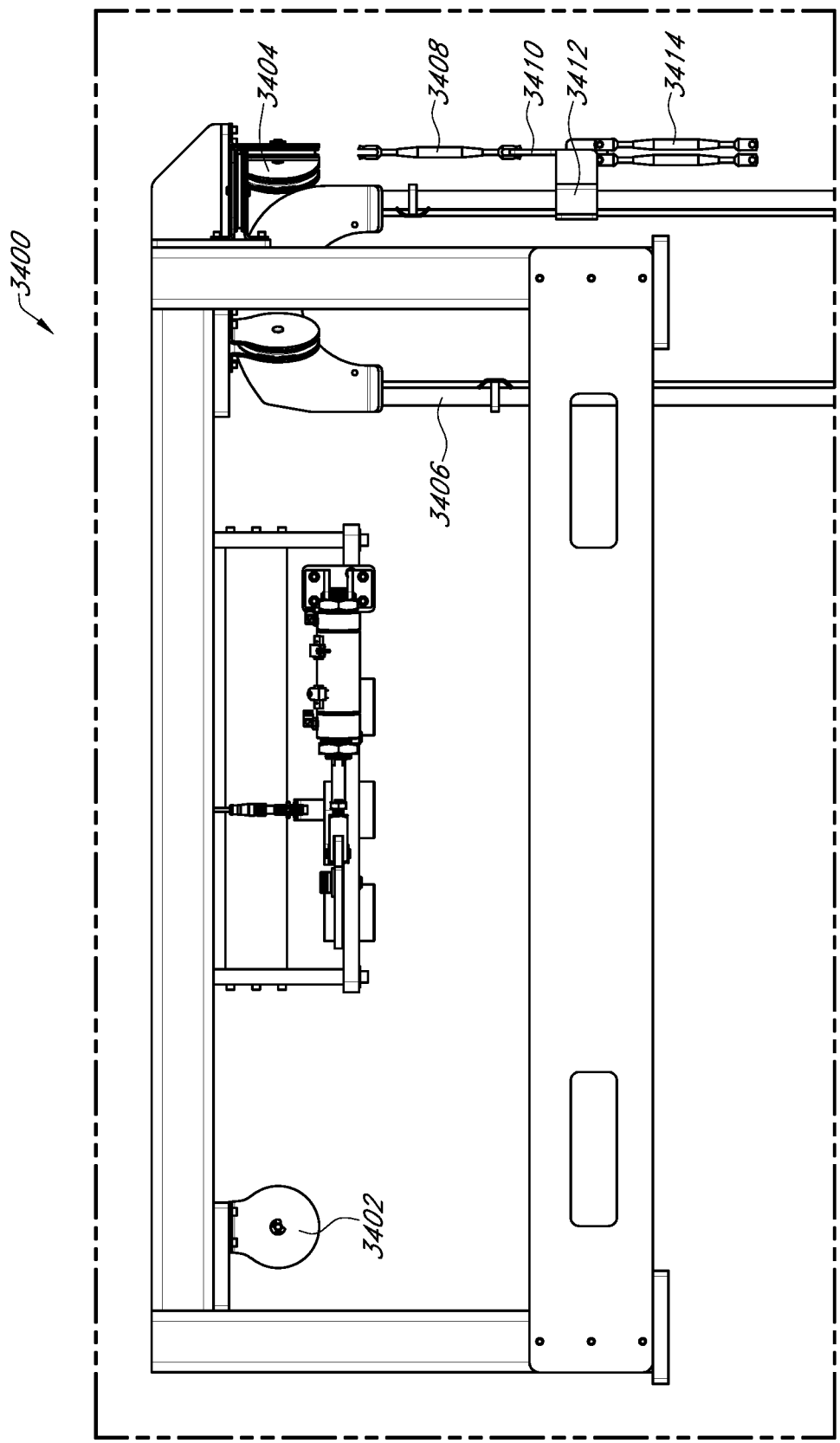
FIG. 34 illustrates a lift system 3400 in accordance with one embodiment.

FIG. 34 illustrates a lift system 3400 from a side view comprising a suspension pulley 3402, a routing pulley 3404, a power cable 3406, a turnbuckles 3408, a connection plate 3410, a connection plate bracket 3412, and a connection plate turnbuckles 3414 according to the same embodiment as shown in FIG. 33.

Figure 35:
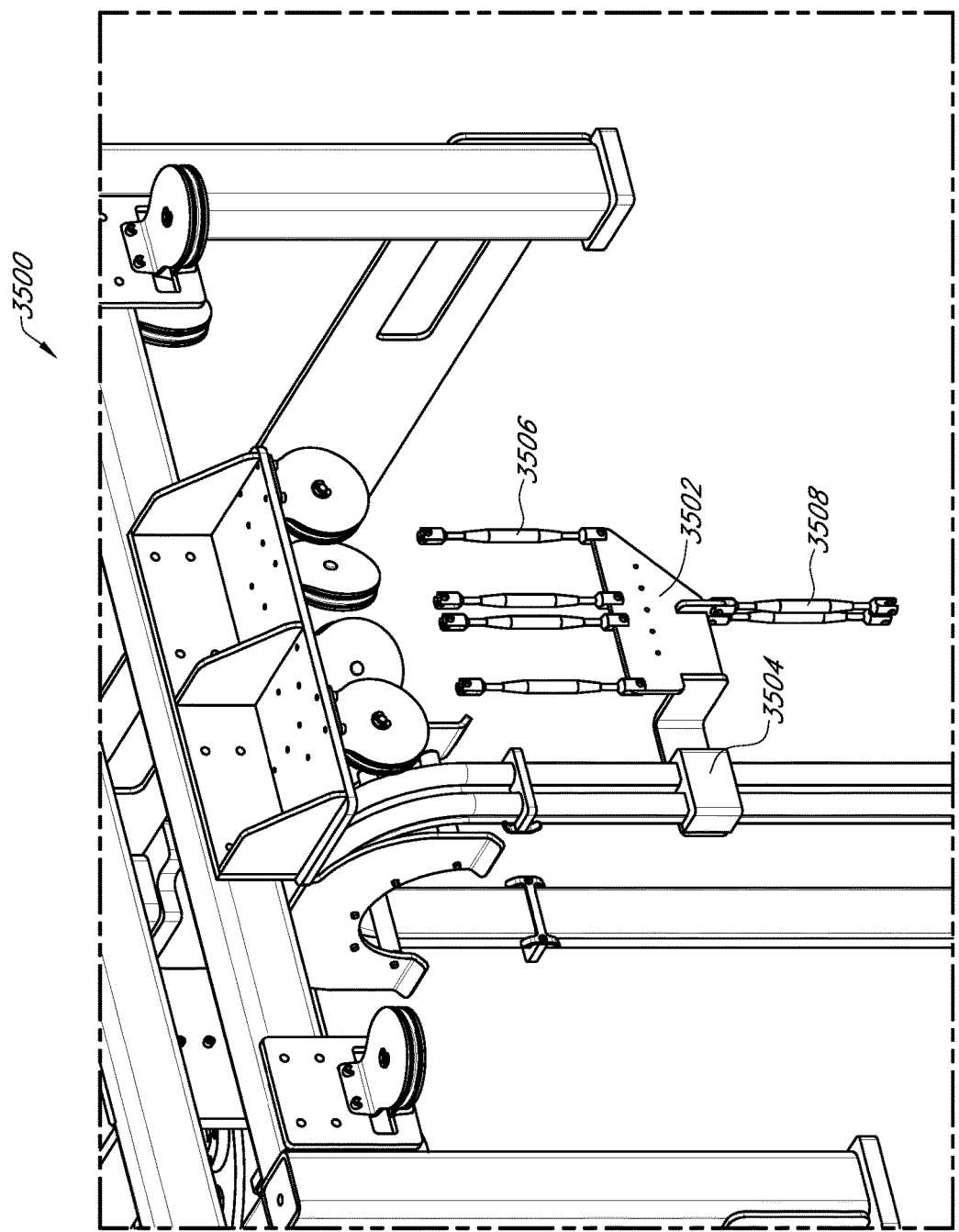
FIG. 35 illustrates a lift system 3500 in accordance with one embodiment.

FIG. 35 illustrates a lift system 3500 comprising a connection plate 3502, a connection plate bracket 3504, a turnbuckles 3506, and a connection plate turnbuckles 3508 in a close up view according to the same embodiment as shown in FIGS. 33 and 34.

Figure 36:
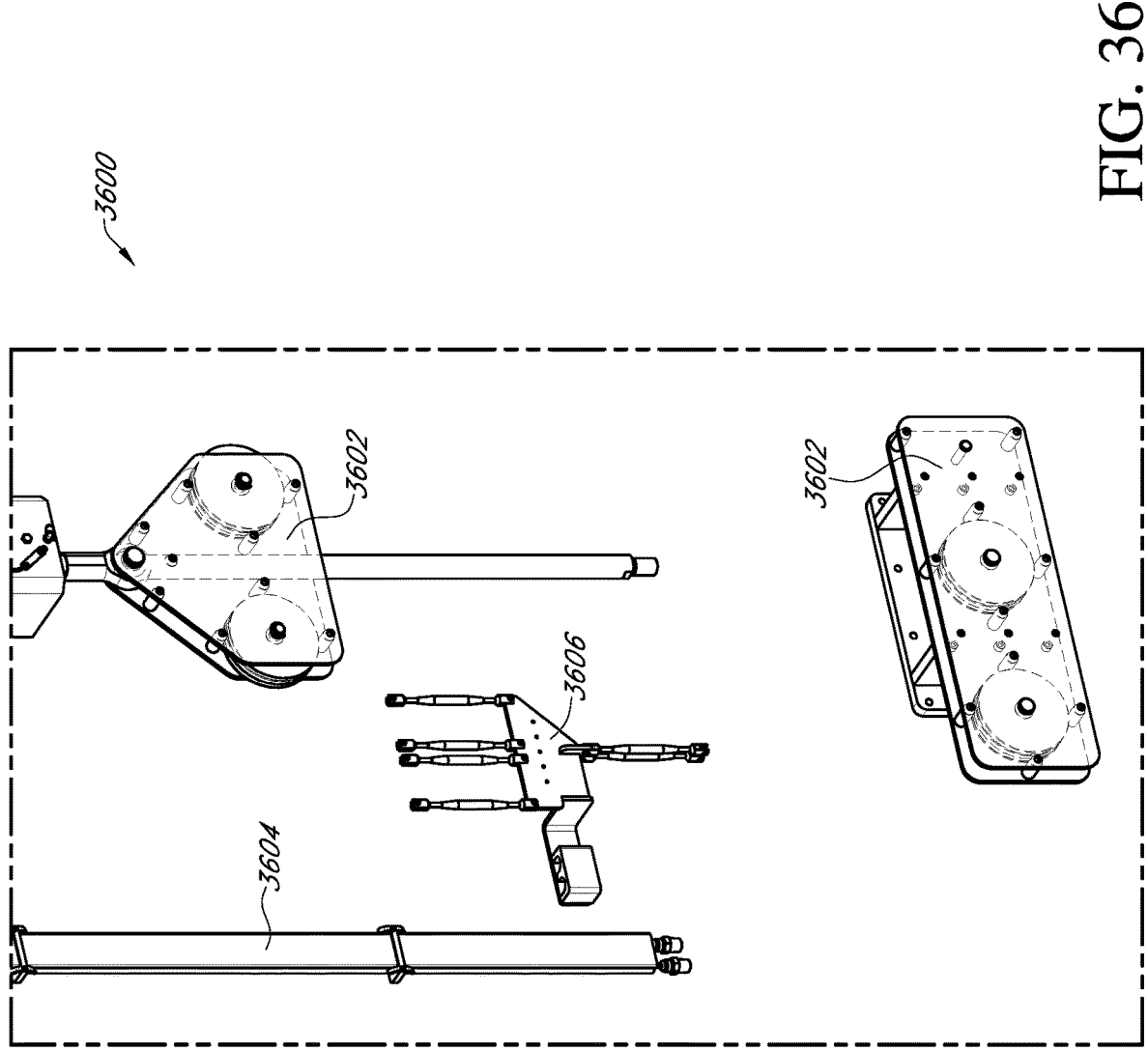
FIG. 36 illustrates a lift system 3600 in accordance with one embodiment.

FIG. 36 illustrates individual components of the lift system 3600 shown and described previously. The motive force device 106 operably connects to the ratio pulley system 3602 through cables 1600 to decrease the load in various embodiments. In some embodiments, the ratio pulley system 3602 decreases the load four to one. A power cable 3604 and a cable connection plate assembly 3606 are depicted according to various embodiments.

Figure 37:
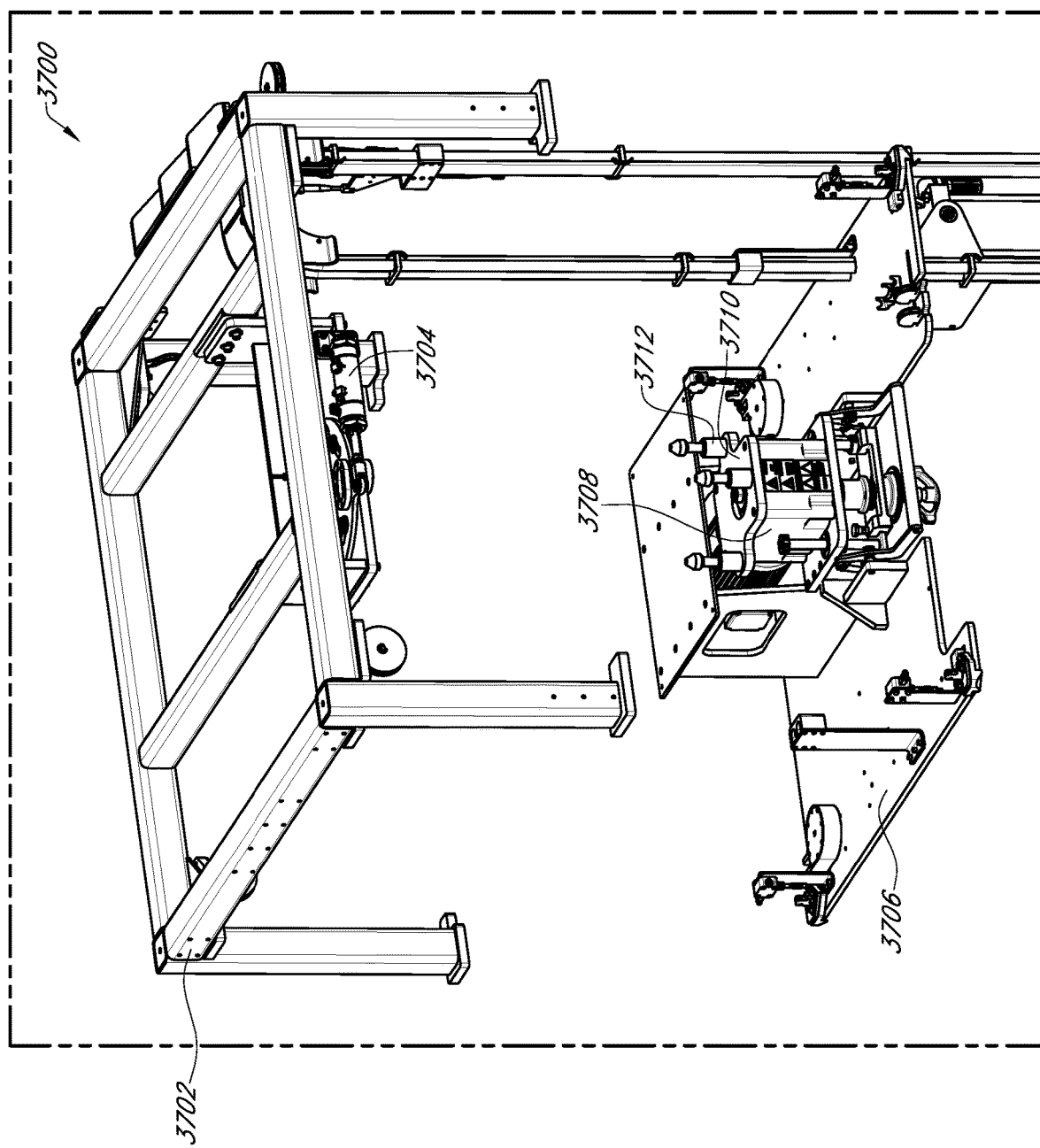
FIG. 37 illustrates a rigid housing 3700 in accordance with one embodiment.

FIG. 37 illustrates a rigid housing 3700 comprises a framework 3702 having a moveable platform securing assembly 3704 mounted thereto and a moveable platform 3706 including a motor 3708, a motor plate 3710, and a protrusion 3712.

In various embodiments, the motor 3708 as described in several figures may include a motor plate 3710 mounted onto an upper region and the motor plate 3710 may include one or more protrusions 3712. In various embodiments, the moveable platform 3706 may move to the top of the framework 3702 and the protrusions 3712 may enter a moveable platform securing assembly 3704 where their movement may be restricted. In some embodiments, restricting the movement of the protrusions 3712 may act to secure the entire moveable platform 3706 and the flexible container 400, 502, 600 secured to it. Once the protrusions 3712 are locked in place installation is complete and a bioproduction process can begin.

Figure 38:
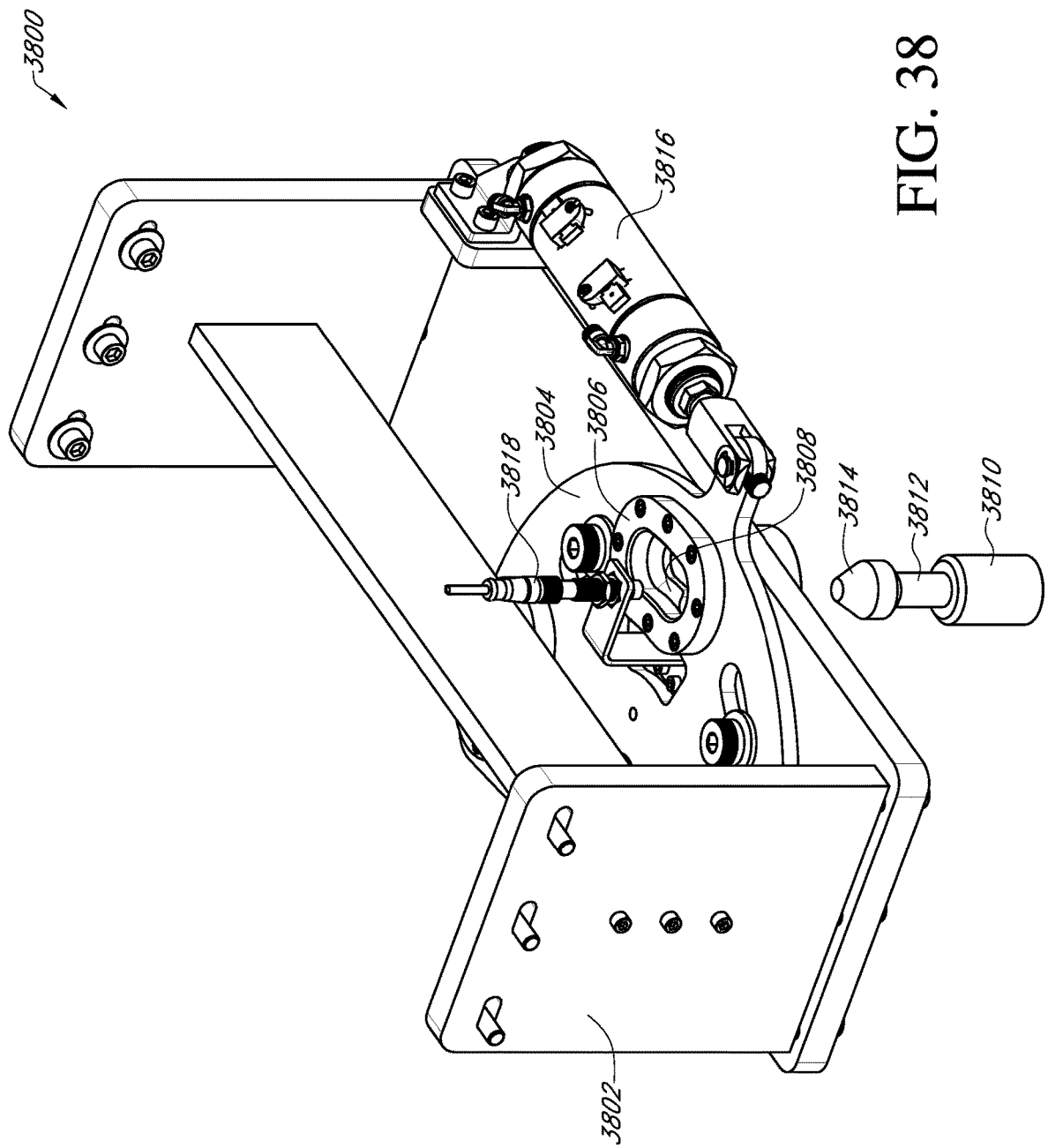
FIG. 38 illustrates a moveable platform securing assembly 3800 in accordance with one embodiment.
Figure 39:
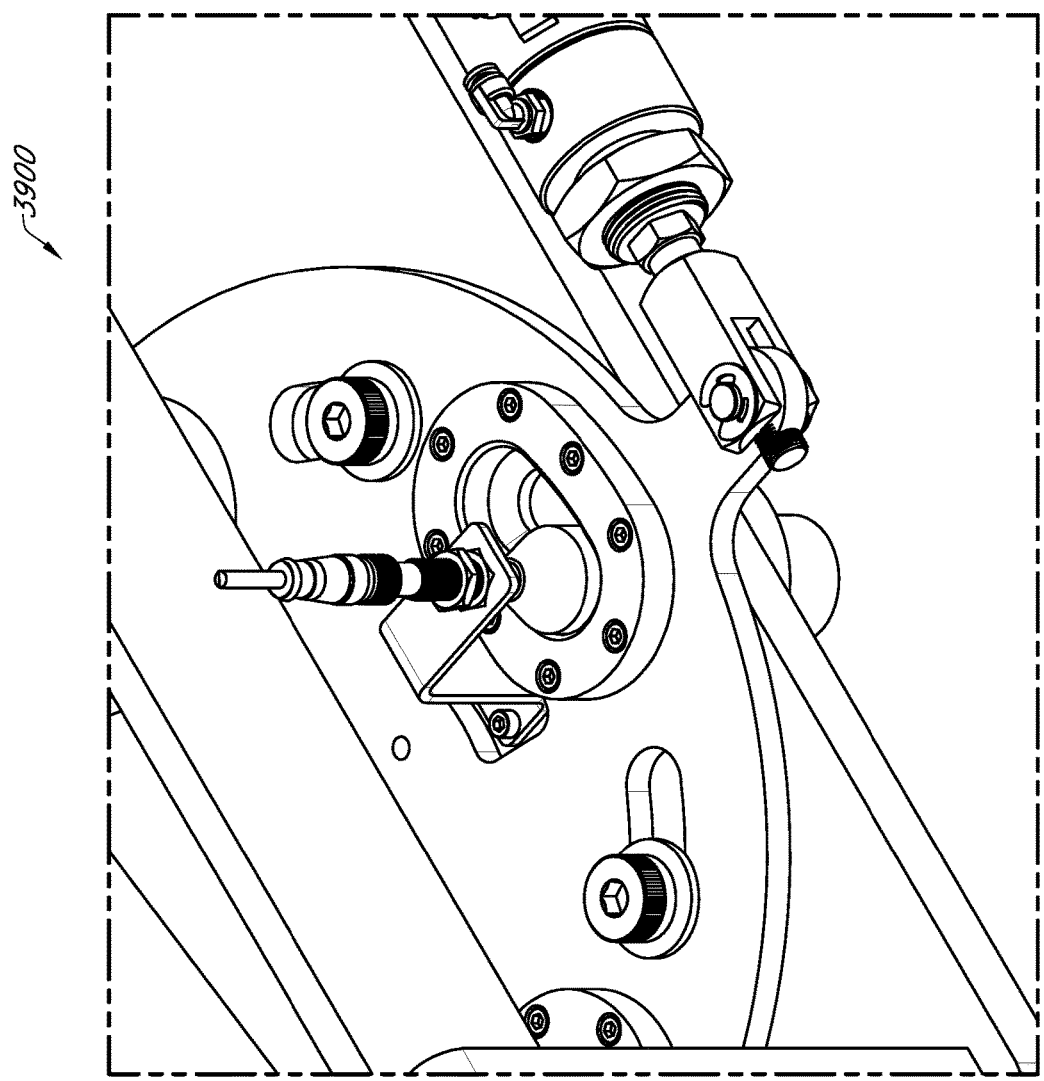
FIG. 39 illustrates a moveable platform securing assembly 3900 in accordance with one embodiment.
Figure 40:
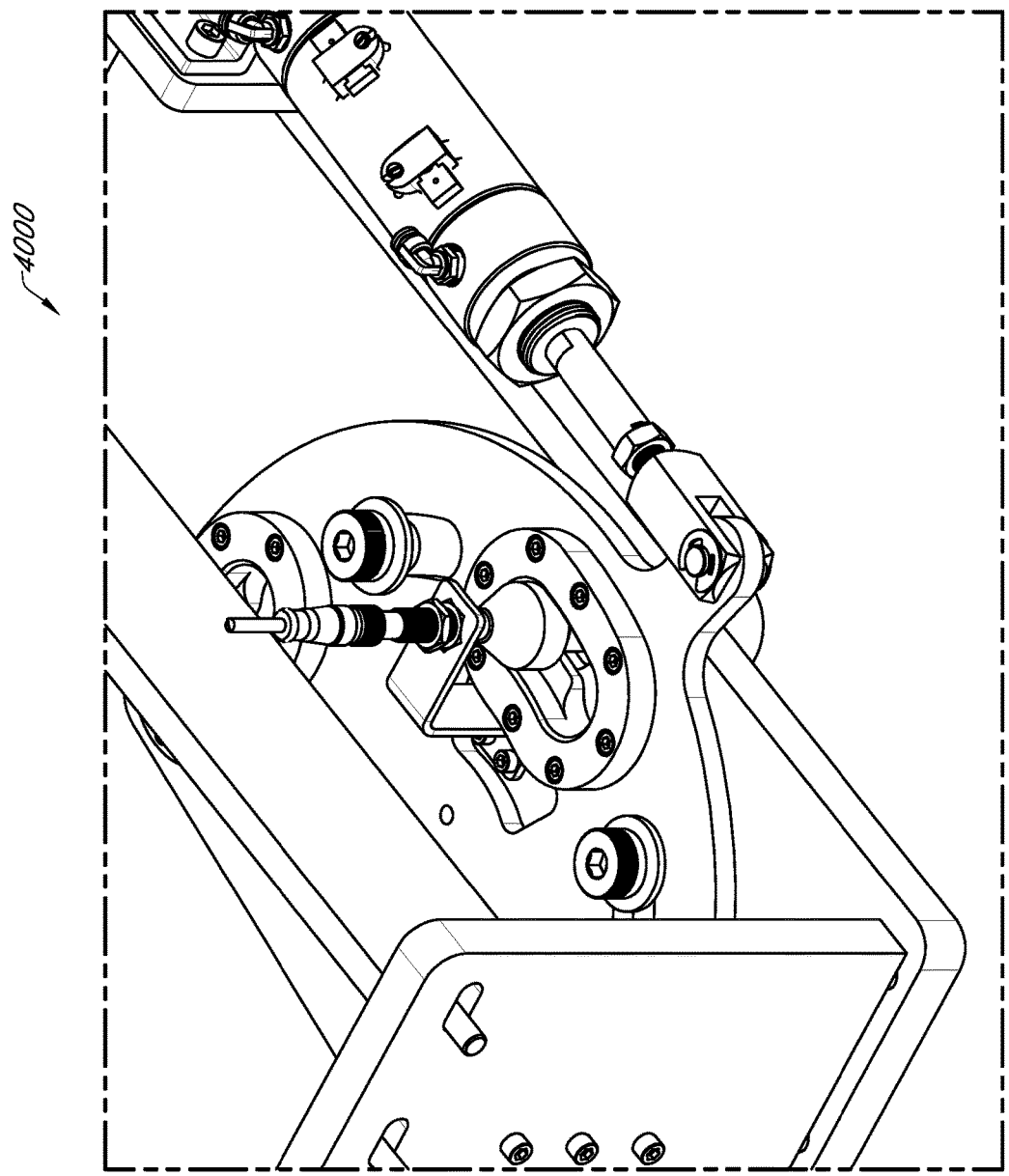
FIG. 40 illustrates a moveable platform securing assembly 4000 in accordance with one embodiment.

FIGS. 38, 39, and 40 illustrate a moveable platform securing assembly 3800 according to various embodiments. The moveable platform securing assembly 3800 may comprises a securing bracket 3802, a receiver plate 3804, a protrusion receiver 3806, a tapered opening 3808, a protrusion 3810, a recess 3812, a head 3814, and an actuator 3816.

In various embodiments, a securing bracket 3802 may be mounted to the framework 3702 and include a rotatable receiver plate 3804. In some embodiments, the receiver plate 3804 may include one or more protrusion receivers 3806. In various embodiments a protrusion receiver 3806 may be adapted to receive and secure a protrusion 3810 extending away from a motor plate 3710.

FIG. 38 illustrates a receiver plate 3804 in an open configuration that is ready to accept a protrusion 3810. The protrusion receiver 3806 may include a tapered opening 3808 which includes a narrow portion and a wide portion. In the open configuration the protrusion 3810 may be aligned with the wide portion of the protrusion receiver 3806.

FIG. 39 illustrates an embodiment where the moveable platform 3706 has been raised to position the protrusion 3810 into the protrusion receiver 3806 in its open configuration. In some embodiments, a sensor 3818 may detect the presence of a protrusion 3810 and enable the actuator 3816. An operator may manually activate an actuator 3816, it may be done from the controller 2102 or HMI 132, or the actuator 3816 may be triggered remotely.

FIG. 40 illustrates an embodiment in which the actuator 3816 has been activated and has rotated the receiver plate 3804 such that the tapered opening 3808 of the protrusion receiver 3806 has caused the narrow portion of the protrusion receiver 3806 to engage the protrusion 3810, thereby, locking the moveable platform 3706 in place.

A skilled artisan will appreciate that there are many ways to secure the moveable platform 3706 for bioproduction processes. For example, support beams from a rigid housing may slide into recesses on the moveable platform 3706 or some other similar method of physical restraint may be used. The moveable platform securing assembly 3800 described herein is a simple system and method that requires no additional parts and a single operator may engage the system without use of a lot of force.

Figure 41:
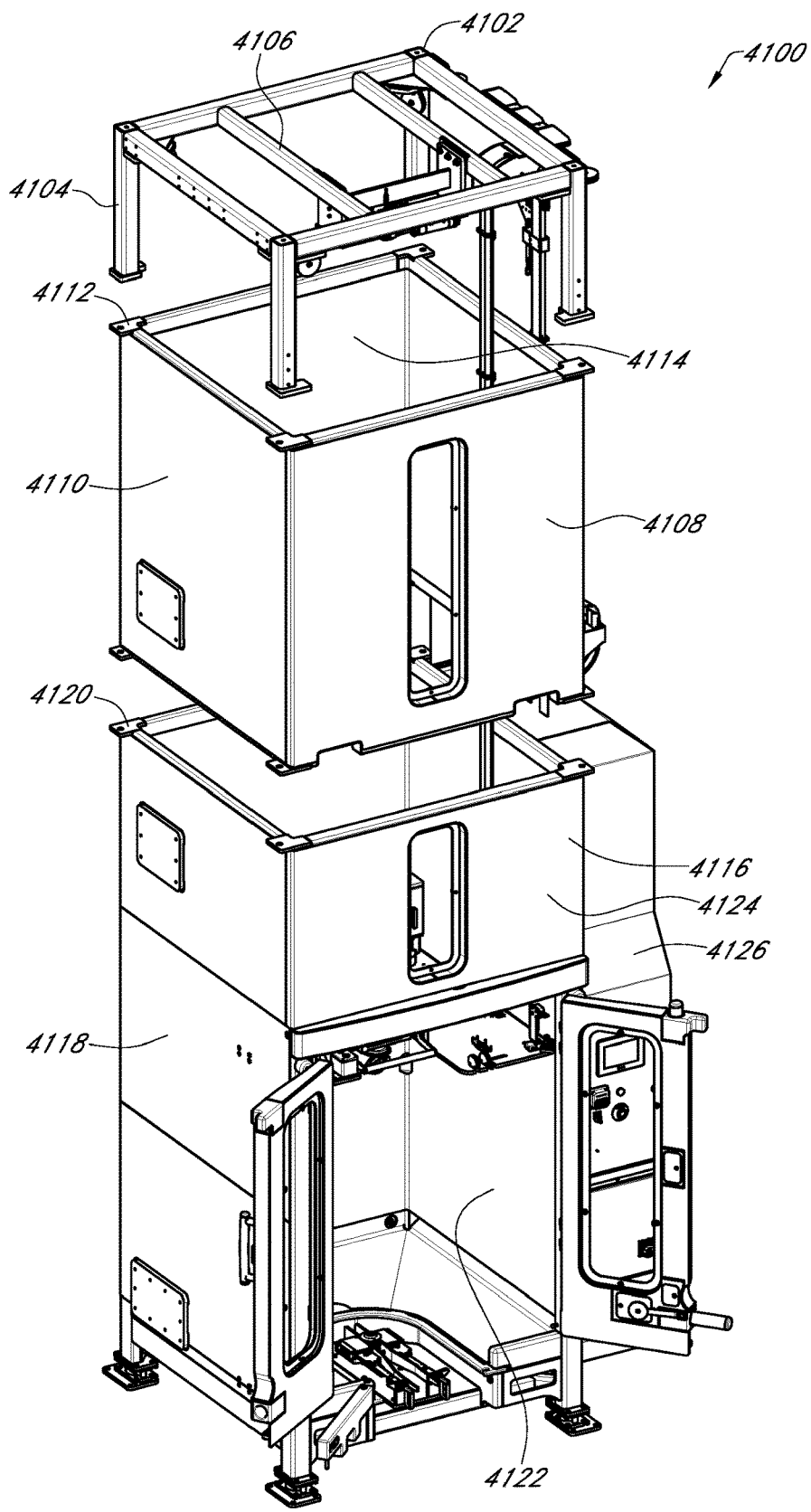
FIG. 41 illustrates a rigid housing 4100 in accordance with one embodiment.

FIG. 41 illustrates a rigid housing 4100 comprising a framework 4102, an expander 4108, and a base 4116.

In various embodiments, a framework 4102 may be comprised of one or more legs 4104 supporting a set of beam 4106. In various embodiments, an expander 4108 may include a sidewall 4118 encircling an interior 4114 and the edges 4112 may bound openings at either end of the sidewall 4110. In various embodiments, a base 4116 may include a sidewall 4118 encircling an interior 4122. In some embodiments, the combined expander 4108 and base 4116 result in a larger interior space. In some embodiments, a control system 4126 may be mounted to the exterior 4124 of the base 4116, expander 4108, or both.

In various embodiments, a framework 4102 may include one or more legs 4104 with one end attached to one or more beams 4106 and an opposing end configured to connect to either an edge 4112 of an expander 4108 portion or an edge 4120 of a base 4116 portion. In some embodiments, a smaller or entry level volume may be desirable for a bioproduction process. In such embodiments, the framework 4102 may connect directly to the base 4116 and the amount of cable 1600 used may be less than when an expander 4108 portion is used.

In various embodiments, a framework 4102 may connect to an edge 4112 of an expander 4108 and an opposing edge 4112 on the expander may connect to a base 4116. In such an embodiment, the volume of the rigid housing 4100 is increased which will require that a larger flexible container 400, 502, 600 be used in the system. In some embodiments, a user may wish to install the framework 4102 to a base 4116 until production requirements increase. At that time, the user may then purpose the expander 4108 portion and disassemble the framework 4102 from the base 4116 and then insert the expander 4108 in between. In some embodiments, the reverse may occur where the expander 4108 unit may need to be removed due to a new production process requiring less volume or lower demand for a certain product.

Figure 42:
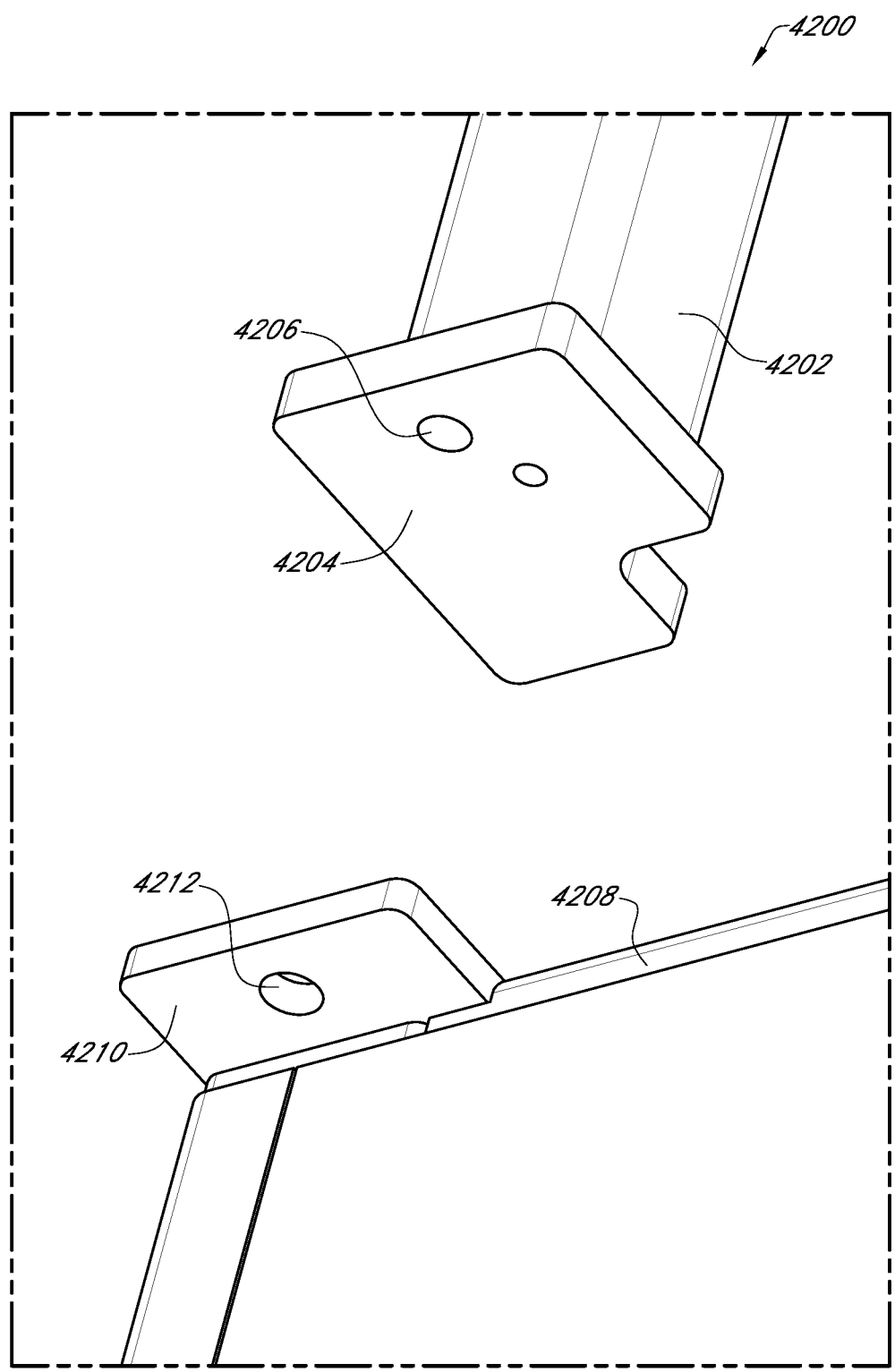
FIG. 42 illustrates a rigid housing 4200 in accordance with one embodiment.

FIG. 42 illustrates a rigid housing 4200 comprises a leg 4202, a connector plate 4204, an opening 4206, an edge 4208, a connector plate 4210, and an opening 4212 according to various embodiments. In various embodiments, a leg 4202 from the framework 4102 may include a connector plate 4204 including one more openings 4206. In various embodiments, an edge 4208 extending from either a base 4116 or an expander 4108 may include a connector plate 4210 having one or more openings 4212. In various embodiments, the openings 4206, 4212 may be aligned and a bolt, screw, or rod may be used to secure the leg 4202 and edge 4208 to one another. A skilled artisan will appreciate that there are many ways to join two objects that may include weld, adhesive, clips, pins, or any other device or joining system or method known.

Figure 43:
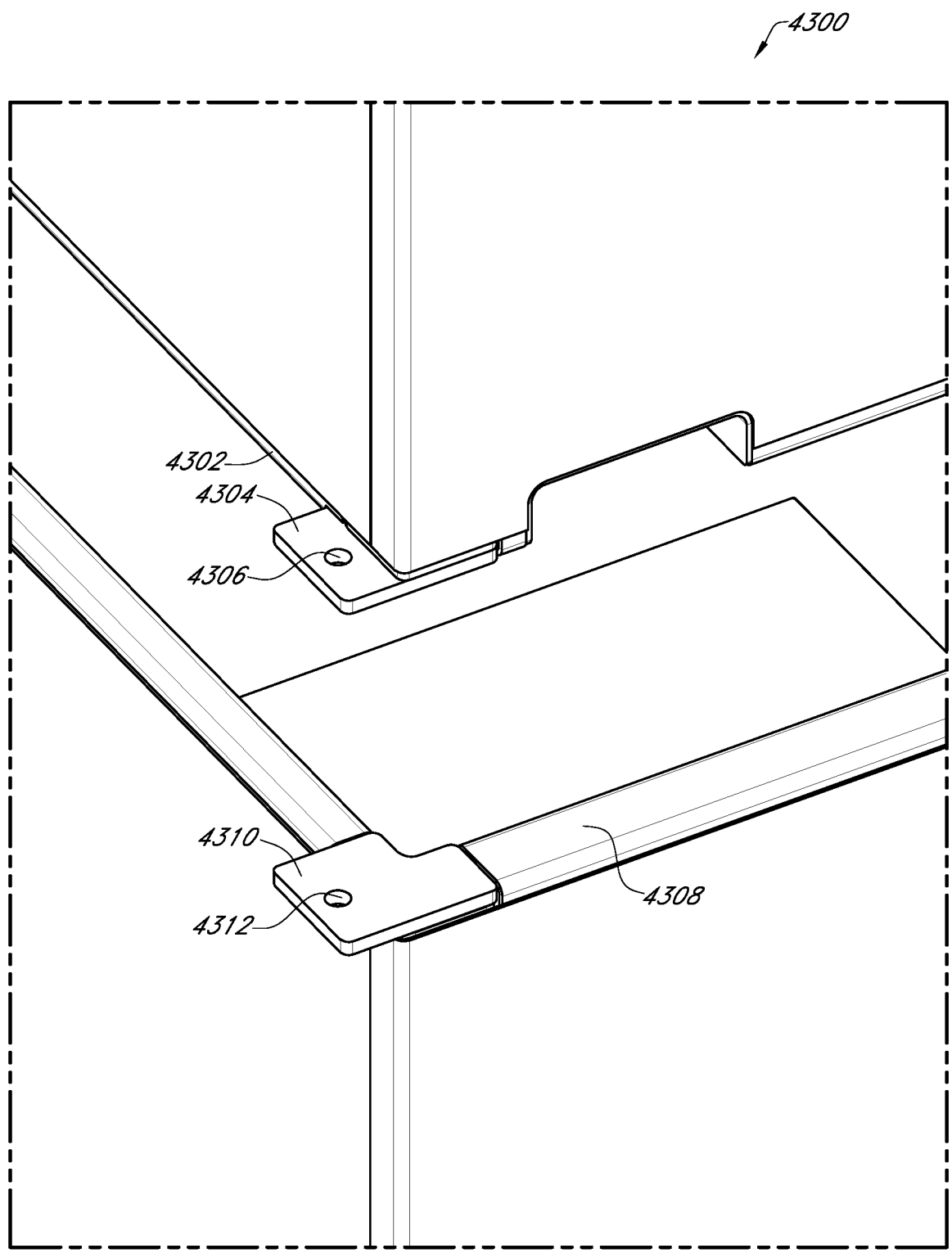
FIG. 43 illustrates a rigid housing 4300 in accordance with one embodiment.

FIG. 43 illustrates a rigid housing 4300 comprising an edge 4302 having a connector plate 4304 with an opening 4306 and another edge 4308 having a connector plate 4310 with an opening 4312. Similarly to FIG. 2, various embodiments may include bringing the two edges 4302, 4308 in close proximity and aligning the openings 4306, 4312 of the connector plates 4304, 4310 and joining them by inserting a screw, bolt, pin, or other such device through the openings and securing them with a nut, solder, adhesive, or something else. There are many ways to join two edges as the skilled artisan will appreciate.

Figure 44:
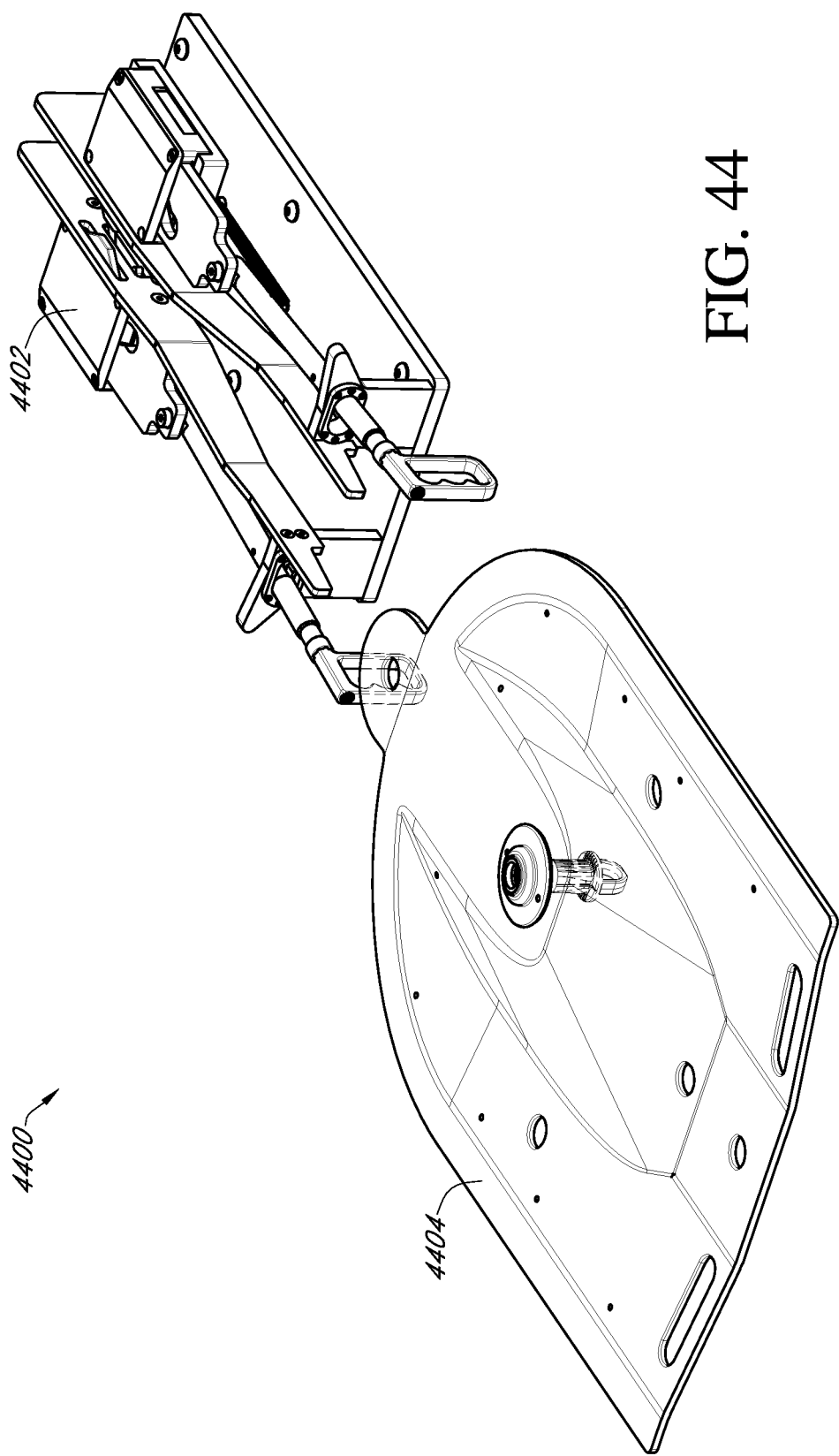
FIG. 44 illustrates a plate mount assembly 4400 in accordance with one embodiment.

FIG. 44 illustrates a plate mount assembly 4400 comprises a catch assembly 4402 and a tube management plate 4404 according to various embodiments. In this embodiment, the catch assembly 4402 is open and ready to receive the tube management plate.

Figure 45:
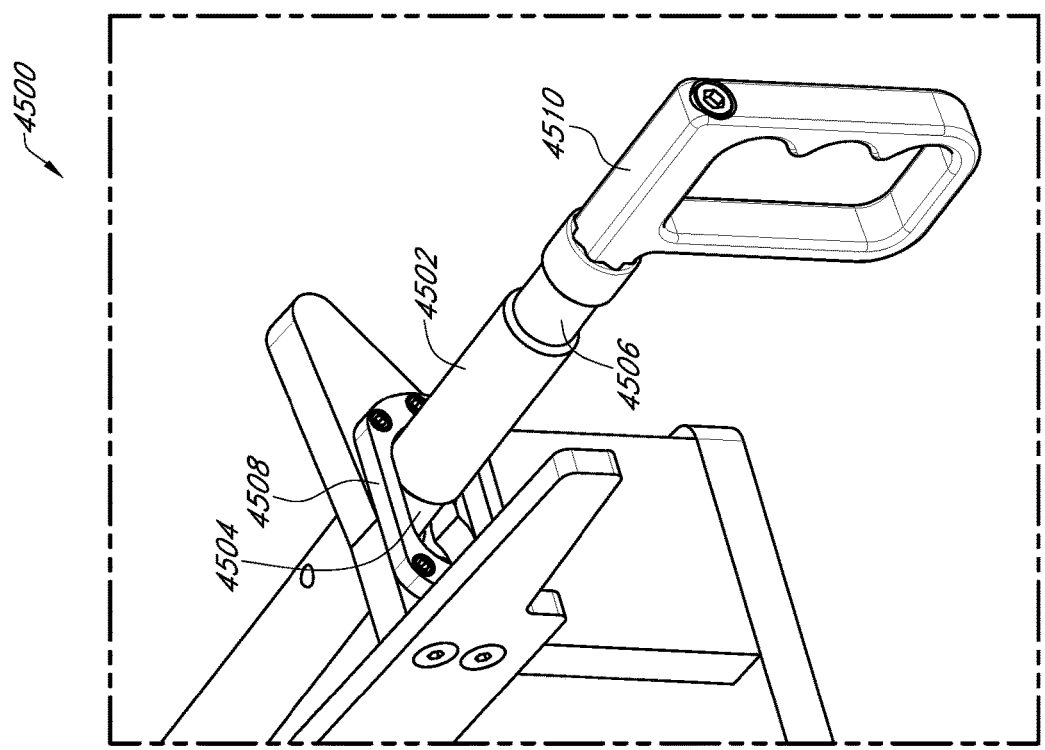
FIG. 45 illustrates an arm assembly 4500 in accordance with one embodiment.

FIG. 45 illustrates an arm assembly 4500 comprises a rod 4502, a second recess 4504, a first recess 4506, a tapered opening 4508, and a handle 4510 according to various embodiments.

In various embodiments, a rod extends through a tapered opening 4508 and have a first recess, a second recess, and a handle 4510 affixed to an end.

In various embodiments, the rod 4502 may be manipulated perpendicular to its longitudinal axis to move between two positions within the tapered opening 4508. In some embodiments, one of the two recesses 4504, 4506 may slide from a wide portion of the tapered opening 4508 and into a narrow portion 528. In some embodiments, the narrow portion of the tapered opening 4508 is narrower than the rod 4502 except in the recessed portions. Thus, the rod 4502 may be locked from moving longitudinally along its axis through interaction of the tapered opening 4508 and the recesses 4504, 4506.

In various embodiments, the handle 4510 extends into a location where the door 716 of the rigid housing 702 would enter in its closed position, thereby, prohibiting closure of the door 716. In some embodiments, the rod 4502 may only be pushed in to avoid inhibition of door 716 closure when a bearing housing is correctly positioned within the catch assembly 4402.

Figure 46:
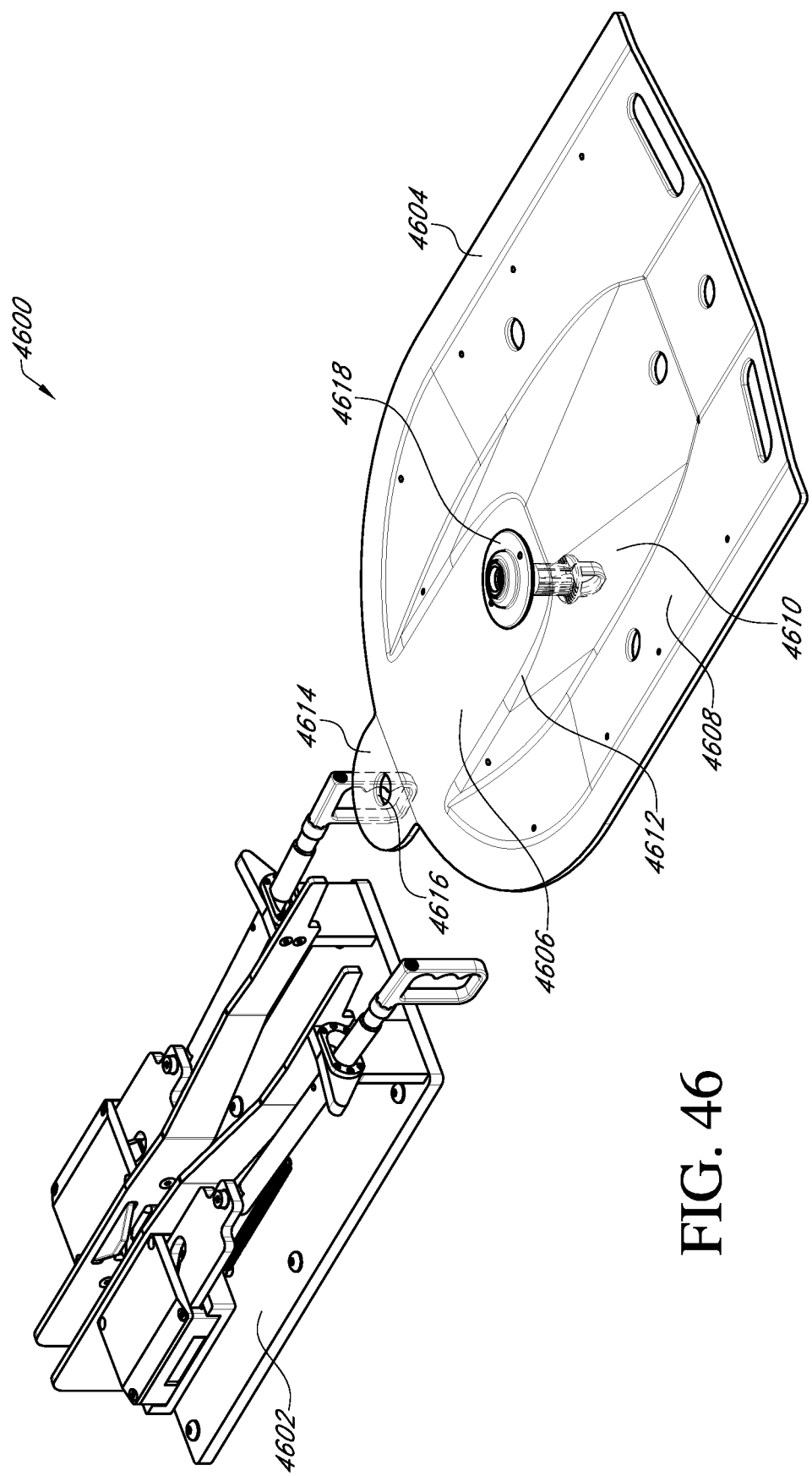
FIG. 46 illustrates a plate mount assembly 4600 in accordance with one embodiment.

FIG. 46 illustrates a plate mount assembly 4600 comprises a catch assembly 4602 in an open and ready to receive configuration and a tube management plate 4604 oriented to enter the catch assembly 4602.

In various embodiments, a tube management plate 4604 may include a first plane 4606 and a second plane 4608 joined by a joining surface 4610. In some embodiments, the tube management plate 4604 may include a plurality of structural supports 4612 connected to the planes and surfaces to provide support capable of withstanding downward pressure from a flexible container 400, 502, 600. The tube management plate 4604 my further include a tab 4614 having a tab opening 4616, and a bearing receiver 526 for positioning a bearing housing 4618 (flexible container not shown).

Figure 47:
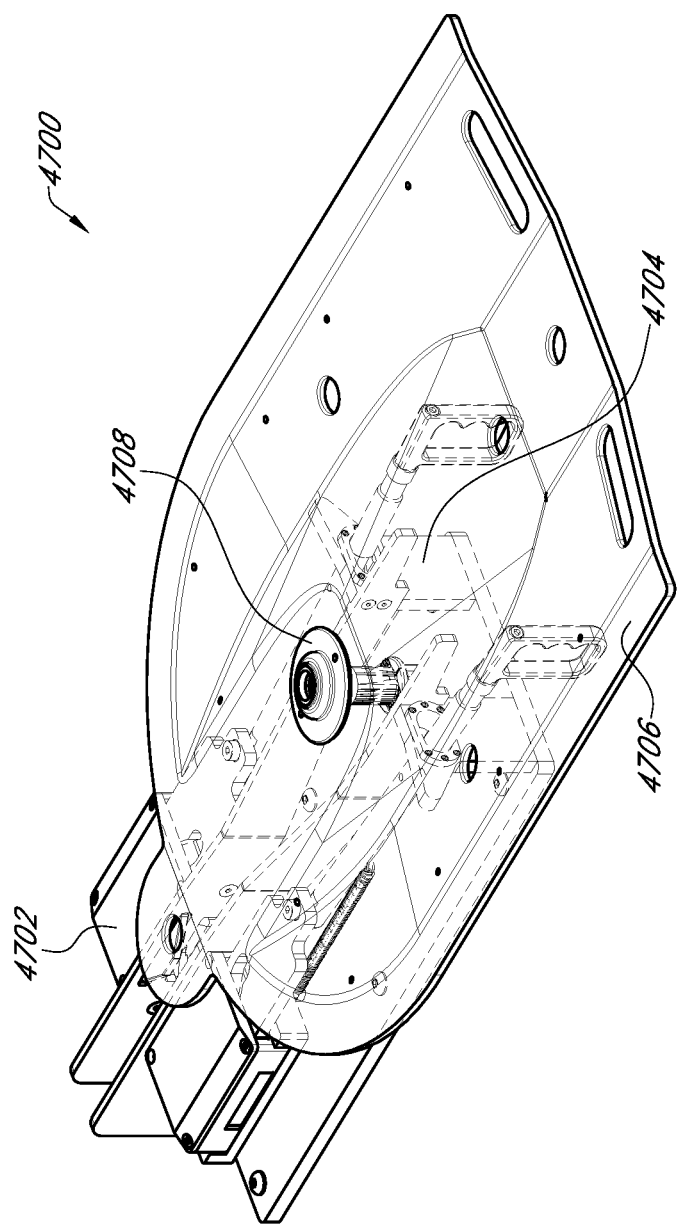
FIG. 47 illustrates a plate management assembly 4700 in accordance with one embodiment.

FIG. 47 illustrates a plate management assembly 4700 in its open and ready to receive configuration comprises a catch assembly 4702 including a set of a housing guides 4704 and a tube management plate 4706 including a bearing housing 4708 mounted thereto. In the embodiment shown in FIG. 47, an operator has slid the bearing housing 4708 part way into the housing guide 4704.

Figure 48:
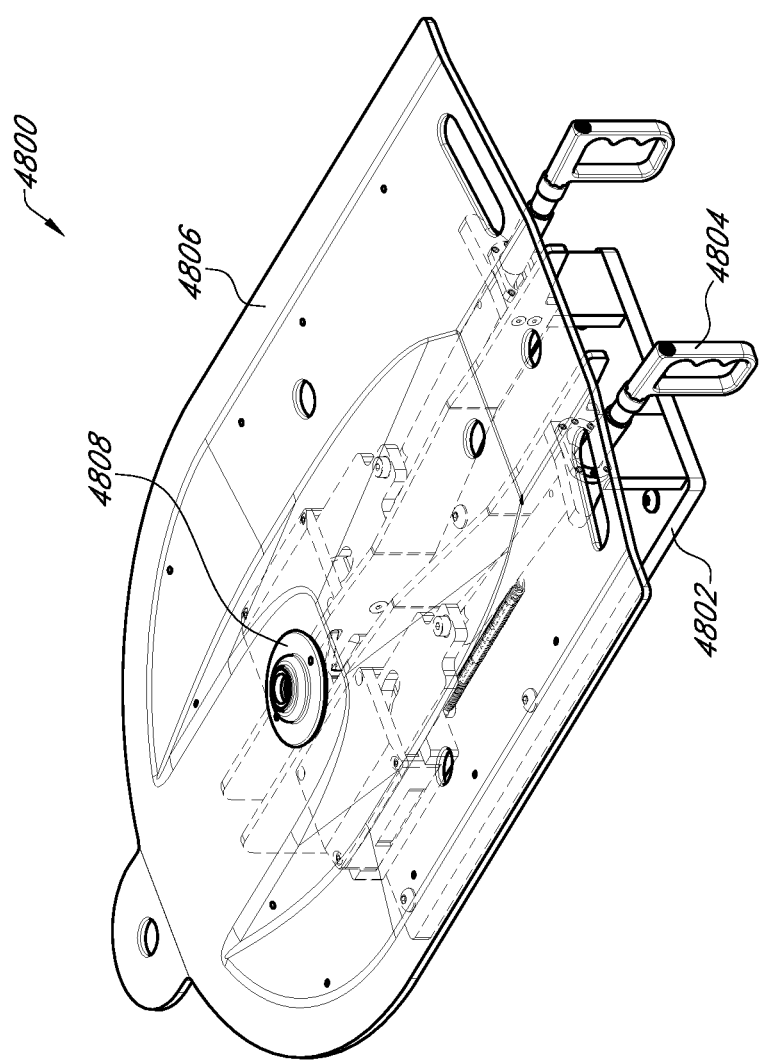
FIG. 48 illustrates a plate mount assembly 4800 in accordance with one embodiment.
Figure 49:
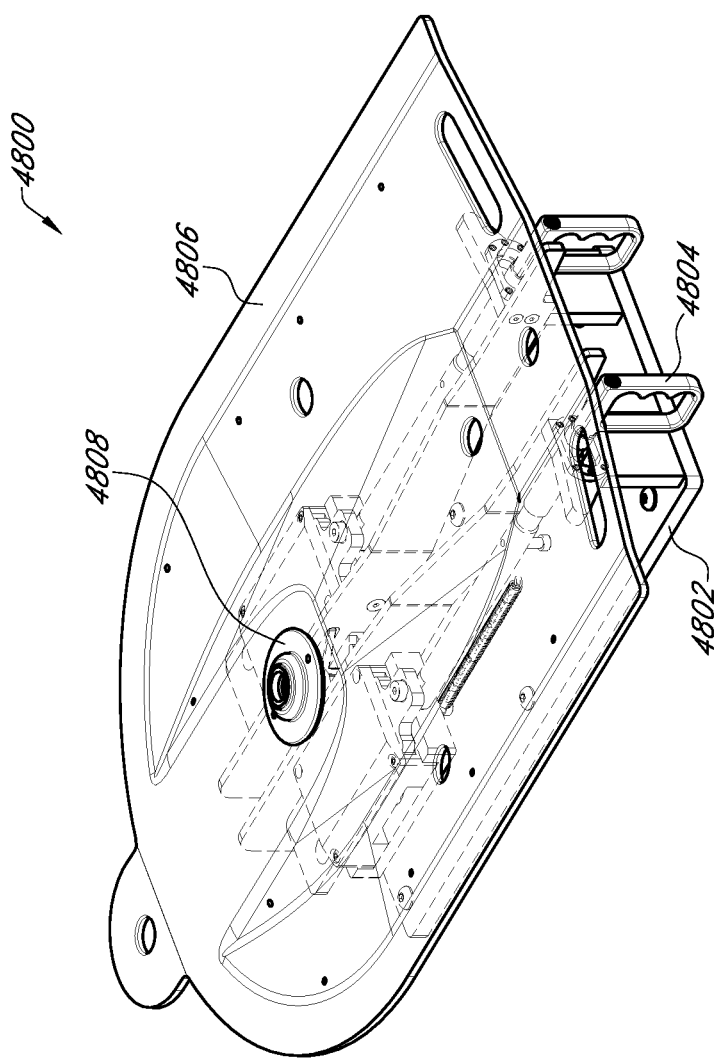
FIG. 49 illustrates a plate mount assembly 4900 in accordance with one embodiment.
Figure 50:
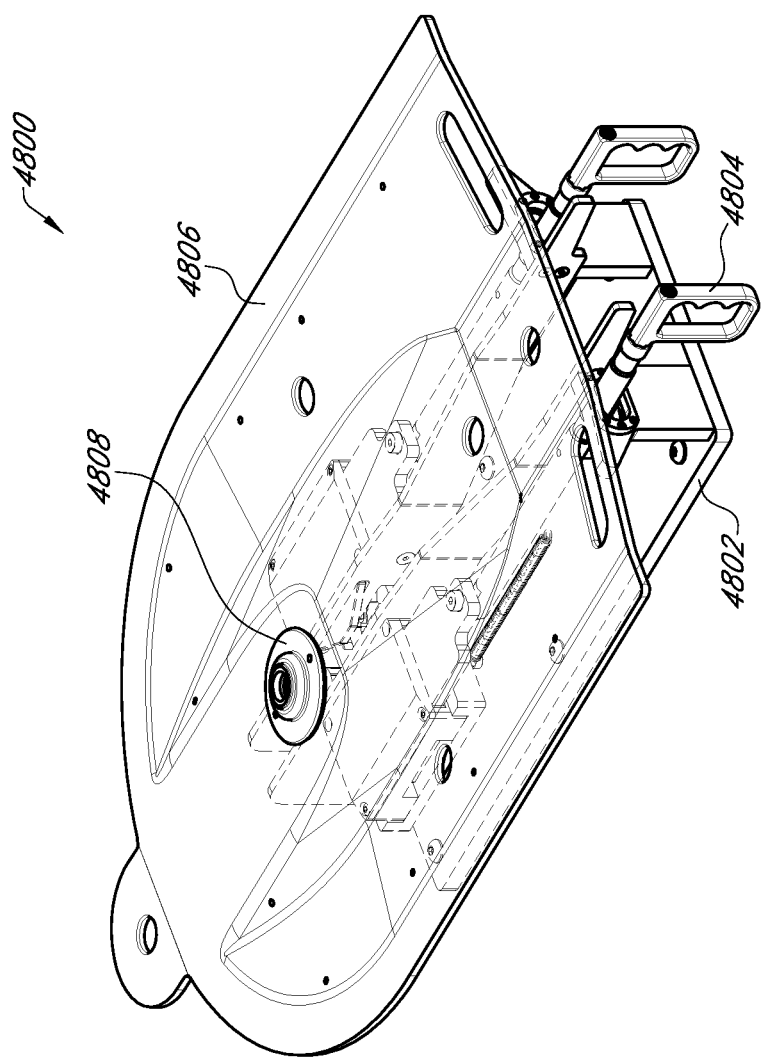
FIG. 50 illustrates a plate mount assembly in accordance with one embodiment.

FIG. 48 illustrates a plate mount assembly 4800 comprises a catch assembly 4802 and a tube management plate 4806 that has been fully inserted into the catch assembly 4802 according to various embodiments. In some embodiments, a portion of the tube management plate 4806 abuts against the rear sidewall 114 of the rigid housing 100 to indicate proper positioning. In some embodiments, a measuring device or key may be used. In the embodiment shown in FIG. 48, the handles 4804 protrude because the second recess of the rods are positioned in the rod guides. From this position, an operator may attempt to bring the rods into the wide tapered openings on the rod receivers to push them forward. The attempt will be success of the bearing housing 4808 is properly positioned within the catch assembly 4802. FIG. 49 illustrates an embodiment where an operator successfully installed the bearing housing 4808 into the catch assembly 4802 and was able to reposition the rods within the rod guides to the forward position where the rod guides accept the first recess of the rods. FIG. 50 illustrates an embodiment where an operator was unsuccessful in their attempt to position the bearing housing 4808 within the catch assembly 4802 and the rods will not move forward and the handles 4804 still protrude outwardly and will block the door 126 from closing. The operator may then reposition the bearing housing 4808 into its correct orientation within the catch assembly 4802.

Figure 51:
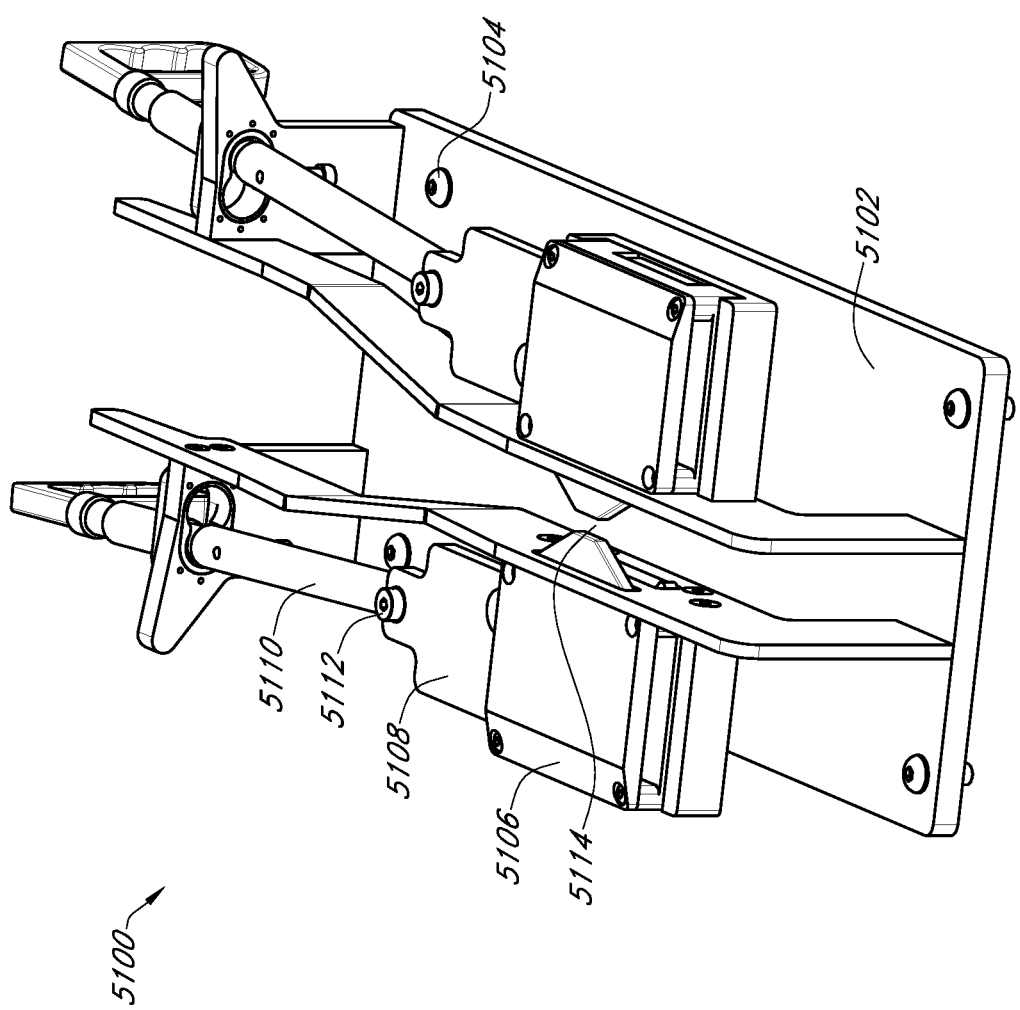
FIG. 51 illustrates a catch assembly 5100 in accordance with one embodiment.
Figure 52:
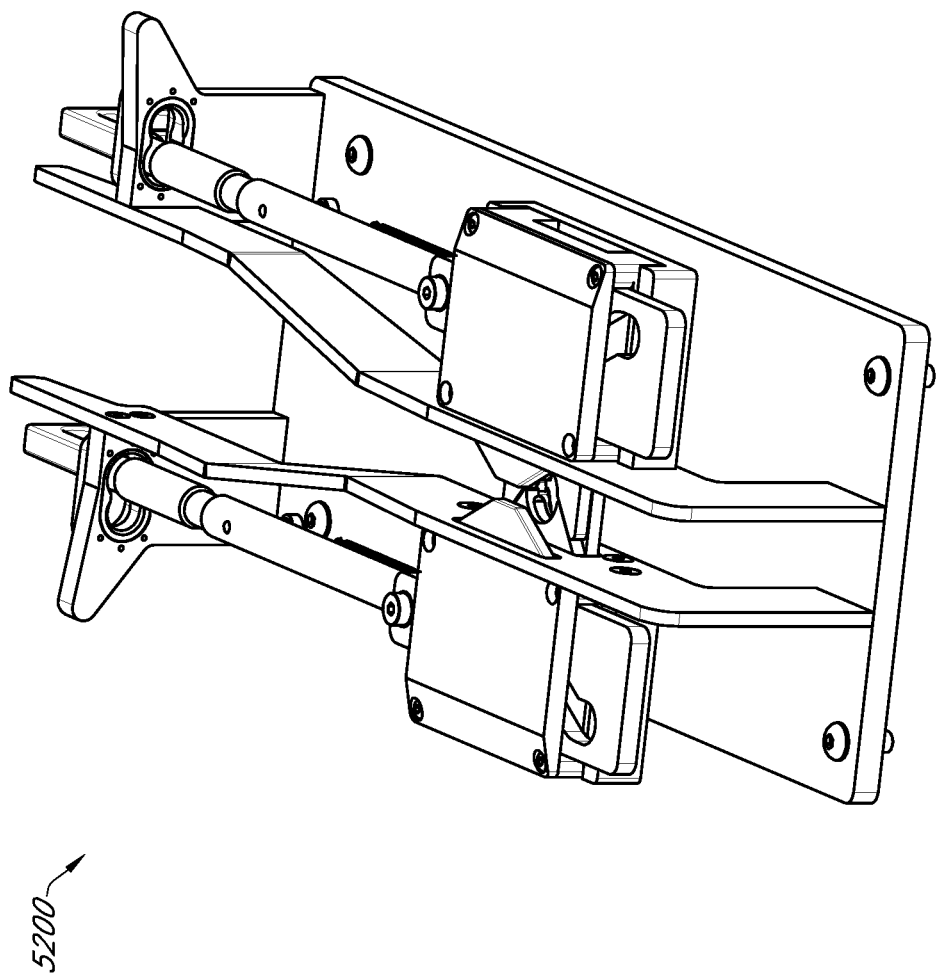
FIG. 52 illustrates a catch assembly 5200 in accordance with one embodiment.

FIGS. 51 and 52 illustrate a catch assembly 5100 according to various embodiments. FIG. 51 illustrates an embodiment where the catch assembly 5100 is open and ready to receive a bearing housing 4808 and FIG. 52 illustrates an embodiment where the catch assembly 5100 is closed and has received a bearing housing 4808 in a proper orientation (housing not shown).

In various embodiments, a catch assembly 5100 may include a plate 5102 that mounts to the floor 118 of the rigid housing 100 through an attachment 5104. In some embodiments, the attachment 5104 may be a screw, bolt, weld, or adhesive. In various embodiments, a catch mechanism 5106 may be secured to the plate 5102 and include a cam plate 5108 connected to a rod 5110 by an attachment 5112. In some embodiments, the attachment 5112 may include a pin, screw, bolt, weld, or anything else known or useful.

In various embodiments, the catch assembly 5100 may include a catch opening 5114 for receiving a bearing housing 4808. In FIG. 51 the catch opening 5114 is unobstructed and ready to receive a bearing housing 4808. In FIG. 52, the catch opening 5114 is surrounded by the catch mechanism 5106 to inhibit movement of the bearing housing 4808 and, therefore, the flexible container 400, 502, 600.

Figure 53:
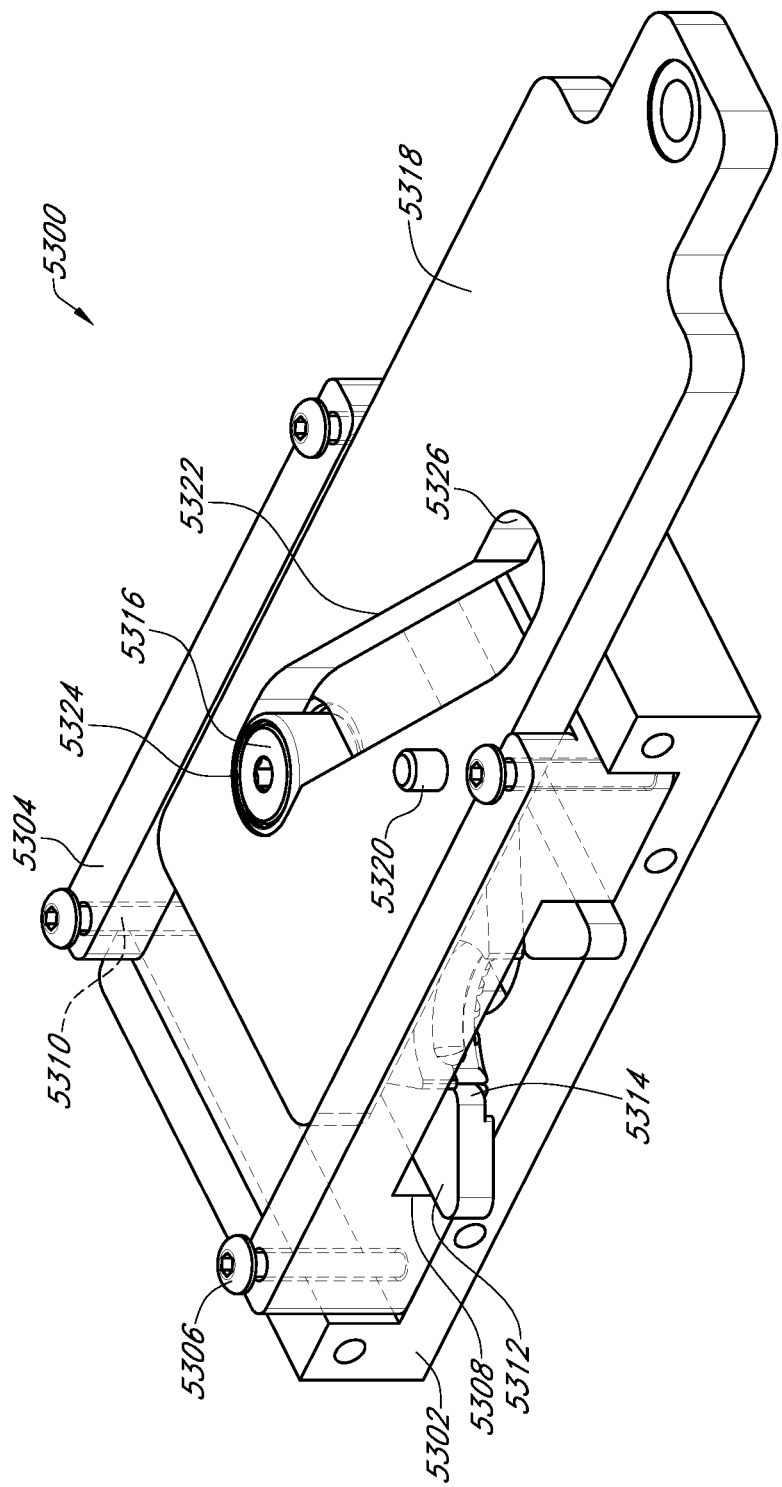
FIG. 53 illustrates a catch mechanism 5300 in accordance with one embodiment.

FIG. 53 illustrates a catch mechanism 5300 according to various embodiments. The catch mechanism 5300 may comprises a lower portion 5302, an upper portion 5304, a pin 5306, a catch plate track 5308, a cam plate track 5310, a catch plate 5312, an opening 5314, a protrusion 5316, a cam plate 5318, a dowel 5320, a cam guide 5322, an open slot 5324, and a closed slot 5326.

In various embodiments, a lower portion 5302 may join to an upper portion 5304 using a pin 5306, screw, bolt, adhesive or any other known method of joining two objects. In various embodiments, the upper portion 5304 may include a catch plate track 5308 that allows movement of a catch cam plate 5318 along an axis and a cam plate track 5310 allowing movement of a cam plate 5318 along another axis. In some embodiments, the axes run perpendicular to one another.

In various embodiments, a catch plate 5312 may include an opening 5314 for interacting with and restraining a bearing housing 4808 and may also include a protrusion 5316 and the protrusion 5316 may be a cam in some embodiments. In various embodiments, a cam plate 5318 may include a dowel 5320 as well as a cam guide 5322 having an open slot 5324 and a closed slot 5326.

Figure 54:
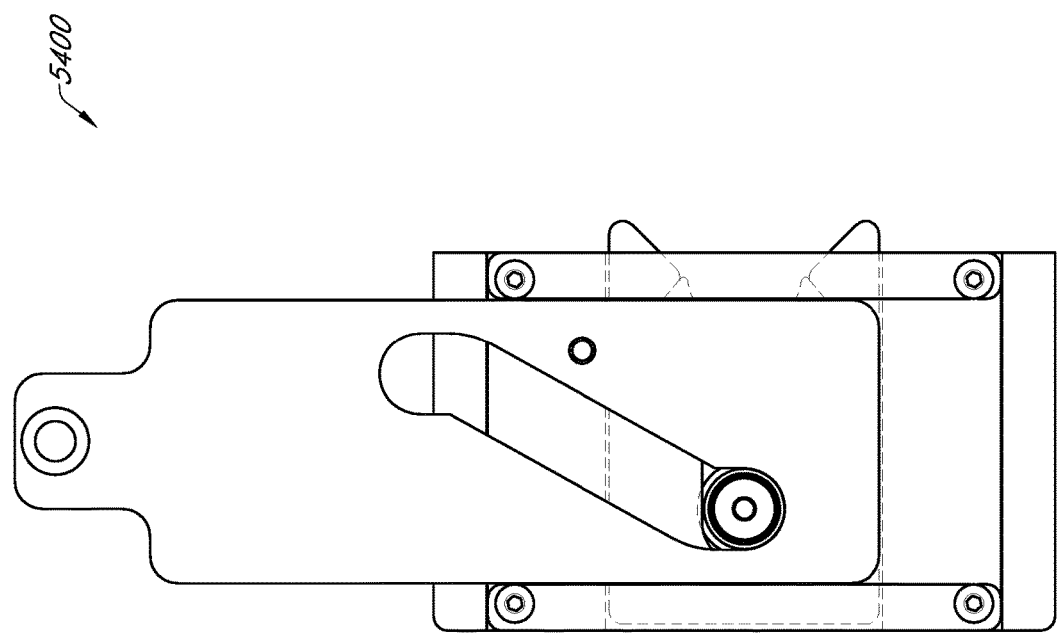
FIG. 54 illustrates an open catch mechanism 5400 in accordance with one embodiment.
Figure 55:
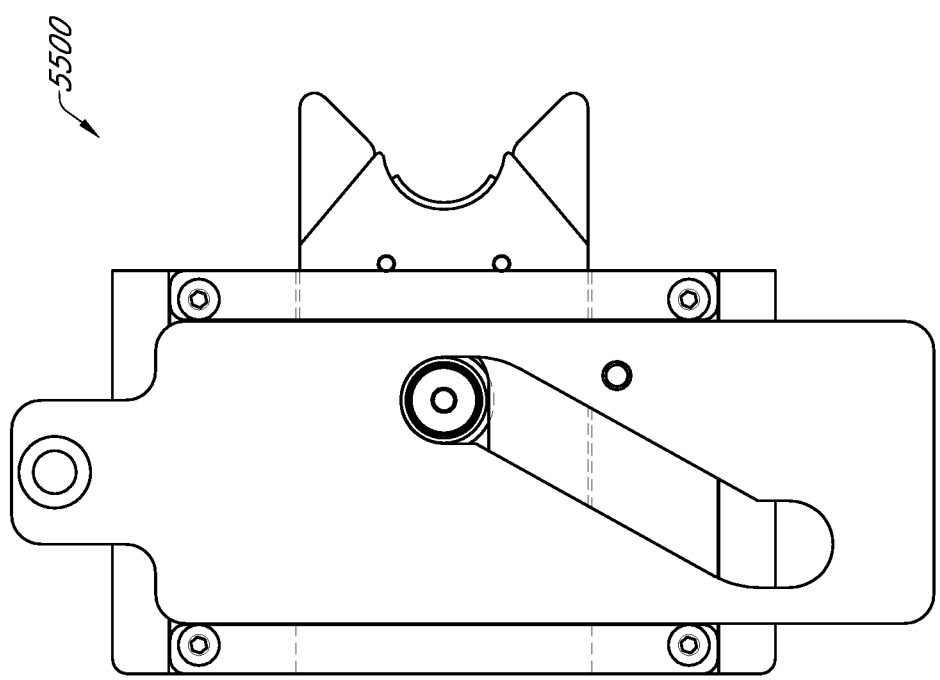
FIG. 55 illustrates a closed catch mechanism 5500 in accordance with one embodiment.

In various embodiments, the cam guide 5322 may be tapered, thereby, forcing movement of the catch plate 5312 as the edges of the cam guide 5322 interact with the protrusion 5316 on the catch plate 5312. FIG. 54 illustrates an embodiment where an operator has positioned the cam plate to an open configuration which has pulled the catch plate back into the interior of the catch mechanism 5300. FIG. 55 illustrates an embodiment where an operator has positioned the cam plate to a closed configuration which ash pushed the catch plate outward to catch and restrict movement of a bearing housing.

Figure 56:
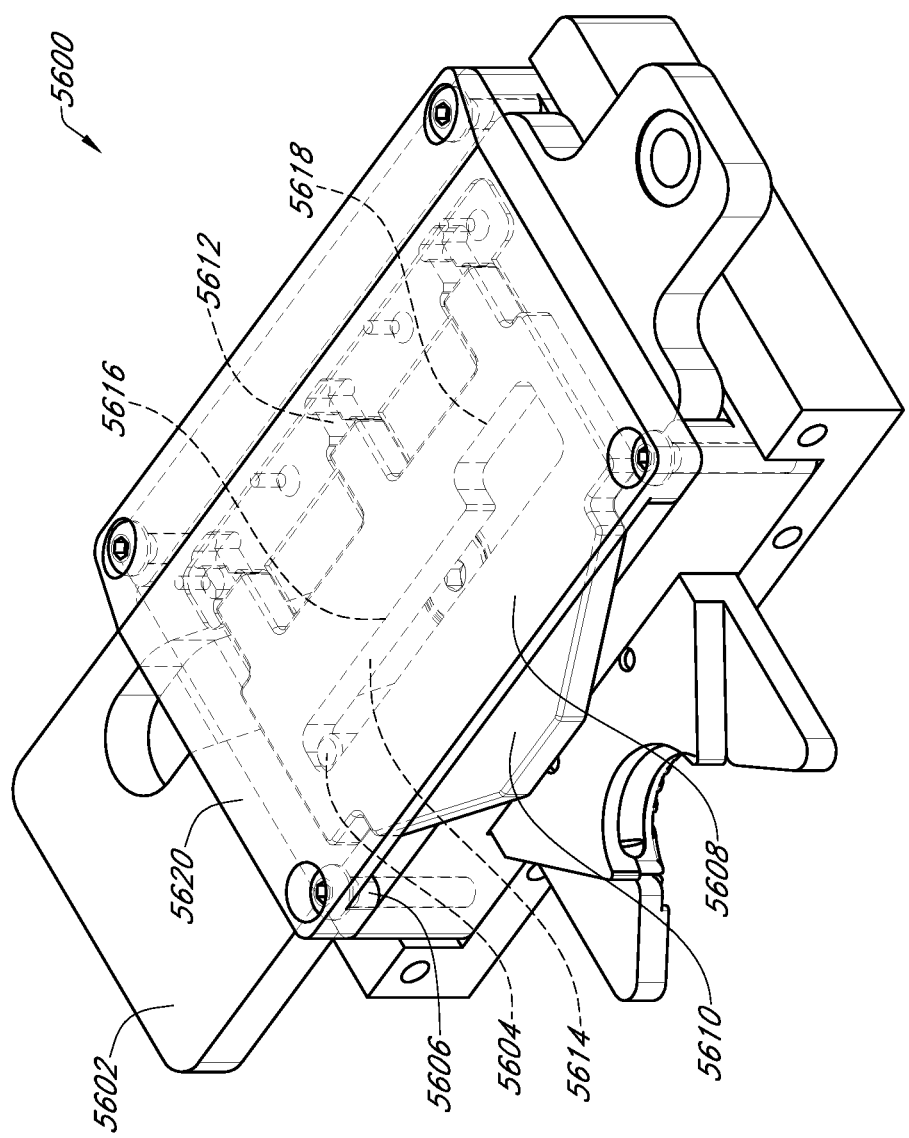
FIG. 56 illustrates a catch mechanism 5600 in accordance with one embodiment.
Figure 57:
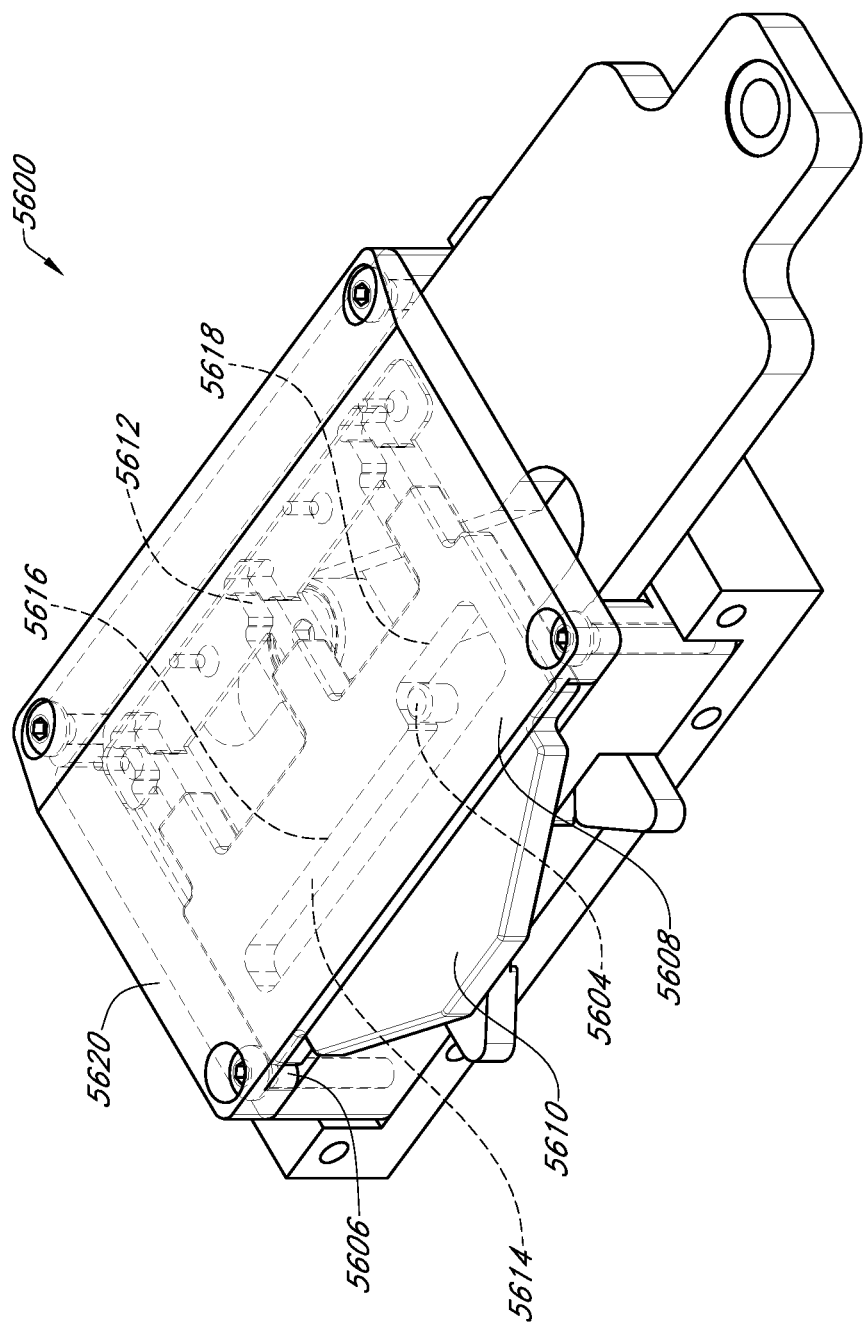
FIG. 57 illustrates a catch mechanism 5700 in accordance with one embodiment.
Figure 58:
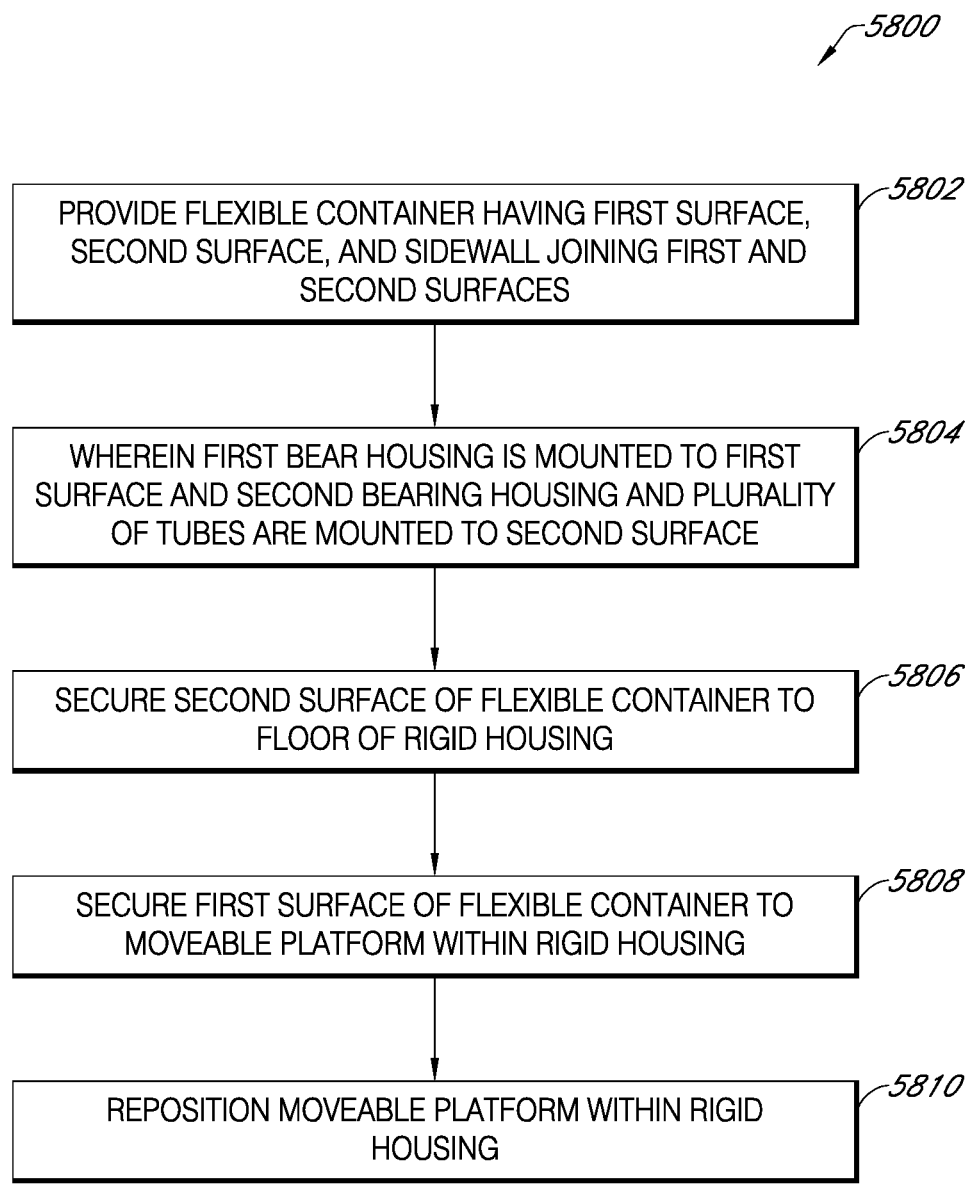
FIG. 58 illustrates a routine for installing a bioprocessing container within a bioproduction mixing system, in accordance with one embodiment.
Figure 59:
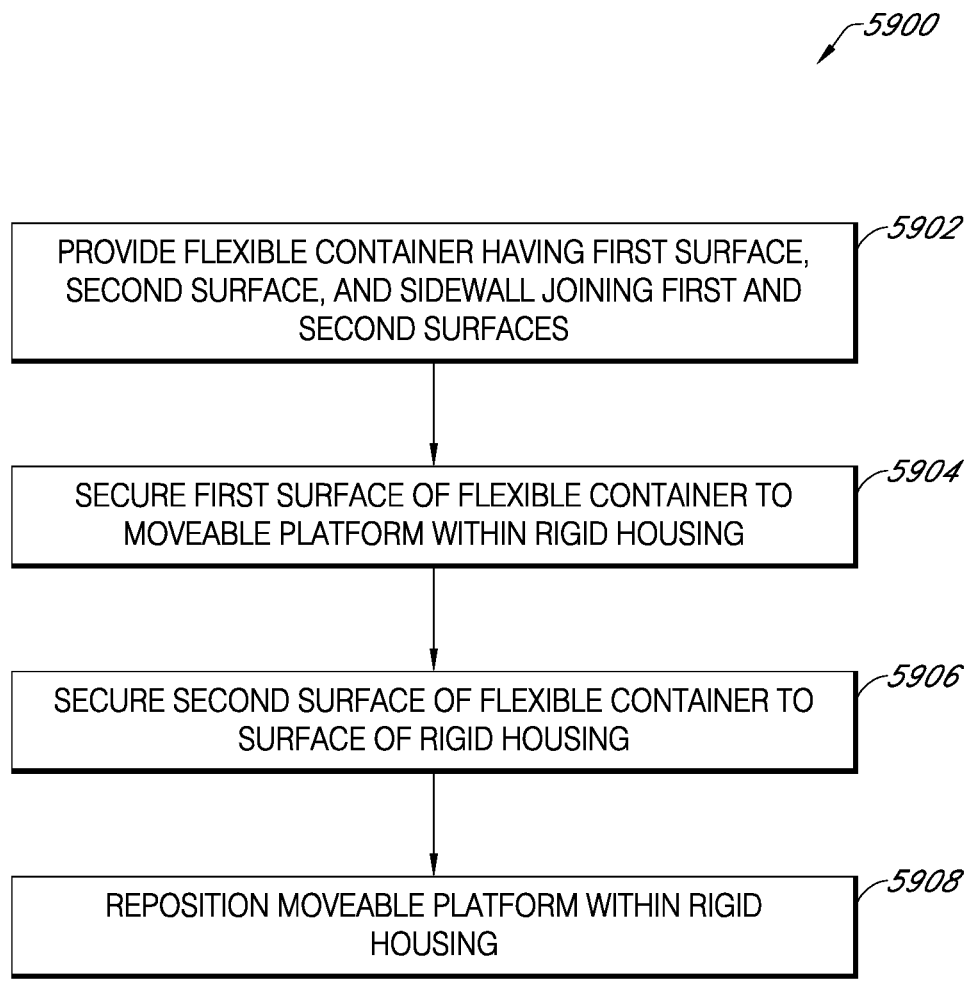
FIG. 59 illustrates a routine for installing a bioprocessing container within a bioproduction mixing system, in accordance with one embodiment.
Figure 60:
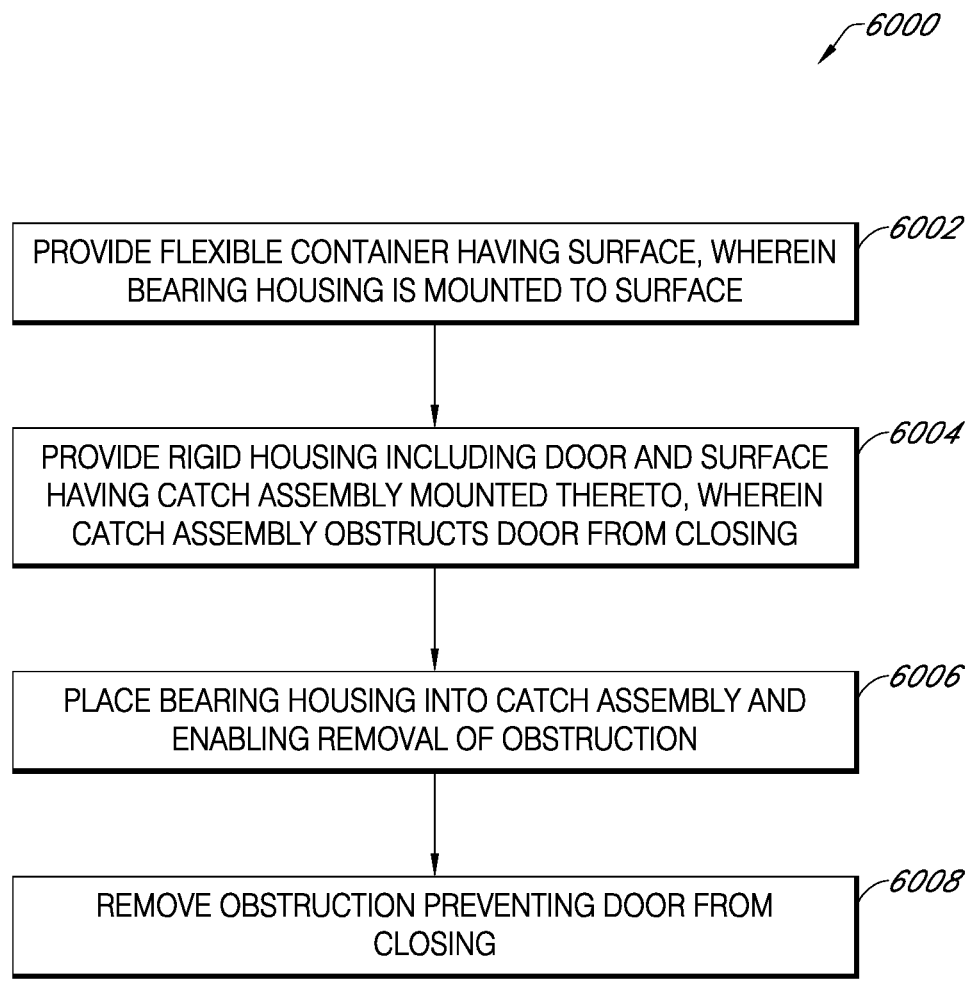
FIG. 60 illustrates a routine for installing a bearing housing in accordance with one embodiment.
Figure 61:
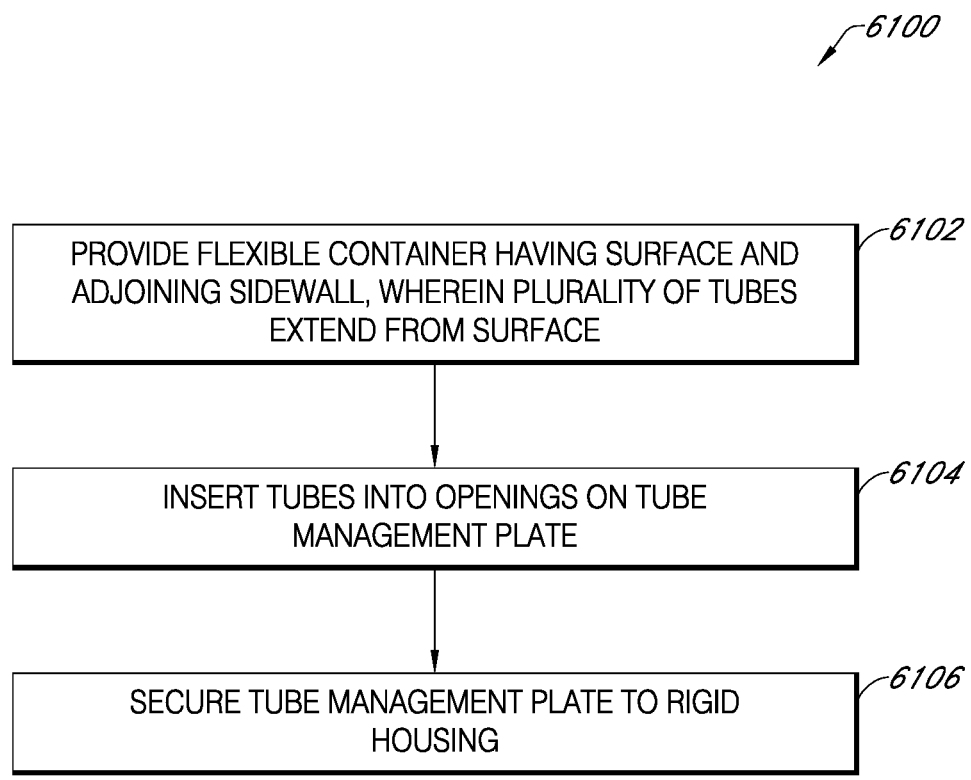
FIG. 61 illustrates a routine for installing tubing in accordance with one embodiment.
Figure 62:
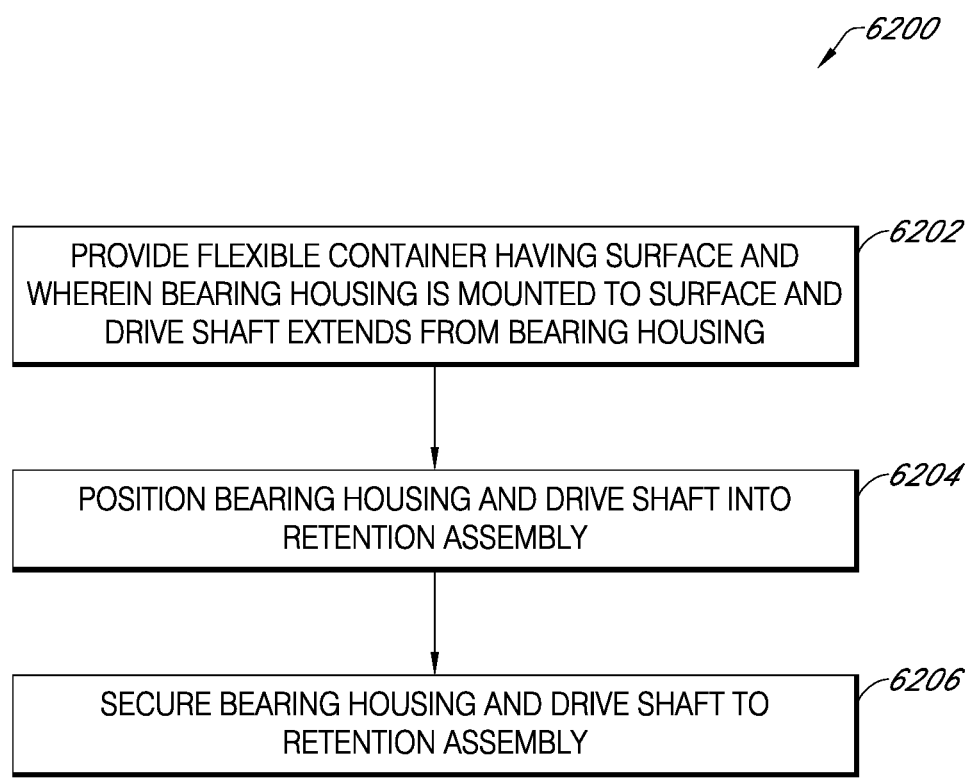
FIG. 62 illustrates a routine for mounting a bearing assembly and drive shaft of a bioprocessing container to a drive unit, in accordance with one embodiment.
Figure 63:
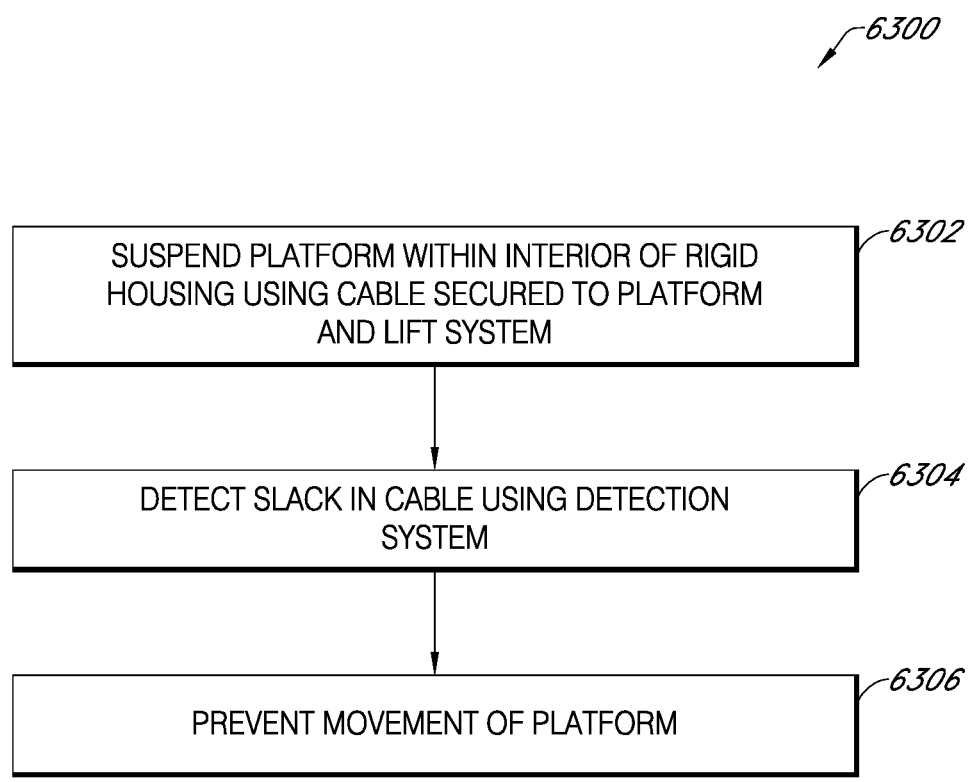
FIG. 63 illustrates a routine for detecting cable slack in accordance with one embodiment.
Figure 64:
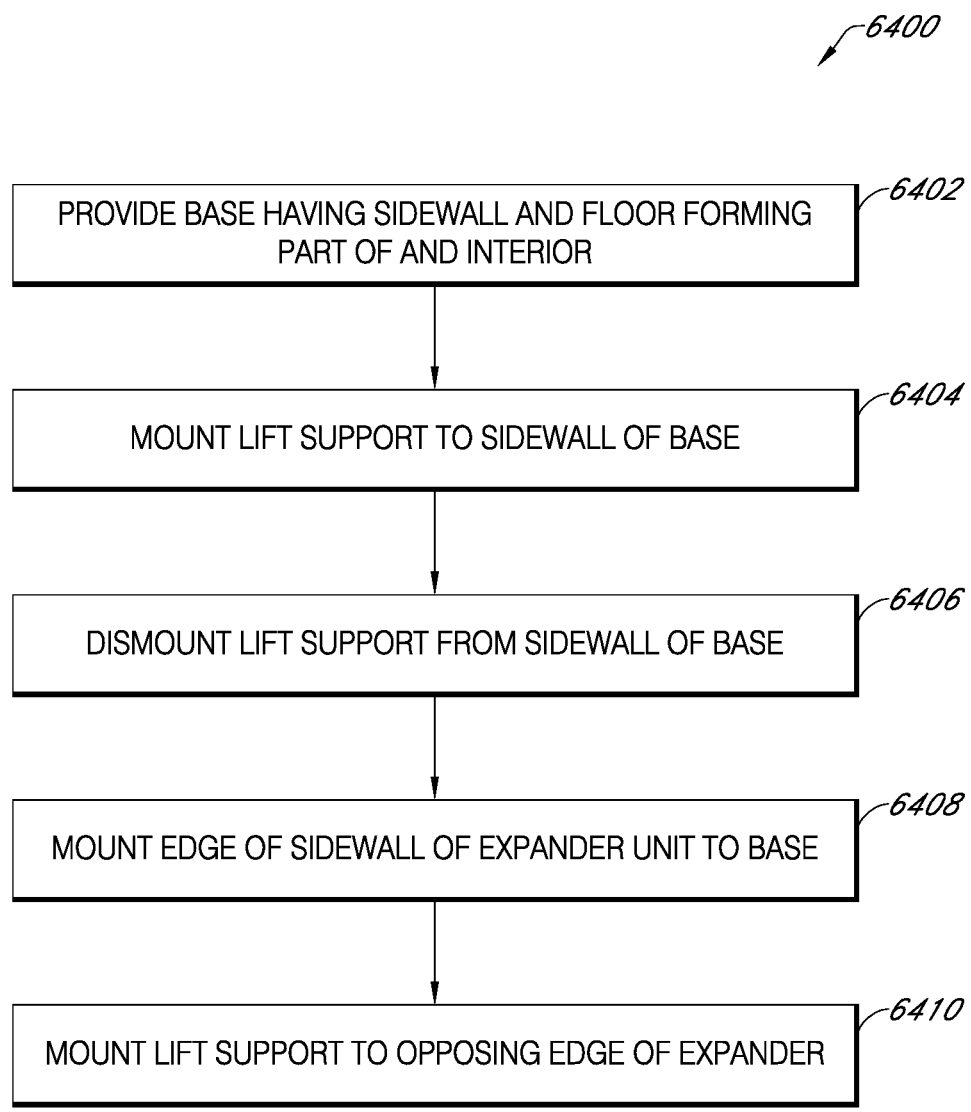
FIG. 64 illustrates a routine for expanding the volume of a single use bioproduction mixing system, in accordance with one embodiment.

FIGS. 56 and 57 illustrate a catch mechanism 5600 according to various embodiments. In various embodiments, the catch mechanism 5600 may comprise a cam plate 5602, a dowel 5604, an inhibitor portion 5606, an inhibitor plate 5608, a projection 5610, a spring 5612, a groove 5614, an elongated portion 5616, and a slot 5618.

In various embodiments, an inhibitor plate 5608 can be added to the catch mechanism 5300 as illustrated in FIGS. 53, 54, and 55. In some embodiments, an inhibitor portion 5606 attaches to the upper portion 5304 and may include an inhibitor plate track 5620 for guiding the inhibitor plate 5608. In various embodiments, a cam plate 5602 may include a dowel 5604 for interacting with an inhibitor plate 5608 along a groove 5614. In some embodiments, the inhibitor plate 5608 may be spring loaded to push a projection 5610 into a space where a bearing housing 4808 may enter the catch assembly 4802. In such an embodiment, the projection 5610 being thrust outwardly may be its resting position and the dowel 5604 on the cam plate 5602 may be struck in a slot 5618 and physically inhibited from moving into the elongated portion 5616 of the groove 5614. While the dowel 5604 resides in the slot 5618 of the groove 5614 the protrusion 5316 on the catch plate 5312 is unable to move along the cam guide 5322 on the cam plate and the catch assembly is forced to stay in an open configuration as shown in FIG. 57. While in the open configuration, the door 126 on the rigid housing 100 will not close due to physical inhibition by the handle 4804 on the rod 4502.

As illustrated in FIG. 56, a bearing housing 4808 (not shown) may be positioned near the opening of the catch plate 5312 which may then force the inhibitor plate 5608 to recede which may then allow the dowel 5604 to enter the elongated portion 5616 of the groove 5614 and the cam plate 5602 may then move to change the configuration of the catch assembly 5500 into a closed and locked configuration, thereby, securing the bearing housing 4808 and allowing the door 126 to close on the rigid housing 100.

In block 5802, routine 5800 provides a flexible container having a first surface, a second surface, and a sidewall joining the first and second surfaces. In block 5804, routine 5800 wherein a first bears housing is mounted to the first surface and a second bearing housing and a plurality of tubes are mounted to the second surface. In block 5806, routine 5800 secures the second surface of the flexible container to a floor of a rigid housing. In block 5808, routine 5800 secures the first surface of the flexible container to a moveable platform within the rigid housing. In block 5810, routine 5800 repositions the moveable platform within the rigid housing.

In block 5902, routine 5900 provides a flexible container having a first surface, a second surface, and a sidewall joining the first and second surfaces. In block 5904, routine 5900 secures the first surface of the flexible container to a moveable platform within a rigid housing. In block 5906, routine 5900 secures the second surface of the flexible container to a surface of the rigid housing. In block 5908, routine 5900 repositions the moveable platform within the rigid housing.

In block 6002, routine 6000 provides a flexible container having a surface, wherein a bearing housing is mounted to the surface. In block 6004, routine 6000 provides a rigid housing including a door and a surface having a catch assembly mounted thereto, wherein the catch assembly obstructs the door from closing. In block 6006, routine 6000 places the bearing housing into the catch assembly and enabling removal of the obstruction. In block 6008, routine 6000 removes an obstruction preventing the door from closing.

In block 6102, routine 6100 provides a flexible container having a surface and an adjoining sidewall, wherein a plurality of tubes extend from the surface. In block 6104, routine 6100 inserts the tubes into openings on a tube management plate. In block 6106, routine 6100 secures the tube management plate to the rigid housing.

In block 6202, routine 6200 provides a flexible container having a surface and an adjoining sidewall, wherein a bearing housing is mounted to the surface and a drive shaft extends from the bearing housing. In block 6204, routine 6200 positions the bearing housing and drive shaft into a retention assembly. In block 6206, routine 6200 secures the bearing housing and drive shaft to the retention assembly.

In block 6302, routine 6300 suspends a platform within an interior of a rigid housing using a cable secured to the platform and a lift system. In block 6304, routine 6300 detects slack in the cable using a detection system. In block 6306, routine 6300 prevents movement of the platform.

In block 6402, routine 6400 provides a base having a sidewall and a floor forming part of and interior. In block 6404, routine 6400 mounts a lift support to the sidewall of the base. In block 6406, routine 6400 dismounts the lift support from the sidewall of the base. In block 6408, routine 6400 mounts an edge of a sidewall of an expander unit to the base. In block 6410, routine 6400 mounts a lift support to an opposing edge of the expander.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art will readily appreciate that the sequences may be varied and still remain within the spirit and scope of the various embodiments.

What is claimed is:

1. A bioprocessing container installation system, comprising:
   a rigid housing having an interior compartment and including a lift system, wherein the lift system includes cables secured to a framework;
   a flexible container disposed within the interior compartment, the flexible container comprising:
      a first surface having at least two adjoining connectors;
      a second surface having at least two adjoining connectors; and a sidewall joining the first and second surfaces,
wherein a first bearing housing is mounted to the first surface and a second bearing housing is mounted to the second surface; and
a moveable platform positioned over the flexible container and within the interior compartment, the moveable platform comprising a drive assembly mounted thereto and including a plurality of cable attachment devices and a plurality of securing devices,
wherein the cables are operably connected to the cable attachment devices to suspend the moveable platform and the securing devices are operably connected to the at least two adjoining connectors of the first surface,
wherein the drive assembly mounted to the moveable platform includes a motor having a first bearing mount configured to receive the first bearing housing of the flexible container.

2. The bioprocessing container installation system of claim 1, wherein the rigid housing further comprises at least two retractable cable assemblies mounted adjacent to a floor of the rigid housing, wherein the retractable cable assemblies include hooks for attaching to the at least two adjoining connectors of the second surface.

3. The bioprocessing installation system of claim 1, wherein the flexible container further includes a plurality of ports joined to the second surface of the flexible container.

4. The bioproces sing installation system of claim 3, further including a tube management plate having a plurality of openings and a bearing receiver, said plurality of openings arranged to receive a plurality of tubes extending from the ports and said bearing receiver configured to receive and restrict movement of the second bearing housing relative to the tube management plate.

5. The bioprocessing installation system of claim 4, wherein a floor of the rigid housing includes an opening bounded by a groove for receiving a perimeter edge of the tube management plate.

6. The bioprocessing container installation system of claim 1, further comprising:
a motive force device mounted to the exterior of the rigid housing; and
a plurality of routing pulleys and suspension pulleys mounted to the framework, wherein the routing pulleys are configured to direct the cables from the motive force device to the suspension pulleys and the suspension pulleys direct the cable to the cable attachment devices on the moveable platform.

7. The bioprocessing container installation system of claim 6, wherein the motive force device includes a pneumatic cylinder.

8. The bioprocessing container installation system of claim 6, wherein the moveable platform further comprises a slack sensor assembly mounted thereto, comprising:
a spring-loaded rod having a first end and a second end, wherein the spring-loaded rod is configured to actuate from a first position to a second position when a force on the spring changes;
a cable attachment affixed to the first end of the spring-loaded rod, wherein the cable attachment is configured to receive the cable;
a readable object affixed to the second end of the spring-loaded rod; and
a slack sensor configured to detect the position of the readable object.

9. The bioproces sing container installation system of claim 8, wherein the positional change of the readable object causes the slack sensor to send a signal to a controller to deactivate the motive force device.

10. The bioprocessing container installation system of claim 1, wherein the framework further comprises a moveable platform securing assembly, comprising:
a protrusion receiver having a plurality of protrusion openings and configured to actuate between a first position and a second position; and
an actuator mounted to the protrusion receiver, the actuator configured to drive the protrusion receiver between the first and second positions.

11. The bioprocessing container installation system of claim 10, wherein a plurality of protrusions are mounted to the moveable platform, wherein the plurality of protrusions are configured to extend into the plurality of protrusion opens while the protrusion receiver is in the first position and become locked in place when the protrusion receiver actuates to the second position.

12. The bioprocessing container installation system of claim 1, wherein the flexible container further comprises a helical drive assembly extending from the first bearing housing mounted to the first surface to the second bearing housing mounted to the second surface, such that the motor may provide rotational movement to the helical drive assembly through the first bearing mount and the first bearing housing.

13. The bioprocessing container installation system of claim 1, wherein the moveable platform further comprises at least one sensor mounted thereto.

14. The bioprocessing container installation system of claim 1, wherein the plurality of securing devices are slidably mounted to the moveable platform between a rear position and a forward position.

15. The bioprocessing container installation system of claim 1, wherein the moveable platform further comprises a tube holder and/or a clamp mounted on a top surface of the moveable platform.

16. The bioprocessing installation system of claim 5, wherein the at least two adjoining connectors of the second surface of the flexible container are operably connected to the floor of the rigid housing.

17. The bioprocessing container installation system of claim 1, wherein the moveable platform further comprises a plurality of openings defined therethrough.

18. The bioprocessing container installation system of claim 1, wherein the plurality of securing devices further comprises at least two retractable cable assemblies mounted on a top surface of the moveable platform, wherein the retractable cable assemblies include hooks for attaching to the at least two adjoining connectors of the first surface.

* * * * *